United States Patent
Singer et al.

(10) Patent No.: US 9,849,179 B2
(45) Date of Patent: *Dec. 26, 2017

(54) METHODS FOR TOPICAL DELIVERY OF PROSTAGLANDINS TO SUBCUTANEOUS FAT

(71) Applicant: Topokine Therapeutics, Inc., Newton, MA (US)

(72) Inventors: Michael S. Singer, Newton Center, MA (US); Murat V. Kalayoglu, Silver Spring, MD (US)

(73) Assignee: Topokine Therapeutics, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/702,365

(22) Filed: May 1, 2015

(65) Prior Publication Data

US 2015/0231251 A1    Aug. 20, 2015

Related U.S. Application Data

(63) Continuation of application No. 14/575,873, filed on Dec. 18, 2014, now Pat. No. 9,040,584, which is a continuation of application No. PCT/US2014/037512, filed on May 9, 2014.

(60) Provisional application No. 61/822,139, filed on May 10, 2013.

(51) Int. Cl.
| | |
|---|---|
| *A61K 31/557* | (2006.01) |
| *A61K 47/14* | (2017.01) |
| *A61K 31/5575* | (2006.01) |
| *A61K 47/06* | (2006.01) |
| *A61K 47/10* | (2017.01) |
| *A61K 9/00* | (2006.01) |

(52) U.S. Cl.
CPC ............ *A61K 47/14* (2013.01); *A61K 9/0014* (2013.01); *A61K 31/5575* (2013.01); *A61K 47/06* (2013.01); *A61K 47/10* (2013.01)

(58) Field of Classification Search
CPC .................................................. A61K 31/5575
USPC ........................................................ 514/573
See application file for complete search history.

(56) References Cited

U.S. PATENT DOCUMENTS

| | | | |
|---|---|---|---|
| 4,270,537 A | 6/1981 | Romaine | |
| 4,596,556 A | 6/1986 | Morrow et al. | |
| 4,599,353 A | 7/1986 | Bito | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,011,062 A | 4/1991 | Nakanishi et al. | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,296,504 A | 3/1994 | Stjernschantz et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |
| 5,422,368 A | 6/1995 | Stjernschantz et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,631,287 A | 5/1997 | Schneider | |
| 5,649,912 A | 7/1997 | Peterson | |
| 5,688,819 A | 11/1997 | Woodward et al. | |
| 5,704,911 A | 1/1998 | Parsons | |
| 5,849,792 A | 12/1998 | Schneider | |
| 5,886,035 A | 3/1999 | Shirasawa et al. | |
| 5,889,052 A | 3/1999 | Klimko et al. | |
| 5,893,397 A | 4/1999 | Peterson et al. | |

(Continued)

FOREIGN PATENT DOCUMENTS

| | | |
|---|---|---|
| CN | 101427993 A | 5/2009 |
| EA | 006556 B1 | 2/2006 |

(Continued)

OTHER PUBLICATIONS

U.S. Appl. No. 11/712,839, filed Mar. 1, 2007, Grosskreutz et al.

(Continued)

*Primary Examiner* — Kevin E Weddington
(74) *Attorney, Agent, or Firm* — Wolf, Greenfield & Sacks, P.C.

(57) ABSTRACT

Described herein are compositions comprising a prostaglandin FP receptor agonist (PFPRA) compound and a fatty acid ester (e.g., isopropyl myristate), optionally comprising an ointment base such as a hydrocarbon base (e.g., petroleum jelly) and/or an organic alcohol (e.g., propylene glycol), that, when topically applied to the skin, locally delivers a therapeutically effective amount of the PFPRA compound to subcutaneous fat under the skin, and methods of preparation. The therapeutic effect is, for example, reduction of the subcutaneous fat under the skin. Further provided are methods of reducing body fat in a subject comprising topically administering the composition to the subject.

28 Claims, 1 Drawing Sheet

(56) References Cited

U.S. PATENT DOCUMENTS

| | | | |
|---|---|---|---|
| 5,972,991 A | 10/1999 | Burk | |
| 5,990,139 A | 11/1999 | Yano et al. | |
| 5,993,412 A | 11/1999 | Deily et al. | |
| 6,232,344 B1 | 5/2001 | Feng et al. | |
| 6,235,781 B1 | 5/2001 | Weiner et al. | |
| 6,262,105 B1 | 7/2001 | Johnstone | |
| 6,403,649 B1 | 6/2002 | Woodward et al. | |
| 6,646,001 B2 | 11/2003 | Hellberg et al. | |
| 6,730,707 B2 | 5/2004 | Pintor et al. | |
| 6,864,282 B2 | 3/2005 | Ling et al. | |
| 6,911,474 B2 | 6/2005 | Piomelli et al. | |
| 6,933,289 B2 | 8/2005 | Lyons et al. | |
| 7,070,768 B2 | 7/2006 | Krauss | |
| 7,125,542 B2 | 10/2006 | Miller et al. | |
| 7,351,404 B2 | 4/2008 | Woodward et al. | |
| 7,622,130 B2 | 11/2009 | Kolodney et al. | |
| 7,666,912 B2 | 2/2010 | Grosskreutz et al. | |
| 8,273,362 B2 | 9/2012 | Philips et al. | |
| 8,367,606 B2 | 2/2013 | Tennenbaum et al. | |
| 8,426,471 B1 | 4/2013 | Kalayoglu et al. | |
| 8,569,376 B2 | 10/2013 | Kalayoglu et al. | |
| 8,722,097 B2 | 5/2014 | Chang et al. | |
| 8,778,981 B2 | 7/2014 | Kalayoglu et al. | |
| 8,829,050 B2 * | 9/2014 | Grosskreutz | A61K 31/5575 514/573 |
| 8,841,345 B2 | 9/2014 | Lu et al. | |
| 8,877,807 B2 | 11/2014 | Grosskreutz et al. | |
| 9,040,584 B2 * | 5/2015 | Singer | A61K 31/23 514/573 |
| 9,089,579 B2 | 7/2015 | Kalayoglu | |
| 9,144,574 B2 | 9/2015 | Grosskreutz | |
| 9,180,130 B2 | 11/2015 | Kalayoglu et al. | |
| 2002/0172693 A1 | 11/2002 | DeLong et al. | |
| 2003/0181354 A1 | 9/2003 | Abdulrazik | |
| 2004/0023954 A1 | 2/2004 | Ling et al. | |
| 2004/0082660 A1 | 4/2004 | Ueno | |
| 2004/0115234 A1 | 6/2004 | Gewirtz | |
| 2004/0241245 A1 | 12/2004 | Lu et al. | |
| 2005/0058614 A1 | 3/2005 | Krauss | |
| 2005/0117830 A1 | 6/2005 | Hartog et al. | |
| 2005/0261373 A1 | 11/2005 | Ueno | |
| 2006/0246145 A1 | 11/2006 | Chang et al. | |
| 2007/0224246 A1 | 9/2007 | Hughes et al. | |
| 2007/0248658 A1 | 10/2007 | Zurdo Schroeder et al. | |
| 2008/0015257 A1 | 1/2008 | Grosskreutz et al. | |
| 2008/0107738 A1 | 5/2008 | Philips et al. | |
| 2008/0233053 A1 | 9/2008 | Gross et al. | |
| 2009/0042909 A1 | 2/2009 | Karnik | |
| 2010/0104654 A1 | 4/2010 | Robinson et al. | |
| 2010/0105771 A1 | 4/2010 | Delong et al. | |
| 2010/0234466 A1 | 9/2010 | Grosskreutz et al. | |
| 2010/0291226 A1 | 11/2010 | Mazzone et al. | |
| 2011/0124736 A1 | 5/2011 | Trogden et al. | |
| 2012/0046256 A1 | 2/2012 | Dobak | |
| 2012/0129789 A1 | 5/2012 | Yoelin | |
| 2012/0295972 A1 | 11/2012 | Woodward et al. | |
| 2013/0178525 A1 | 7/2013 | Kalayoglu et al. | |
| 2014/0045933 A1 | 2/2014 | Kalayoglu | |
| 2014/0163098 A1 | 6/2014 | Grosskreutz et al. | |
| 2014/0350104 A1 | 11/2014 | Kalayoglu et al. | |
| 2015/0025150 A1 | 1/2015 | Kalayoglu | |
| 2015/0025151 A1 | 1/2015 | Grosskreutz et al. | |
| 2015/0105462 A1 | 4/2015 | Singer et al. | |
| 2015/0164765 A1 | 6/2015 | Yoelin | |
| 2015/0359801 A1 | 12/2015 | Grosskreutz et al. | |

FOREIGN PATENT DOCUMENTS

| | | | |
|---|---|---|---|
| EP | 302147 A1 | 2/1989 | |
| EP | 1 864 666 A1 | 12/2007 | |
| EP | 2 228 058 A1 | 9/2010 | |
| EP | 3 124 015 A1 | 2/2017 | |
| KR | 20140043562 A | 10/2014 | |
| RU | 2157689 C2 | 10/2000 | |
| RU | 2325912 C1 | 6/2008 | |
| RU | 2009140073 A | 5/2011 | |
| WO | WO 97/13537 A1 | 4/1997 | |
| WO | WO 97/37705 A1 | 10/1997 | |
| WO | WO 99/34850 A1 | 7/1999 | |
| WO | WO 03/066008 A1 | 8/2003 | |
| WO | WO 2005/034889 A2 | 4/2005 | |
| WO | WO 2005/034890 A2 | 4/2005 | |
| WO | WO 2007/111806 A2 | 10/2007 | |
| WO | WO 2007111806 A2 * | 10/2007 | A61K 31/5575 |
| WO | WO 2010/039535 A1 | 4/2010 | |
| WO | WO 2010/100217 A1 | 9/2010 | |
| WO | WO 2011/057129 A2 | 5/2011 | |
| WO | WO 2012/068515 A2 | 5/2012 | |
| WO | WO 2012/099942 A2 | 7/2012 | |
| WO | WO 2012/131734 A1 | 10/2012 | |

OTHER PUBLICATIONS

U.S. Appl. No. 12/652,968, filed Jan. 6, 2010, Grosskreutz et al.
U.S. Appl. No. 14/180,074, filed Feb. 13, 2014, Grosskreutz et al.
U.S. Appl. No. 14/504,788, filed Oct. 2, 2014, Grosskreutz et al.
U.S. Appl. No. 13/548,482, filed Jul. 13, 2012, Kalayoglu et al.
U.S. Appl. No. 13/782,659, filed Mar. 1, 2013, Kalayoglu et al.
U.S. Appl. No. 14/363,923, filed Jun. 9, 2014, Kalayoglu et al.
U.S. Appl. No. 14/575,873, filed Dec. 18, 2014, Kalayoglu et al.
U.S. Appl. No. 13/980,179, filed Oct. 18, 2013, Kalayoglu.
U.S. Appl. No. 14/509,680, filed Oct. 8, 2014, Kalayoglu.
International Preliminary Report on Patentability, dated Nov. 26, 2015, in connection with PCT/US2014/038067.
Extended European Search Report, dated Dec. 21, 2015, in connection with EP 15180363.2.
Invitation to Pay Additional Fees for PCT/US2007/005424, dated Aug. 10, 2007.
International Search Report and Written Opinion for Application No. PCT/US2007/005424, dated Nov. 26, 2007.
International Preliminary Report on Patentability for Application No. PCT/US2007/005424, dated Sep. 23, 2008.
International Search Report and Written Opinion for Application No. PCT/US2012/070581, dated May 30, 2013.
International Preliminary Report on Patentability for Application for PCT/US2012/070581, dated Jul. 3, 2014.
International Search Report and Written Opinion for Application No. PCT/US2014/038067, dated Sep. 29, 2014.
Invitation to Pay Additional Fees for Application No. PCT/US2014/037512, dated Aug. 21, 2014.
International Search Report and Written Opinion for Application No. PCT/US2014/037512, dated Dec. 4, 2014.
Extended European Search Report for Application No. EP 12736090.7, dated Jul. 8, 2014.
Invitation to Pay Additional Fees for PCT/US2012/021692, dated Feb. 21, 2013.
International Search Report and Written Opinion for Application for PCT/US2012/021692, dated May 3, 2013.
International Preliminary Report on Patentability for Application for PCT/US2012/021692, dated Aug. 1, 2013.
[No Author Listed], Adrenal Disorders: Cushing Syndrome. Merck Manual Professional. Last revised Nov. 2007. Available at http://www.merck.com/mmpe/sec12/ch153/ch153e.html. Last visited Dec. 22, 2008.
[No Author Listed], Allergan Announces FDA Approval of Lumigan as First-Line Treatment for Elevated Eye Pressure in Open-Angle Glaucoma; Indication Expands Approved Uses of Lumigan in the Management of Glaucoma. Business Wire. Jun. 23, 2006. Available at http://findarticles.com/p/articles/mi_m0EIN/is_2006June_23/ai_n26905641. Last visited Aug. 7, 2008. 2 pages.
[No Author Listed], Allergan Announces FDA Approval of Lumigan® as First-Line Treatment for Elevated Eye Pressure in Open-Angle Glaucoma; Indication Expands Approved Uses of Lumigan(R) in the Management of Glaucoma. Allergan Press Release. Jun. 23, 2006. Avaiable at http://agn360.client.shareholder.com/releasedetail.cfm?ReleaseID=201809. Last visited Sep. 9, 2008. 3 pages.

(56) References Cited

OTHER PUBLICATIONS

[No Author Listed], Chapter 42. Pharmacology of Eicosanoids. In: Principles of Pharmacology. The Pathophysiologic Basis of Drug Therapy. 3rd ed. Golan et al., eds. 2012: 743.
[No Author Listed], Definition of "prevent". WordNet Search 3.1. http://wordnet.princeton.edu [last accessed Sep. 18, 2012]. 1 page.
[No Author Listed], Dexamethasone Crystalline Product Information, Sigma Prod. No. D1756, dated Mar. 2001. 2 pages.
[No Author Listed], Excerpts from BodybuildingForYou—Bodybuilding Forums: Anabolic Steroids-Prohormones, and Testosterone Enhancers <http://www.bodybuildingforyou.com/forums/anabolic-steroids-prohormones-testosterone-enhancers/>/ Anabolic Steroids & Anabolic Chemistry & Testosterone Enhancers <http://www.bodybuildingforyou.com/forums/anabolic-steroids-anabolic-chemistry-testosterone-enhancers/>/ Anabolic Steroid, HGH, IGF, Insulin and Ancillary Profiles, pgf2a parts 3-5, post Nos. 35-37 by RRAdam on Jul. 12, 2005, http://www.bodybuildingforyou.com/forums/anabolic-steroids-anabolic-chemistry-testosterone-enhancers/22591-anabolic-steroid-hgh-igf-insulin-ancillary-profiles-2.html (14 pages).
[No Author Listed], Excerpts from Wanna Be Big Bodybuilding and Weightlifting Forums: Community Central <http://www.wannabebigforums.com/archive/index.php/f-20.html>/ General Chat <http://www.wannabebigforums.com/archive/index.php/f-12.html>/The Myostatin Gene, posted at 4:22pm, Feb. 5, 2001, by Cackerot69, http://www.wannabebicforums.com/archive/index.php/t-359.html (4 pages).
[No Author Listed], FDA CDER Approval Letter (3 pages) and Toxicology Study #5 from CDER Pharmacology Review (cover page and pp. 43-44 of 107 included) for Lumigan (Bimatoprost Ophthalmic Solution), NDA Application No. 21-275 (FDA Approval Date: Mar. 16, 2001), available at http://www.fda.gov/cder/foi/nda/2001/21275_Lumigan.htm (last visited May 23, 2008).
[No Author Listed], FDA CDER Toxicology Study #18 from CDER Pharmacology Review (cover page and pp. 67-69 of 107 included) for Lumigan (Bimatoprost Ophthalmic Solution), NDA Application No. 21-275 (FDA Approval Date: Mar. 16, 2001), available at http://www.fda.gov/cdergoi/nda/2001/21275_Lumigan.htm (last visited Dec. 22, 2008).
[No Author Listed], KEGG Database, Eicosanoids—Reference Pathway, available at http://www.genome.jp/kegg/pathway/map/map07034.html (last visited Jun. 10, 2008, 1 page).
[No Author Listed], Kegg Drug: D02724, [online] retrieved on Nov. 30, 2007, (2007), retrieved from http://www.genome.ad.jp/dbget-bin/www_bget?drug+D02724 and http://www.genome.ad.jp/dbget-bin/www_bget?pathway+map07035, printed p. 1 and printed pp. 1-3, respectively.
[No Author Listed], Latisse and Safety. Last accessed on Jul. 24, 2012 at http://www.latisseonline.com/latisse-safety/ 2 pages.
[No Author Listed], Material Safety Data Sheet for Lutalyse® Sterile Solution, dated Jun. 23, 1997, available at httplApfww.lutelysacomipahirnageslmsde...usiLutalvse.pdf (last visited Dec. 22, 2006).
[No Author Listed], Material Safety Data Sheet: Dimethyl Sulfoxide. OSHA-DOT. www.pattersonvet.com/msds/078406593 [last accessed Apr. 2, 2015]. 3 pages.
[No Author Listed], Ointments: Preparation and Evaluation of Drug Release. The Pharmaceutics and Compounding Laboratory. Mar. 4, 2013. http://pharmlabs.unc.edu/ointments/bases.htm. 2 pages.
[No Author Listed], Original New Animal Drug Application for ProstaMateTm (dinoprost tromethamine injection) Sterile Solution (ANADA No. 200-253). Dated Feb. 12, 1999. Available at http://www.fdagovlohrmsidockets/98fr1200253fi.pdf. Last visited Dec. 22, 2008.
[No Author Listed], Pfizer Inc., Citizen Petition to the Food and Drug Administration: Revoke Approval of Allergan's Supplemental NDA #21-257/S-013 for Lumigan (Bimatoprost Ophthalmic Solution 0.03%) and Deny Alcon's Supplemental NDA for Travatan (Travoprost Ophthalmic Solution 0.004%), Docket No. 2006P-0450, submitted on Nov. 1, 2006, available at http://www.fda.gov/ohrms/dockets/dockets/06p0450/06p-0450-cp00001-toc.htm.
[No Author Listed], Prescribing Information for SAFLUTAN® 15 micrograms/ml eye drops, solution, single-dose container (tafluprost), dated Aug. 2009.
[No Author Listed], Product label of DECADRON® dexamethasone tablets, label for May 17, 2004 approval (NDA No. 011664), available at http://dailymed.nlm.nih.gov/dailvmed/druuInfo.cfm?id=2934 (last visitedDec. 22, 2008).
[No Author Listed], Product Label of LUMIGAN (bimatoprost ophthalmic solution) 0.03%, label for Jun. 22, 2006 approval of new or modified indication, available at http://www.fda.gov/cder/foi/label/2006/021275s013Ibl.pdf (last visited Sep. 9, 2008).
[No Author Listed], Product Label of TRAVATAN® (travoprost ophthalmic solution).0.004%, label for Feb. 13, 2003 approval of efficacy supplement with clinical data to support, available at http://www.fda.gov/cder/foUlabe1/2003/021257s0061bl.pdf (last visited Sep. 9, 2008).
[No Author Listed], Product Label of Xalatan® (latanoprost ophthalmic solution), label for Dec. 20, 2002 approval of new or modified indication, available at http://www.fda.gov/cder/foi/label/2002/20597SE1-010_Xalatan_lbl.pdf (last visited Sep. 9, 2008).
[No Author Listed], Prostaglandin analogues. Entrepreneur.com. 2008. Available at http://www.entrepreneur.com/tradejournals/article/print/166777491.html. 2 pages.
[No Author Listed], The American Heritage® Dictionary of the English Language, Fourth Edition, 2000, p. 1701 (with the definition of "steroid").
[No Author Listed], TRAVATAN™ (travoprost ophthalmic solution) 0.004% Sterile. NDA 21-257. Alcon Laboratories Inc. 2001. 7 pages.
Aihara et al., Incidence of deepening of the upper eyelid sulcus after switching from latanoprost to bimatoprost. Jpn J Ophthalmol Nov. 2011;55(6):600-4. Epub Sep. 28, 2011.
American Diabetes Association, Diagnosis and Classification of Diabetes Mellitus. Diabetes Care. Jan. 2004;27(1):S5-10.
American Diabetes Association, Standards of Medical Care in Diabetes—2008. Diabetes Care. Jan. 2008;31(1):512-54.
Anderson et al., High-carbohydrate, high-fiber diets for insulin-treated men with diabetes mellitus. Am J Clin Nutr. Nov. 1979;32(11):2312-21.
Asano et al., The PI 3-kinase/Akt signaling pathway is activated due to aberrant Pten expression and targets transcription factors NF-kappaB and c-Myc in pancreatic cancer cells. Oncogene. Nov. 11, 2004;23(53):8571-80. Erratum in: Oncogene. Jun. 16, 2005;24(26)4320.
Atkins et al., Randomized phase II study of multiple dose levels of CCI-779, a novel mammalian target of rapamycin kinase inhibitor, in patients with advanced refractory renal cell carcinoma. J Clin Oncol. Mar. 1, 2004;22(5):909-18.
Aydin et al., Recovery of orbital fat pad prolapses and deepening of the lid sulcus from topical bimatoprost therapy: 2 case reports and review of the literature. Cutan Ocul Toxicol. Sep. 2010;29(3):212-6.
Baer et al., Measurement of body composition of live rats by electromagnetic conductance. Physiol Behav. Jun. 1993;53(6):1195-9.
Bai et al., Nucleophosmin-anaplastic lymphoma kinase associated with anaplastic large-cell lymphoma activates the phosphatidylinositol 3-kinase/Akt antiapoptotic signaling pathway. Blood. Dec. 15, 2000;96(13):4319-27.
Berenson et al., Changes in weight, total fat, percent body fat, and central-to-peripheral fat ratio associated with injectable and oral contraceptive use. Am J Obstet Gynecol. Mar. 2009;200(3):329.e1-8.
Berge et al., Pharmaceutical salts. J Pharm Sci. Jan. 1977;66(1):1-19.
Bertin et al., Evaluation of dual-energy X-Ray absorptiometry for body-composition assessment in rats. J Nutr. Sep. 1998;128(9):1550-4.
Billottet et al., A selective inhibitor of the p110delta isoform of PI 3-kinase inhibits AML cell proliferation and survival and increases the cytotoxic effects of VP16. Oncogene. Oct. 26, 2006;25(50):6648-59. Epub May 15, 2006.

(56) References Cited

OTHER PUBLICATIONS

Bissler et al., Sirolimus for angiomyolipoma in tuberous sclerosis complex or lymphangioleiomyomatosis. N Engl J Med. Jan. 10, 2008;358(2):140-51.

Bos, ras oncogenes in human cancer: a review. Cancer Res. Sep. 1, 1989;49(17):4682-9.

Bowker et al., Increased cancer-related mortality for patients with type 2 diabetes who use sulfonylureas or insulin. Diabetes Care. Feb. 2006;29(2):254-8.

Byun et al., Frequent monoallelic deletion of PTEN and its reciprocal associatioin with PIK3CA amplification in gastric carcinoma. Int J Cancer. Apr. 10, 2003;104(3):318-27.

Cairns et al., Frequent inactivation of PTEN/MMAC1 in primary prostate cancer. Cancer Res. Nov. 15, 1997;57(22):4997-5000.

Cao et al., Addiction to elevated insulin-like growth factor I receptor and initial modulation of the AKT pathway define the responsiveness of rhabdomyosarcoma to the targeting antibody. Cancer Res. Oct. 1, 2008;68(19):8039-48.

Casimir et al., Preadipocyte differentiation blocked by prostanoid stimulation of prostanoid FP2 receptor in murine 3T3-L1 cells. Differentiation. Jul. 1996;60(4):203-10.

Casmir, Regulation of early preadipocyte differentiation: cAMP and prostaglandin F-2-alpha. ProQuest Dissertations and Theses; 1996; ProQuest Dissertations & Theses (PQDT). UMI No. 9634889. 162 pages.

Chapman et al., Glucocorticoid regulation of adipocyte differentiation: hormonal triggering of the developmental program and induction of a differentiation-dependent gene. J Cell Biol. Oct. 1985;101(4):1227-35.

Chen et al., Simultaneous determination and pharmacokinetic study of metformin and rosiglitazone in human plasma by HPLC-ESI-MS. J Chromatogr Sci. Feb. 2011;49(2):94-100.

Choi et al., In vitro study of antiadipogenic profile of latanoprost, travoprost, bimatoprost, and tafluprost in human orbital preadipocytes. J Ocul Pharmacol Ther. Apr. 2012;28(2):146-52. Epub Nov. 22, 2011. E-pub version.

Chun et al., Effects of deguelin on the phosphatidylinositol 3-kinase/Akt pathway and apoptosis in premalignant human bronchial epithelial cells. J Natl Cancer Inst. Feb. 19, 2003;95(4):291-302.

Culebras et al., Total Body Water and the Exchangeable Hydrogen. II. Total body water and the exchangeable hydrogen. II. A review of comparative data from animals based on isotope dilution and desiccation, with a report of new data from the rat. Am J Physiol. Jan. 1977;232(1):R60-5.

Dahms et al., Correlation of percent body fat with body specific gravity in rats. J Nutr. Feb. 1982;112(2):398-400.

Dal Col. et al., Distinct functional significance of Akt and mTOR constitutive activation in mantle cell lymphoma. Blood. May 15, 2008;111(10):5142-51. Epub Mar. 13, 2008.

Damodharan et al., Skin Permeation of Rosiglitazone from Transdermal Matrix Patches. Pharmaceutical Technology. 2010;34(5):56-72.

Database WPI, Week 201434. Thomson Scientific, London, GB; AN 2014-G76718 XP002729483 & KR 2014 0043562. Apr. 10, 2014. 3 pages.

Davidson et al., Weight control and risk factor reduction in obese subjects treated for 2 years with orlistat: a randomized controlled trial. JAMA. Jan. 20, 1999;281(3):235-42. Erratum in: JAMA Apr. 7, 1999;281(13):1174.

Dayan et al., Delivery System Design in Topically Applied Formulations: An Overview. In: Delivery System Handbook for Personal Care and Cosmetic Products. Rosen, ed. William Andrew. 2005:103-104.

Ettmayer et al., Lessons learned from marketed and investigational prodrugs. J Med Chem. May 6, 2004;47(10):2393-404.

Evans et al., Metformin and reduced risk of cancer in diabetic patients. BMJ. Jun. 4, 2005;330(7503):1304-5. Epub Apr. 22, 2005.

Fay et al., Energy homeostasis and cancer prevention: the AMP-activated protein kinase. Cancer Prev Res (Phila). Apr. 2009;2(4):301-9. Epub Mar. 31, 2009.

Ferner, Neurofibromatosis 1. Eur J Hum Genet. Feb. 2007;15(2):131-8. Epub Sep. 6, 2006.

Filippopoulos et al., Periorbital changes associated with topical bimatoprost. Ophthal Plast Reconstr Surg. 2008 Jul.-Aug. 2008;24(4):302-7.

Fletcher et al., Fibrinogen catabolism in patients with type II and type IV hyperlipidemia. Effect of dietary and clofibrate treatment on laboratory findings. Arteriosclerosis. May-Jun. 1981;1(3):202-9.

Fricke et al., The PGF(2alpha) receptor FP is lost in nevi and melanoma. Pigment Cell Melanoma Res. Feb. 2010;23(1):141-3. Epub Dec. 11, 2009.

Frisch et al., Carcass components at first estrus of rats on high-fat and low-fat diets: body water, protein, and fat. Proc Natl Acad Sci U S A. Jan. 1977;74(1):379-83.

Gaidhu et al., Chronic AMP-kinase activation with AICAR reduces adiposity by remodeling adipocyte metabolism and increasing leptin sensitivity. J Lipid Res. Sep. 2011;52(9):1702-11. Epub Jul. 7, 2011.

Gandelman et al., An eight-week trial investigating the efficacy and tolerability of atorvastatin for children and adolescents with heterozygous familial hypercholesterolemia. Pediatr Cardiol. Apr. 2011;32(4):433-41. Epub Jan. 23, 2011.

García-Rostán et al., Mutation of the PIK3CA gene in anaplastic thyroid cancer. Cancer Res. Nov. 15, 2005;65(22):10199-207.

Ghany et al., Diagnosis, management, and treatment of hepatitis C: an update. Hepatology. Apr. 2009;49(4):1335-74.

Ghosh et al., Feasibility of rosiglitazone maleate for transdermal delivery. Int J Pharma Res Innov. 2011;2:23-31.

Goel et al., Examination of mutations in BRAF, NRAS, and PTEN in primary cutaneous melanoma. J Invest Dermatol. Jan. 2006;126(1):154-60.

Goel et al., Frequent inactivation of PTEN by promoter hypermethylation in microsatellite instability-high sporadic colorectal cancers. Cancer Res. May 1, 2004;64(9):3014-21.

Gorin et al., Evidence for a role of protein kinase C in the stimulation of lipolysis by growth hormone and isoproterenol. Endocrinology. Jun. 1990;126(6):2973-82.

Gray et al., Mutation and expression analysis of the putative prostate tumour-suppressor gene Pten. Br J Cancer. Nov. 1998;78(10):1296-300.

Gregersen et al., Genetics of autoimmune diseases—disorders of immune homeostasis. Nature Rev Gen. Dec. 2006;7:917-28.

Gregoire et al., Understanding adipocyte differentiation. Physiol Rev. Jul. 1998;78(3):783-809.

Grosskreutz et al., Periorbital Fat Loss and Eyelid Sulcus Deepening after Bimatoprost Therapy. Final Program and Abstract Book, pp. 49 and 53, distributed at the American Glaucoma Society 2006 Annual Meeting, Mar. 2-5, 2006.

Grosskreutz et al., Periorbital Fat Loss and Eyelid Sulcus Deepening after Bimatoprost Therapy. Poster presented at The American Glaucoma Society 2006 Annual Meeting, Charleston, South Carolina. Mar. 2-5, 2006. 1 page.

Grosskreutz, Abstract submitted on Nov. 1, 2005 to the American Glaucoma Society for the American Glaucoma Society 2006 Annual Meeting. 1 page.

Guldberg et al., Disruption of the MMAC1/PTEN gene by deletion or mutation is a frequent event in malignant melanoma. Cancer Res. Sep. 1, 1997;57(17):3660-3.

Guo et al., The AMPK agonist AICAR inhibits the growth of EGFRvIII-expressing glioblastomas by inhibiting lipogenesis. Proc Natl Acad Sci U S A. Aug. 4, 2009;106(31):12932-7. Epub Jul. 22, 2009.

Gupta et al., Local recurrence in head and neck cancer: relationship to radiation resistance and signal transduction. Clin Cancer Res. Mar. 2002;8(3):885-92.

Gwinn et al., AMPK phosphorylation of raptor mediates a metabolic checkpoint. Mol Cell. Apr. 25, 2008;30(2):214-26.

Hardie, AMP-activated protein kinase: an energy sensor that regulates all aspects of cell function. Genes Dev. Sep. 15, 2011;25(18):1895-908. doi: 10.1101/gad.17420111.

Hata et al., Pharmacology and signaling of prostaglandin receptors: multiple roles in inflammation and immune modulation. Pharmacol Ther. Aug. 2004;103(2):147-66.

(56) References Cited

OTHER PUBLICATIONS

Heim, Transdermal Administration of Anti-inflammatory Medications in Sports Injuries: Use of Iontophoresis and Phonophoresis to Enhance Delivery. Int J Pharm Compd. Jan.-Feb. 2006;10(1):14-18.

Hickey et al., BCR-ABL regulates phosphatidylinositol 3-kinase-p110gamma transcription and activation and is required for proliferation and drug resistance. J Biol Chem. Feb. 3, 2006;281(5):2441-50. Epub Nov. 16, 2005.

Holmstrom et al., Analytic review of bimatoprost, latanoprost and travoprost in primary open angle glaucoma. Curr Med Res Opin. Nov. 2005;21(11):1875-83.

Hu et al., Expression and prognostic role of tumor suppressor gene PTEN/MMAC1/TEP1 in hepatocellular carcinoma. Cancer. Apr. 15, 2003;97(8):1929-40.

Husain et al., Acute effects of PGF2alpha on MMP-2 secretion from human ciliary muscle cells: a PKC- and ERK-dependent process. Invest Ophthalmol Vis Sci. May 2005;46(5):1706-13.

Ichhpujani et al., Comparison of human ocular distribution of bimatoprost and latanoprost. J Ocul Pharmacol Ther. Apr. 2012;28(2):134-45. doi: 10.1089/jop.2011.0097. Epub Dec. 2, 2011.

Inoue et al., Deepening of the Upper Eyelid Sulcus Caused by 5 Types of Prostaglandin Analogs. J Glaucoma. Aug. 29, 2012. [Epub ahead of print] E-pub version. 6 pages.

Jabbour et al., A positive feedback loop that regulates cyclooxygenase-2 expression and prostaglandin F2alpha synthesis via the F-series-prostanoid receptor and extracellular signal-regulated kinase 1/2 signaling pathway. Endocrinology. Nov. 2005;146(11):4657-64. Epub Aug. 4, 2005.

Jacob et al., Weight gain in type 2 diabetes mellitus. Diabetes Obes Metab. May 2007;9(3):386-93.

Johannessen et al., TORC1 is essential for NF1-associated malignancies. Curr Biol. Jan. 8, 2008;18(1):56-62. Epub Dec. 27, 2007.

Jonas et al., Drug Class Review: Newer diabetes medications, TZDs, and combinations. Final Original Report. Drug Effectiveness Review Project. Feb. 2011.

Kao, In Vitro Assessment of Dermal Absorption. In: Dermal and Ocular Toxicology: Fundamentals and Methods. Hobson, ed. CRC Press. 1991:267, 272-273.

Karlsson et al., cDNA cloning, tissue distribution, and identification of the catalytic triad of monoglyceride lipase. Evolutionary relationship to esterases, lysophospholipases, and haloperoxidases. J Biol Chem. Oct. 24, 1997;272(43):27218-23.

Kayikcioglu et al., Semicircular lipoatrophy after intragluteal injection of benzathine penicillin. J Pediatr. Jul. 1996;129(1):166-7.

Kim et al., The increase in abdominal subcutaneous fat depot is an independent factor to determine the glycemic control after rosiglitazone treatment. Eur J Endocrinol. Aug. 2007;157(2):167-74.

Kisfalvi et al., Metformin disrupts crosstalk between G protein-coupled receptor and insulin receptor signaling systems and inhibits pancreatic cancer growth. Cancer Res. Aug. 15, 2009;69(16):6539-45.

Klein et al., Absence of an effect of liposuction on insulin action and risk factors for coronary heart disease. N Engl J Med. Jun. 17, 2004;350(25):2549-57.

Klein et al., Non-invasive cryolipolysis for subcutaneous fat reduction does not affect serum lipid levels or liver function tests. Lasers Surg Med. Dec. 2009;41(10):785-90.

Kokubo et al., Reduction of PTEN protein and loss of epidermal growth factor receptor gene mutation in lung cancer with natural resistance to gefitinib (IRESSA). Br J Cancer. May 9, 2005;92(9):1711-9.

Kudchodkar et al., AMPK-mediated inhibition of mTOR kinase is circumvented during immediate-early times of human cytomegalovirus infection. J Virol. Apr. 2007;81(7):3649-51. Epub Jan. 10, 2007.

Kuenzli et al., Effect of topical PPARbeta/delta and PPARgamma agonists on plaque psoriasis. A pilot study. Dermatology. 2003;206(3):252-6.

Kumar et al., Lecithin organogels as a potential phospholipid-structured system for topical drug delivery: a review. AAPS PharmSciTech. 2005 Oct. 6, 2005;6(2):E298-310.

Künnecke et al., Quantitative body composition analysis in awake mice and rats by magnetic resonance relaxometry. Obes Res. Oct. 2004;12(10):1604-15.

Lee et al., Chemopreventive effects of deguelin, a novel Akt inhibitor, on tobacco-induced lung tumorigenesis. J Natl Cancer Inst. Nov. 16, 2005;97(22):1695-9.

Lee et al., PIK3CA gene is frequently mutated in breast carcinomas and hepatocellular carcinomas. Oncogene. Feb. 17, 2005;24(8):1477-80.

Lepak et al., Inhibition of adipose differentiation by 9 alpha, 11 beta-prostaglandin F2 alpha. Prostaglandins. Dec. 1993;46(6):511-7.

Lepak et al., Prostaglandin F2 alpha stimulates transforming growth factor-alpha expression in adipocyte precursors. Endocrinology. Aug. 1995;136(8):3222-9.

Lesser et al., Modification of subcutaneous adipose tissue by a methylxanthine formulation: a double-blind controlled study. Dermatol Surg. Jun. 1999;25(6):455-62.

Liszka et al., Effect of lipectomy on growth and development of hyperinsulinemia and hyperlipidemia in the Zucker rat. Plast Reconstr Surg. Sep. 1998;102(4):1122-7.

Liu et al., Postaglandin F2alpha inhibits adipocyte differentiation via a G alpha q-calcium-calcineurin-dependent signaling pathway. J Cell Biochem. Jan. 1, 2007;100(1):161-73.

Löffler et al., Adipose tissue development: the role of precursor cells and adipogenic factors. Part II: The regulation of the adipogenic conversion by hormones and serum factors. Klin Wochenschr. Sep. 1, 1987;65(17):812-7.

Lu et al., Loss of tuberous sclerosis complex-2 function and activation of mammalian target of rapamycin signaling in endometrial carcinoma. Clin Cancer Res. May 1, 2008;14(9):2543-50.

Lu et al., PI3K-Akt signaling is involved in the regulation of p21(WAF/CIP) expression and androgen-independent growth in prostate cancer cells. Int J Oncol. Jan. 2006;28(1):245-51.

Majumder et al., Akt-regulated pathways in prostate cancer. Oncogene. Nov. 14, 2005;24(50):7465-74.

Massion et al., Early involvement of the phosphatidylinositol 3-kinase/Akt pathway in hung cancer progression. Am J Respir Crit Care Med. Nov. 15, 2004;170(10):1088-94. Epub Aug. 18, 2004.

Maxey et al., The hydrolysis of bimatoprost in corneal tissue generates a potent prostanoid FP receptor agonist. Sury Ophthalmol. Aug. 2002;47 Suppl 1:S34-40.

Miller et al., The mechanism of inhibition of 3T3-L1 preadipocyte differentiation by prostaglandin F2alpha. Endocrinology. Dec. 1996;137(12):5641-50.

Mohammed et al., Long-term effects of large-volume liposuction on metabolic risk factors for coronary heart disease. Obesity (Silver Spring). Dec. 2008;16(12):2648-51. doi: 10.1038/oby.2008.418. Epub Jun. 1, 2009. 8 pages.

Morissette et al., High-throughput crystallization: polymorphs, salts, co-crystals and solvates of pharmaceutical solids. Adv Drug Deliv Rev. Feb. 23, 2004;56(3):275-300.

Morley, Orexigenic and anabolic agents. Clin Geriatr Med. Nov. 2002;18(4):853-66. Review.

Motzer et al., Phase I/II trial of temsirolimus combined with interferon alfa for advanced renal cell carcinoma. J Clin Oncol. Sep. 1, 2007;25(25):3958-64.

Mulholland et al., PTEN and GSK3beta: key regulators of progression to androgen-independent prostate cancer. Oncogene. Jan. 19, 2006;25(3):329-37.

Nafz et al., Interference with energy metabolism by 5-aminoimidazole-4-carboxamide-1-beta-D-ribofuranoside induces HPV suppression in cervical carcinoma cells and apoptosis in the absence of LKB1. Biochem J. May 1, 2007;403(3):501-10.

Nagata et al., PTEN activation contributes to tumor inhibition by trastuzumab, and loss of PTEN predicts trastuzumab resistance in patients. Cancer Cell. Aug. 2004;6(2):117-27.

Nahta et al., Mechanisms of disease: understanding resistance to HER2-targeted therapy in human breast cancer. Nat Clin Pract Oncol. May 2006;3(5):269-80.

(56) References Cited

OTHER PUBLICATIONS

Nakajima et al., New fluoroprostaglandin F(2alpha) derivatives with prostanoid FP-receptor agonistic activity as potent ocular-hypotensive agents. Biol Pharm Bull. Dec. 2003;26(12):1691-5.
Nakakura et al., Latanoprost therapy after sunken eyes caused by travoprost or bimatoprost. Optom Vis Sci. Sep. 2011;88(9):1140-4.
Nassif et al., PTEN mutations are common in sporadic microsatellite stable colorectal cancer. Oncogene. Jan. 15, 2004;23(2):617-28.
Nozue et al., Effects of statin on small dense low-density lipoprotein cholesterol and remnant-like particle cholesterol in heterozygous familial hypercholesterolemia. J Atheroscler Thromb. Jun. 2008;15(3):146-53.
Obata et al., Frequent PTEN/MMAC mutations in endometrioid but not serous or mucinous epithelial ovarian tumors. Cancer Res. May 15, 1998;58(10):2095-7.
Ota et al., The IOP-lowering effects and mechanism of action of tafluprost in prostanoid receptor-deficient mice. Br J Ophthalmol May 2007;91(5):673-6. Epub Nov. 23, 2006.
Pantoja et al., Glucocorticoid signaling defines a novel commitment state during adipogenesis in vitro. Mol Biol Cell. Oct. 2008;19(10):4032-41. Epub Jul. 23, 2008.
Pao et al., KRAS mutations and primary resistance of hung adenocarcinomas to gefitinib or erlotinib. PLoS Med. Jan. 2005;2(1):e17. Epub Jan. 25, 2005.
Park et al., Changes to upper eyelid orbital fat from use of topical bimatoprost, travoprost, and latanoprost. Jpn J Ophthalmol. Jan. 2011;55(1):22-7. Epub Feb. 18, 2011.
Paula et al., Periorbital Fat Loss and Eyelid Sulcus Deepening after Bimatoprost Therapy. Manuscript submitted to Archives of Ophthalmology, Oct. 21, 2005 (10 pages).
Peplinski et al., Deepening of lid sulcus from topical bimatoprost therapy. Optom Vis Sci. Aug. 2004;81(8):574-7.
Porter et al., Abdominal subcutaneous adipose tissue: a protective fat depot? Diabetes Care. Jun. 2009;32(6):1068-75. doi: 10.2337/dc08-2280. Epub Feb. 24, 2009.
Rattan et al., 5-Aminoimidazole-4-carboxamide-1-beta-D-ribofuranoside inhibits cancer cell proliferation in vitro and in vivo via AMP-activated protein kinase. J Biol Chem. Nov. 25, 2005;280(47):39582-93. Epub Sep. 21, 2005.
Reginato et al., Prostaglandins promote and block adipogenesis through opposing effects on peroxisome proliferator-activated receptor gamma J Biol Chem. Jan. 23, 1998;273(4):1855-8.
Robin, An accurate comparison of bimatoprost's efficacy and adverse effects. Arch Ophthalmol. Jul. 2002;120(7):999-1000; author reply 1000.
Ross, Does exercise without weight loss improve insulin sensitivity? Diabetes Care. Mar. 2003;26(3):944-5.
Rundle, Drug That Lengthens Eyelashes Sets Off Flutter. Wall Street J. Nov. 19, 2007 (2 pages).
Sales et al., Expression, localization, and signaling of prostaglandin F2 alpha receptor in human endometrial adenocarcinoma: regulation of proliferation by activation of the epidermal growth factor receptor and mitogen-activated protein kinase signaling pathways. J Clin Endocrinol Metab. Feb. 2004;89(2):986-93.
Sales et al., F-prostanoid receptor regulation of fibroblast growth factor 2 signaling in endometrial adenocarcinoma cells. Endocrinology. Aug. 2007;148(8):3635-44. Epub May 3, 2007.
Schiwek et al., Glucocorticoid hormones contribute to the adipogenic activity of human serum. Endocrinology. Feb. 1987;120(2):469-74. Abstract only.
Selliah et al., AL-12182, a novel 11-oxa prostaglandin analog with topical ocular hypotensive activity in the monkey. Bioorg Med Chem Lett. Sep. 6, 2004;14(17):4525-8.
Serrero et al., Prostaglandin F2 alpha inhibits epidermal growth factor binding to cellular receptors on adipocyte precursors in primary culture. Biochem Biophys Res Commun. Jul. 26, 1995;212(3):1125-32.
Serrero et al., Prostaglandin F2 alpha inhibits the differentiation of adipocyte precursors in primary culture. Biochem Biophys Res Commun. Mar. 16, 1992;183(2):438-42.
Serrero et al., Prostaglandin F2alpha receptor (FP receptor) agonists are potent adipose differentiation inhibitors for primary culture of adipocyte precursors in defined medium. Biochem Biophys Res Commun. Apr. 7, 1997;233(1):200-2.
Shah et al., A cross-sectional survey of the association between bilateral topical prostaglandin analogue use and ocular adnexal features. PLoS One. May 1, 2013;8(5):e61638. doi: 10.1371/journal.pone.0061638. Print 2013. 7 pages.
Sharif et al., Agonist activity of bimatoprost, travoprost, latanoprost, unoprostone isopropyl ester and other prostaglandin analogs at the cloned human ciliary body FP prostaglandin receptor. J Ocul Pharmacol Ther. Aug. 2002;18(4):313-24.
Shi et al., A glucocorticoid-induced leucine-zipper protein, GILZ, inhibits adipogenesis of mesenchymal cells. EMBO Rep. Apr. 2003;4(4):374-80. Epub Mar. 14, 2003.
Shugart et al., Dexamethasone signaling is required to establish the postmitotic state of adipocyte development. Cell Growth Differ. Oct. 1997;8(10):1091-8.
Singh et al., Local deep tissue penetration of compounds after dermal application: structure-tissue penetration relationships. J Pharmacol Exp Ther. Nov. 1996;279(2):908-17.
Sjööquist et al., The pharmacokinetics of a new antiglaucoma drug, latanoprost, in the rabbit. Drug Metab Dispos. Aug. 1998;26(8):745-54.
Sjöquist et al., Ocular and systemic pharmacokinetics of latanoprost in humans. Surv Ophthalmol. 2002 Aug. ;47 Suppl 1:S6-12.
Skorski et al., Transformation of hematopoietic cells by BCR/ABL requires activation of a PI-3k/Akt-dependent pathway. Embo J. Oct. 15, 1997;16(20):6151-61.
Slama et al., Effect of pioglitazone on HIV-1-related lipodystrophy: a randomized double-blind placebo-controlled trial (ANRS 113). Antivir Ther. 2008;13(1):67-76.
Smith et al., Effect of pioglitazone on body composition and energy expenditure: a randomized controlled trial. Metabolism. Jan. 2005;54(1):24-32.
Stella, Prodrugs as therapeutics. Expert Opin Ther Patents. 2004;14(3):277-80.
Sujobert et al., Essential role for the p110delta isoform in phosphoinositide 3-kinase activation and cell proliferation in acute myeloid leukemia. Blood. Aug. 1, 2005;106(3):1063-6. Epub Apr. 19, 2005.
Swinnen et al., Mimicry of a cellular low energy status blocks tumor cell anabolism and suppresses the malignant phenotype. Cancer Res. Mar. 15, 2005;65(6):2441-8.
Tamburini et al., Constitutive phosphoinositide 3-kinase/Akt activation represents a favorable prognostic factor in de novo acute myelogenous leukemia patients. Blood. Aug. 1, 2007;110(3):1025-8. Epub Apr. 10, 2007.
Tappeiner et al., [Orbital fat atrophy in glaucoma patients treated with topical bimatoprost—can bimatoprost cause enophthalmos?]. Klin Monbl Augenheilkd. May 2008;225(5):443-5. English abstract only.
Testa, Prodrug research: futile or fertile? Biochem Pharmacol. Dec. 1, 2004;68(11):2097-106.
Tong et al., Heightened expression of cyclooxygenase-2 and peroxisome proliferator-activated receptor-delta in human endometrial adenocarcinoma. Neoplasia. Nov.-Dec. 2000;2(6):483-90.
Tornqvist et al., Purification and some properties of a monoacylglycerol-hydrolyzing enzyme of rat adipose tissue. J Biol Chem. Feb. 10, 1976;251(3):813-9.
Tsao et al., Relative reciprocity of NRAS and PTEN/MMAC1 alterations in cutaneous melanoma cell lines. Cancer Res. Apr. 1, 2000;60(7):1800-4.
Tsuboi et al., Prostanoid EP4 receptor is involved in suppression of 3T3-L1 adipocyte differentiation. Biochem Biophys Res Commun. Sep. 24, 2004;322(3):1066-72.
Uddin et al., Role of phosphatidylinositol 3'-kinase/AKT pathway in diffuse large B-cell lymphoma survival. Blood. Dec. 15, 2006;108(13):4178-86. Epub Aug. 31, 2006.
Vippagunta et al., Crystalline solids. Adv Drug Deliv Rev. May 16, 2001;48(1):3-26.
Wagstaff et al., Rosiglitazone: a review of its use in the management of type 2 diabetes mellitus. Drugs. 2002;62(12)1805-37.

(56) References Cited

OTHER PUBLICATIONS

Wan et al., CCI-779 inhibits rhabdomyosarcoma xenograft growth by an antiangiogenic mechanism linked to the targeting of mTOR/Hif-1alpha/VEGF signaling. Neoplasia. May 2006;8(5):394-401.

Wang et al., AMP-activated protein kinase and cancer. Acta Physiol (Oxf). May 2009;196(1):55-63. Feb. 25, 2009.

Wang et al., Homozygous deletion of the PTEN tumor suppressor gene in a subset of prostate adenocarcinomas. Clin Cancer Res. Mar. 1998;4(3):811-5.

Wang et al., PTEN deletion leads to the expansion of a prostatic sstem/progenitor cell subpopulation and tumor initiation. Proc Natl Acad Sci U S A. Jan. 31, 2006;103(5):1480-5. Epub Jan. 23, 2006.

Weber et al., Subcutaneous lipectomy causes a metabolic syndrome in hamsters. Am J Physiol Regul Integr Comp Physiol. Sep. 2000;279(3):R936-43.

Whang et al., Inactivation of the tumor suppressor PTEN/MMAC1 in advanced human prostate cancer through loss of expression. Proc Natl Acad Sci U S A. Apr. 28, 1998;95(9):5246-50.

Whiteman et al., Nuclear PTEN expression and clinicopathologic features in a population-based series of primary cutaneous melanoma. Int J Cancer. May 1, 2002;99(1):63-7.

Wilen et al., Strategies in Optical Resolution. Tetrahedron. 1977;33:2725-36.

Wilen, Tables of Resolving Agents and Optical Resolutions. Eliel, Ed. University of Notre Dame Press. Notre Dame, IN. 1972:268-90.

Wolff et al., Burger's Medicinal Chemistry and Drug Discovery. Fifth Edition. vol. I: Principles and Practice. 1994:975-7.

Woodward et al., The pharmacology of bimatoprost (Lumigan™). Sury Ophthalmol. May 2001;45 Suppl 4:S337-45.

Wu et al., Uncommon mutation, but common amplifications, of the PIK3CA gene in thyroid tumors. J Clin Endocrinol Metab. Aug. 2005;90(8):4688-93. Epub May 31, 2005.

Xin et al., Progression of prostate cancer by synergy of AKT with genotropic and nongenotropic actions of the androgen receptor. Proc Natl Acad Sci U S A. May 16, 2006;103(20):7789-94. Epub May 8, 2006.

Yam et al., Bilateral deepening of upper lid sulcus from topical bimatoprost therapy. J Ocul Pharmacol Ther. Oct. 2009;25(5):471-2.

Zakikhani et al., Metformin is an AMP kinase-dependent growth inhibitor for breast cancer cells. Cancer Res. Nov. 1, 2006;66(21):10269-73. Epub Oct. 23, 2006.

Zateyschikov, Thiazolidinediones and heart failure. Zhurnal Farmateka. 2005;3(99):1-6. http://www.pharmateca.ru/ru/archive/article/5901 [last accessed Apr. 16, 2014].

Ziegler, FDA Approves Latisse Eyelash Growth Product. Last accessed Jul. 24, 2012 at 3 http://voices.yahoo.com/fda-approves-latisse-eyelash-growth-product-3520905.html?cat=39. 3 pages.

Extended European Search Report, dated Jul. 10, 2015, in connection with Application No. EP12859422.3.

International Preliminary Report on Patentability, dated Nov. 19, 2015, in connection with Application No. PCT/US2014/037512.

International Search Report and Written Opinion, dated Aug. 12, 2015, in connection with Application No. PCT/US2015/037323.

Blank et al., Mechanism of percutaneous absorption. 3. The effect of temperature on the transport of non-electrolytes across the skin. J Invest Dermatol. Dec. 1967;49(6):582-9.

Hellberg et al., The hydrolysis of the prostaglandin analog prodrug bimatoprost to 17-phenyl-trinor PGF2alpha by human and rabbit ocular tissue. J Ocul Pharmacol Ther. Apr. 2003;19(2):97-103.

Izumi et al., Short-term effects of topical tafluprost on retinal blood flow in cats. J Ocul Pharmacol Ther. Oct. 2008;24(5):521-6. doi: 10.1089/jop.2007.0065.

Woodward et al., Prostamides (prostaglandin-ethanolamides) and their pharmacology. Br J Pharmacol. Feb. 2008;153(3):410-9. Epub Aug. 27, 2007.

Extended European Search Report, dated Dec. 6, 2016, in connection with Application No. EP 16177742.0.

Park et al., In vitro skin penetration and pharmacodynamic evaluation of prostaglandin E1 ethyl ester, a vasoactive prodrug of prostaglandin E1, formulated into alcoholic hydrogels. Pharmazie. Nov. 2006;61(11):933-7.

Second Written Opinion, dated Jun. 17, 2016, in connection with Application No. PCT/US2015/037323.

U.S. Appl. No. 15/243,641, filed Aug. 22, 2016, Grosskreutz et al. PCT/US2015/037323, dated Jun. 17, 2016, Second Written Opinion.

\* cited by examiner

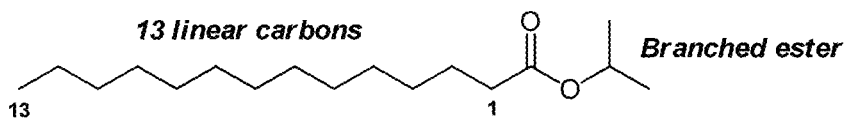
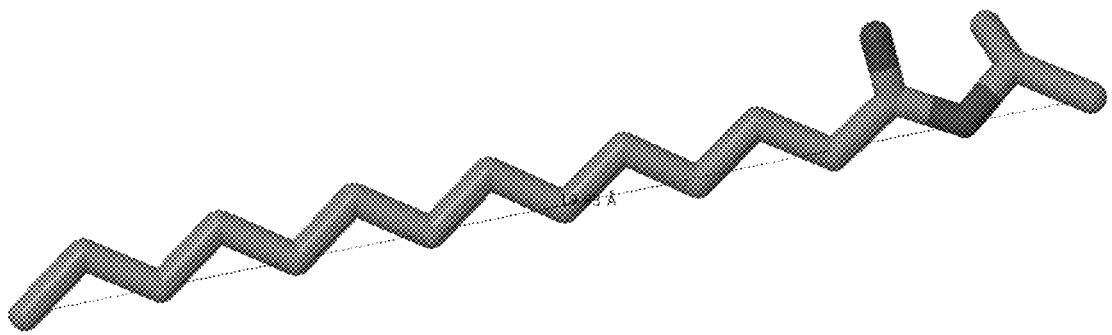
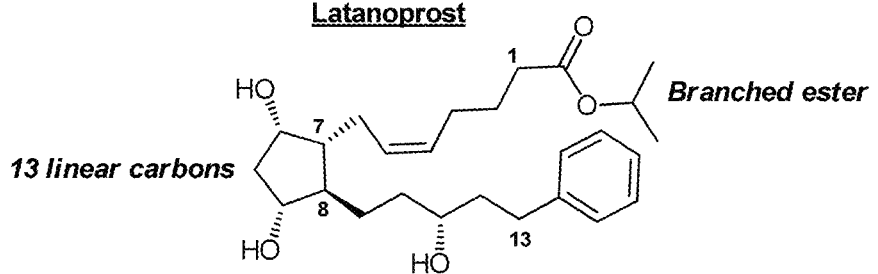
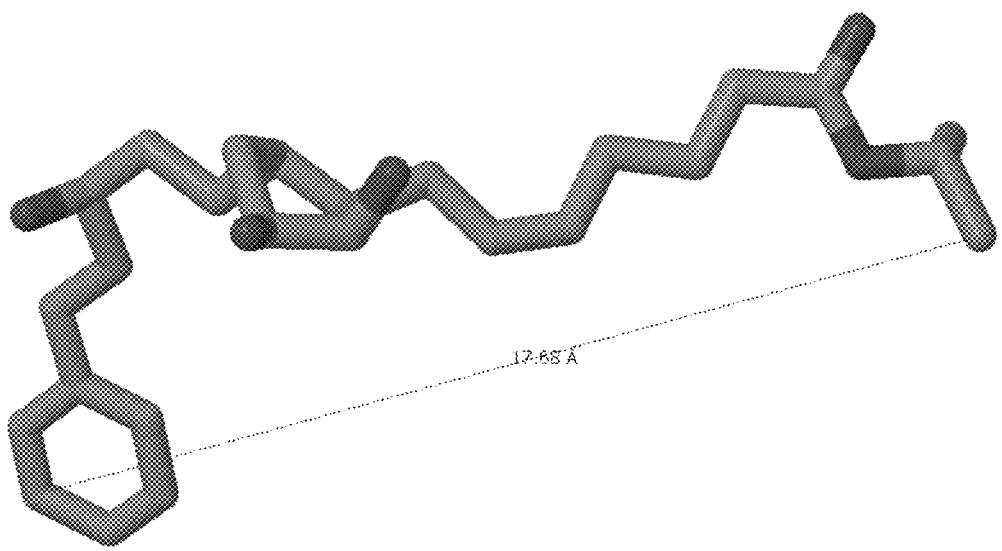

US 9,849,179 B2

METHODS FOR TOPICAL DELIVERY OF PROSTAGLANDINS TO SUBCUTANEOUS FAT

RELATED APPLICATIONS

This application is a continuation of and claims priority under 35 U.S.C. §120 to U.S. application, U.S. Ser. No. 14/575,873, filed Dec. 18, 2014, which claims priority under 35 U.S.C. §365(c) to and is a continuation of international PCT Application, PCT/US2014/037512, filed May 9, 2014, which claims priority under 35 U.S.C. §119(e) to U.S. provisional patent application, U.S. Ser. No. 61/822,139, filed May 10, 2013, each of which is incorporated herein by reference.

FIELD OF THE INVENTION

The present invention relates to methods and compositions for topically delivering a therapeutically effective amount of a prostaglandin FP receptor agonist (a PFPRA compound) to adipose tissue under the skin. The therapeutic effect is, for example, reduction of excess fat under the skin, for example, the skin of the face, eyelids, neck, chin, submental region, limbs, breast, abdomen, hips, etc. More specifically, the invention relates to new compositions comprising a PFPRA compound and a fatty acid ester (e.g., isopropyl myristate), optionally further comprising an ointment base such as a hydrocarbon base (e.g., petroleum jelly), and/or optionally further comprising an organic alcohol (e.g., propylene glycol). The invention further relates to methods comprising applying the aforementioned composition(s) to the skin. The invention further relates to processes for manufacturing the aforementioned composition(s).

Experimentally, in comparison to a wide array of other compositions tested, the compositions disclosed herein demonstrate exceptional and surprising efficiency in delivering certain PFPRA compounds across skin in vitro, in delivering a therapeutically effective amount to fat below the skin in vivo, and/or in reducing subcutaneous fat in vivo. In theory, this surprising efficiency may owe to the similar structure and polarity between the PFPRA compound (e.g., latanoprost) and the fatty acid ester (e.g., isopropyl myristate), as described herein. The compositions are non-irritating, well-tolerated, and aesthetically pleasing. As a further advantage, they are considered suitable for application to the face, the eyelid, and/or periorbital skin. Furthermore, the compositions are stable and can be readily manufactured, where necessary in sterile form.

BACKGROUND OF THE INVENTION

Excess body fat is an important cause of human disease, disability, and cosmetic disturbance. For many people excess body fat is also a source of psychosocial distress and reduced self-esteem.

Excess body fat may be diffuse or concentrated on particular portion(s) of the body. Of particular importance is excess body fat of the face, for example, of the eyelids, chin, or jowls. Other important sites of excess body fat can include, for example, the arms, abdomen, buttocks, hips, chest, thighs, and neck. Excess body fat can also involve excessive breast tissue on a woman or on a man, i.e., gynecomastia. Excess body fat can be located within or near the eyelids, and topical treatment of such fat requires a composition that is safe for application near the eyes, i.e. an ophthalmic and/or ophthalmically compatible formulation.

Local accumulations of body fat may result from constitutional factors, disease, hormonal status, or as side effects of medication or other substances. Even in the absence of disease, cosmetic considerations apply to individuals who nevertheless perceive an excess of fat and wish to have it corrected. For example, excess submental fat, commonly known as "double chin," is not considered a disease; however, people with excess submental fat often appear less attractive and less youthful, and can have lower self-esteem as a result. Likewise, an individual may have excess subcutaneous fat on the anterior abdomen, excess subcutaneous fat on the oblique abdomen, e.g. above the iliac crests ("love handles"), excess chest fat, excess breast fat, excess buttocks fat, excess hip fat, excess thigh fat, excess leg fat, excess upper arm fat, excess check fat, excess neck fat, etc.

A number of medical conditions are considered to be causes of excess body fat. Examples include drug-induced obesity, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, and leptin deficiency or resistance. Disfiguring excess regional fat deposits, for example excess dorsocervical fat, may be found in conditions such as HIV lipodystrophy, Cushing syndrome and pseudo-Cushing syndrome (i.e., characteristic syndrome of excess body fat and other findings due to excessive endogenous or exogenous corticosteroid levels), other acquired lipodystrophies, familial lipodystrophies, lipoma, lipomatosis, and Madelung disease.

Medications known to cause excess body fat include cortisol and analogs, other corticosteroids, megace, sulfonylureas, antiretrovirals, tricyclic antidepressants, monoamine oxidase inhibitors, selective serotonin reuptake inhibitors, oral contraceptives, insulin, risperidone, clozapine, and thiazolidinediones.

Changes in hormonal status, including physiologic changes such as pregnancy or menopause, may result in excess body fat in a subject. Smoking cessation commonly leads to weight gain and excess body fat. Trauma may favor the accumulation of excess body fat by virtue of immobility or disuse of an extremity. Similar problems may affect a subject who is immobilized, for example due to an injury. Some tumors, for example lipomas and liposarcomas, are characterized by local collections of fat cells. Lipomatosis is any condition characterized by the formation of multiple lipomas on the body, e.g., familial multiple lipomatosis, adiposis dolorosis (Dercum's disease), pelvic lipomatosis, etc.

Even in the absence of underlying pathology, an individual may have cosmetic concerns about local or diffuse deposits of body fat. These can usually be attributed to constitutional or hereditary factors, developmental history, age, gender, diet, alcohol use, or other components of lifestyle. Individuals in such circumstances commonly wish to reduce the amount of fat on the face, eyelids, chin, arms, neck, abdomen, chest, breast, buttocks, hips, thighs, and/or legs. In some cases a local excess of fat can be due to fat prolapse, displacement, and/or migration, as in age-related orbital fat prolapse or descent of malar fat pads. Grave's ophthalmopathy (thyroid-related eye disease) is a condition that can be treated by reducing the volume of orbital fat.

A number of methods have been developed to reduce or remove excess body fat. It is helpful to classify these methods as extractive, metabolic, or adipolytic. Extractive methods, such as lipoplasty (e.g., liposuction) or local excision, are methods whereby fat is physically removed from areas of interest. Such methods are costly and may involve scars, postsurgical deformity or regression, discomfort, infection, and other adverse reactions.

In contrast to extractive methods, metabolic methods, which include systemic medications, nutritional supplements, devices, and exercise or other body treatment, seek to modify the subject's metabolism (e.g., whether caloric consumption, expenditure, or both) such that the subject incurs a net loss of fat. A disadvantage is that these methods typically cannot be directed to a particular part of the body. Another drawback is potential concomitant loss of water, carbohydrates, protein, vitamins, minerals, and other nutrients. Furthermore, traditional diet medications may have undesired side effects, for example palpitations, tremor, insomnia, and/or irritability in a subject who uses stimulants as appetite suppressants. Despite salubrious value, the traditional metabolic methods of diet and exercise are not practical for everybody.

Adipolytic methods aim to cause breakdown of adipocytes and/or their lipid contents. For example, fat deposits can be reduced by exposure to cold temperature or to deoxycholate, a solubilizer that lyses cell membranes and results in local necrosis. Drawbacks of these methods can include poor discrimination between adipose and other nearby tissues, barriers to delivery that require hypodermic needles or special equipment, and adverse effects such as necrosis, inflammation, and pain.

Compounds of the prostaglandin FP receptor agonist (PFPRA compound) class, e.g., latanoprost and tafluprost, can be administered to the skin to locally reduce adipose tissue under the skin, i.e., subcutaneous fat. See, e.g., U.S. Pat. No. 8,426,471 and U.S. Publication No. 2010/0234466, incorporated herein by reference. Developing topical delivery of the PFPRA compound poses significant challenges, since delivery to subcutaneous fat comprises delivery across the stratum corneum, epidermis, dermis, and dermal microcirculation, and into the fat below.

For example, the skin, in particular the stratum corneum, presents a formidable physical barrier to drug penetration. See, e.g., Dayan N, Delivery System Design in Topically Applied Formulations: An Overview, in Rosen M, Delivery System Handbook for Personal Care and Cosmetic Products, William Andrew, 2005, pp. 103-104. For any particular drug, the formulation must be selected empirically. The formulation must be physically and chemically compatible with the drug.

Furthermore, provided that a formulation enables a drug to cross the skin, to reach the subcutaneous fat it must also circumvent what is known as the "sink condition" of the dermal circulation. See, e.g., Dayan N, Delivery System Design in Topically Applied Formulations: An Overview, in Rosen M, Delivery System Handbook for Personal Care and Cosmetic Products, William Andrew, 2005, pp. 103-104; Kao J, In Vitro Assessment of Dermal Absorption, in Hobson D W, Dermal and Ocular Toxicology: Fundamentals and Methods, CRC Press, 1991, pp. 272-273. Because the dermis is invested by a network of capillaries with rapid blood flow, for any solute (e.g., drug) that penetrates the dermis, a wide concentration gradient is created between the skin and bloodstream. Thus, there is a strong tendency for drugs that penetrate into the dermis to diffuse rapidly down this gradient into the bloodstream. This sink phenomenon favors systemic delivery (e.g., to the bloodstream, as with a nicotine patch), but undermines attempts at local delivery (e.g., to subcutaneous fat, as in the present invention). No method of reasoning or prediction is available in the art to suggest which formulations, if any, can circumvent the sink condition. Therefore, the artisan must search for such formulations empirically, and without prior knowledge that such formulation even exists.

The formulation must also have a favorable systemic drug exposure profile, e.g., that avoids excessive levels of drug in the bloodstream. This requirement is rendered more difficult by the sink condition.

Additionally, the formulation should deliver the active ingredient with reasonable efficiency. One measure of efficiency is the ability to minimize the concentration of active ingredient in the finished product and still maintain the desired therapeutic effect. This has implications for manufacturability, cost of goods, and local safety and tolerability. Another measure of efficiency is the ability to minimize the dose frequency and still maintain the desired therapeutic effect, which has implications for patient convenience and product marketability.

As well, the formulation must cause little or no skin irritation. If applied to skin near the eye, e.g., the eyelid, the formulation is considered an ophthalmic formulation. Generally, an ophthalmic formulation must be sterile, e.g., according to Chapter <71> of the U.S. Pharmacopeia. Preferably, an ophthalmic formulation must also be free or essentially free of bacterial endotoxin, e.g. according to Chapter <85> of the U.S. Pharmacopeia, e.g., an endotoxin level of <10 EU (endotoxin units) per gram of composition. If applied to skin near the eye, the formulation must be ophthalmically compatible, i.e, the formulation must not cause clinically significant eye irritation, and must not be toxic to the eye, e.g., the ocular surface, e.g. the cornea. Irritation potential and ocular toxicity are studied empirically by standard preclinical models, or in human trials. Although the skin or eye irritation potential of individual inactive ingredients is generally known, combinations of inactive and active ingredients can cause unexpected irritation, which must be tested empirically.

Furthermore, the formulation must possess other qualities necessary to make a topical formulation and market it to consumers: ease of manufacture, physical and chemical stability, and commercially acceptable appearance, odor, and tactile qualities.

Therefore, there is a need for new compositions for topically delivering a PFPRA compound to adipose tissue under the skin.

SUMMARY OF THE INVENTION

It has now been discovered experimentally that certain topical compositions comprising a PFPRA compound (e.g., latanoprost or tafluprost) and certain fatty acid esters (e.g., isopropyl myristate) provide exceptionally efficient delivery of the compound and its active metabolite into subcutaneous fat, and thus have particular uses and advantages, as described herein. In theory, this efficiency may owe to the similar structure and polarity between the PFPRA compound (e.g., latanoprost or tafluprost) and the fatty acid ester (e.g., isopropyl myristate), as described herein.

Thus, in one aspect, provided is a composition useful in the reduction of subcutaneous fat comprising a PFPRA compound, e.g. latanoprost or tafluprost, and a fatty acid ester, e.g., isopropyl myristate. In certain embodiments, the concentration of the PFPRA compound in the composition is between about 0.0001 percent to about 1 percent by weight, as a proportion of the total weight of the composition, e.g., between about 0.05 percent and about 0.5 percent by weight, or between about 0.01 percent and about 0.1 percent by weight of the final composition. In some embodiments, the final concentration of the fatty acid ester (e.g., isopropyl myristate) is between about 1 percent to about 20 percent by weight, e.g., between about 1 percent and about 10 percent by weight of the composition. In certain embodiments, the composition further comprises an ointment base, e.g., a hydrocarbon base such as petroleum jelly. In some embodiments, the final concentration of the ointment base is between about 50 percent and about 99 percent by weight, e.g., between about 70 percent and about 99 percent by weight, of the total weight of the composition. In some embodiments, the composition further comprises an organic alcohol (e.g., propylene glycol). In some embodiments, the final concentration of the organic alcohol is between about 5 percent and about 50 percent by weight, e.g., between about 5 percent and about 20 percent by weight, of the total weight of the composition. In some embodiments, the composition is not an emulsion. In some embodiments, the composition is immiscible in water. In some embodiments, the composition is an ophthalmic composition and is ophthalmically compatible. In some embodiments, the composition is sterile.

In another aspect, provided is a method of reducing body fat in a subject, comprising topically administering a composition as described herein to a subject in need thereof. In certain embodiments, the method is a therapeutic method. In other embodiments, the method is a cosmetic method.

In another aspect, provided is a composition as described herein for use in a method of reducing body fat in a subject. In another aspect, provided is use of a composition as described herein in the manufacture of a medicament for reducing body fat in a subject.

In another aspect, provided is a composition for use in for reducing fat in a subject suffering from steatoblepharon. In another aspect, provided is a method of treating steatoblepharon in a subject, comprising topically administering (e.g., applying to an eyelid of the subject) a composition as described herein to a subject in need thereof. In another aspect, provided is a composition as described herein for use in a method of treating steatoblepharon in a subject. In another aspect, provided is use a composition as described herein in the manufacture of a medicament for treating steatoblepharon in a subject.

In yet another aspect, provided is a kit comprising a composition as described herein and instructions for use.

In another aspect, provided is a process for manufacturing one or more of the inventive compositions in a sterile fashion, whereby the composition is sterile, endotoxin-free, and ophthalmically compatible, and therefore suitable for use on the eyelid or near the eye. For example, in one embodiment, provided is a process for manufacturing a sterile ointment, comprising the steps of dissolving a PFPRA compound (e.g. latanoprost or tafluprost) in a fatty acid ester (e.g., isopropyl myristate) to make a solution; microfiltration of the solution to make a filtrate; and combining the filtrate with an ointment base (e.g., a hydrocarbon base such as petroleum jelly). In certain embodiments, the method further comprises dissolving a preservative (e.g., chlorobutanol) in the fatty acid ester (e.g., isopropyl myristate).

Other objects and advantages will become apparent to those skilled in the art from consideration of the ensuing Detailed Description, Examples, and Claims.

DESCRIPTION OF THE DRAWINGS

FIG. 1 depicts three-dimensional molecular models of isopropyl myristate and latanoprost in energy-minimized conformations (solved in vacuo). Carbon atoms are shown in gray and oxygen atoms in red; hydrogens are not shown. Measured end-to-end distances (between heavy atom centers) are 19.9 Å for isopropyl myristate and 17.7 Å for latanoprost.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Certain compounds as described herein can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds as described herein are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., Tetrahedron 33:2725 (1977); Eliel, E. L. *Stereochemistry of Carbon Compounds* (McGrawHill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "aliphatic" refers to an alkyl, alkenyl, alkynyl, or carbocyclyl group, as defined herein.

As used herein, alone or as part of another group, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently unsubstituted (an "unsubstituted alkyl") or substituted (a "substituted alkyl") are substituted with one or more substituents. In certain embodiments, the alkyl group is an unsubstituted $C_{1-6}$ alkyl (e.g., $CH_3$). In certain embodiments, the alkyl group is a substituted $C_{1-6}$ alkyl.

As used herein "perhaloalkyl" or "halosubstituted alkyl" as defined herein refers to an alkyl group having from 1 to 10 carbon atoms wherein all of the hydrogen atoms are each independently replaced halogen, e.g., selected from fluoro, bromo, chloro or iodo ("$C_{1-10}$ perhaloalkyl"). In some embodiments, the alkyl moiety has 1 to 6 carbon atoms ("$C_{1-6}$ perhaloalkyl"). In some embodiments, the alkyl moiety has 1 to 5 carbon atoms ("$C_{1-5}$ perhaloalkyl 1"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include $CF_3$, $CF_2CF_3$, $CF_2CF_2CF_3$, $CCl_3$, $CFCl_2$, $CF_2Cl$ and the like.

As used herein, "alkyloxy" refers to an alkyl group, as defined herein, substituted with an oxygen atom, wherein the point of attachment is the oxygen atom. In certain embodiments, the alkyl group has 1 to 6 carbon atoms ("$C_{1-6}$ alkyloxy"). In some embodiments, the alkyl group has 1 to 4 carbon atoms ("$C_{1-4}$ alkyloxy"). Examples of $C_{1-4}$ alkyloxy groups include methoxy ($C_1$), ethoxy ($C_2$), propoxy ($C_3$), isopropoxy ($C_3$), butoxy ($C_4$), tertbutoxy ($C_5$) and the like. Examples of $C_{1-6}$ alkyloxy groups include the aforementioned $C_{1-4}$ alkyloxy groups as well as pentyloxy ($C_5$), isopentyloxy ($C_5$), neopentyloxy ($C_5$), hexyloxy ($C_6$) and the like. Unless otherwise specified, each instance of the alkyl moiety of the alkyloxy group is independently unsubstituted (an "unsubstituted alkyloxy") or substituted (a "substituted alkyloxy") with one or more substituents. In certain embodiments, the alkyloxy group is an unsubstituted $C_{1-6}$ alkyloxy. In certain embodiments, the alkyloxy group is a substituted $C_{1-6}$ alkyloxy.

As used herein, "alkylcarboxy" refers to a group of the formula $C(=O)OR^a$ wherein $R^a$ is an alkyl group as defined herein. In certain embodiments, the alkyl of the alkylcarboxy group has 1 to 6 carbon atoms ("$C_{1-6}$ alkylcarboxy"). In some embodiments, the alkyl of the alkylcarboxy group has 1 to 5 carbon atoms ("$C_{1-5}$ alkylcarboxy"). In some embodiments, the alkyl of the alkylcarboxy group has 1 to 4 carbon atoms ("$C_1$ alkylcarboxy"). In some embodiments, the alkyl of the alkylcarboxy group has 1 to 3 carbon atoms ("$C_{1-3}$ alkylcarboxy"). In some embodiments, the alkyl of the alkylcarboxy group has 1 to 2 carbon atoms ("$C_{1-2}$ alkylcarboxy"). Unless otherwise specified, each instance of the alkyl of the alkylcarboxy group is independently unsubstituted (an "unsubstituted alkylcarboxy") or substituted (a "substituted alkylcarboxy") with one or more substituents. In certain embodiments, the alkylcarboxy group is an unsubstituted $C_{1-6}$ alkylcarboxy. In certain embodiments, the alkylcarboxy group is a substituted $C_{1-6}$ alkylcarboxy.

As used herein, alone or as part of another group, "alkenyl" refers to a radical of a straight-chain or branched hydrocarbon group having from 2 to 20 carbon atoms and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1 Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-6}$ alkenyl. In certain embodiments, the alkenyl group is a substituted $C_{2-6}$ alkenyl.

As used herein, alone or as part of another group, "alkynyl" refers to a radical of a straight-chain or branched hydrocarbon group having from 2 to 20 carbon atoms and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atom ("$C_2$ alkynyl"). The one or more carbon-carbon triple bonds can be internal (such as in 2-butynyl) or terminal (such as in 1 Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-6}$ alkynyl. In certain embodiments, the alkynyl group is a substituted $C_{2-6}$ alkynyl.

As used herein, a "saturated or unsaturated acyclic hydrocarbon" refers to radical of a saturated or unsaturated, straight-chain or branched, hydrocarbon group having from 1 to 20 carbon atoms and optionally one or more carbon-carbon double or triple bonds. In certain embodiments, the hydrocarbon group is saturated. In some embodiments, the hydrocarbon group is unsaturated, and contains one or more carbon-carbon double or triple bonds. In some embodiments, the hydrocarbon group contains 1-10 carbon atoms. In certain embodiments, the hydrocarbon group contains 1-5 carbon atoms. In some embodiments, the hydrocarbon group contains 1-4 carbon atoms. In some embodiments, the hydrocarbon group contains 1-3 carbon atoms. In some embodiments, the hydrocarbon group contains 1-2 carbon atoms.

As used herein, "carbocyclyl" refers to a radical of a nonaromatic cyclic hydrocarbon group having from 3 to 7 ring carbon atoms ("$C_{3-7}$ carbocyclyl") and zero heteroatoms in the nonaromatic ring system. In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). Exemplary $C_{3-7}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with 1, 2, 3, 4, or 5 substituents as described herein. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-7}$ cycloalkyl groups include the aforementioned $C_{3-6}$ cycloalkyl groups as well as cycloheptyl ($C_7$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-7}$ cycloalkyl. In certain embodiments, the cycloalkyl group is a substituted $C_{3-7}$ cycloalkyl.

As used herein, alone or as part of another group, "heterocyclyl" refers to a radical of a 3 to 8-membered nonaromatic ring system having ring carbon atoms and 1 to 4 ring heteroatoms, wherein each heteroatom is independently selected from nitrogen, oxygen and sulfur ("3-8-membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered nonaromatic ring system having ring carbon atoms and 1-4 ring heteroatoms, wherein each heteroatom is independently selected from nitrogen, oxygen and sulfur ("5-8-membered heterocyclyl"). In some embodiments, a heterocyclyl group is a 5-6-membered nonaromatic ring system having ring carbon atoms and 1-4 ring heteroatoms, wherein each heteroatom is independently selected from nitrogen, oxygen and sulfur ("5-6-membered heterocyclyl"). In some embodiments, the 5-6-membered heterocyclyl has 1-3 ring heteroatoms selected from nitrogen, oxygen and sulfur. In some embodiments, the 5-6-membered heterocyclyl has 1-2 ring heteroatoms selected from nitrogen, oxygen and sulfur. In some embodiments, the 5-6-membered heterocyclyl has 1 ring heteroatom selected from nitrogen, oxygen and sulfur. Exemplary 3-membered heterocyclyls containing 1 heteroatom include, without limitation, aziridinyl, oxiranyl, thiorenyl. Exemplary 4 heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-8-membered heterocyclyl. In certain embodiments, the heterocyclyl group is a substituted 3-8-membered heterocyclyl.

As used herein, alone or as part of another group, "aryl" refers to a radical of a monocyclic or polycyclic (e.g., bicyclic or tricyclic) 4n+2 aromatic ring system having 6-10 ring carbon atoms and zero heteroatoms provided in the aromatic ring system ("$C_{6-10}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1 and 2-naphthyl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as described herein. In certain embodiments, the aryl group is an unsubstituted $C_{6-10}$ aryl. In certain embodiments, the aryl group is a substituted $C_{6-10}$ aryl.

As used herein, alone or as part of another group, "heteroaryl" refers to a radical of a 5-14-membered monocyclic or polycyclic (e.g., bicyclic) 4n+2 aromatic ring system having 4-10 ring carbon atoms and 1-4 ring heteroatoms provided in the aromatic ring system, wherein each heteroatom is independently selected from nitrogen, oxygen and sulfur ("5-10-membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10-membered aromatic ring system having ring carbon atoms and 1-4 ring heteroatoms provided in the aromatic ring system, wherein each heteroatom is independently selected from nitrogen, oxygen and sulfur ("5-10-membered heteroaryl"). In some embodiments, a heteroaryl group is a 5-8-membered aromatic ring system having ring carbon atoms and 1-4 ring heteroatoms provided in the aromatic ring system, wherein each heteroatom is independently selected from nitrogen, oxygen and sulfur ("5-8-membered heteroaryl"). In some embodiments, a heteroaryl group is a 5-6-membered aromatic ring system having ring carbon atoms and 1-4 ring heteroatoms provided in the aromatic ring system, wherein each heteroatom is independently selected from nitrogen, oxygen and sulfur ("5-6-membered heteroaryl"). In some embodiments, the 5-6-membered heteroaryl has 1-3 ring heteroatoms selected from nitrogen, oxygen and sulfur. In some embodiments, the 5-6-membered heteroaryl has 1-2 ring heteroatoms selected from nitrogen, oxygen and sulfur. In some embodiments, the 5-6-membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6 heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-10-membered heteroaryl. In certain embodiments, the heteroaryl group is a substituted 5-10-membered heteroaryl.

Alkyl, alkenyl, alkynyl, carbocyclyl, heterocyclyl, aryl, and heteroaryl, referred to without the suffix "-ene," describe a monoradical of alkyl, alkenyl, alkynyl, carbocyclyl, heterocyclyl, aryl, or heteroaryl, respectively, and as defined herein, wherein the monoradical is directly attached to a parent molecule or to another group by one bond (e.g., one single or double bond). Monoradical groups, as defined herein, may also be optionally substituted. Groups referred to with the suffix "-ene", such as alkylene, alkenylene, alkynylene, carbocyclylene, heterocyclylene, arylene and heteroarylene groups, describe a diradical of alkyl, alkenyl, alkynyl, carbocyclyl, heterocyclyl, aryl, or heteroaryl, respectively, and as defined herein, wherein the diradical is between and directly attached to two groups (e.g., between the parent molecule and another group) by two bonds (e.g., single or double bonds). Diradical groups may also be optionally substituted.

Alkyl, alkenyl, alkynyl, carbocyclyl, heterocyclyl, aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group (e.g., 1, 2, 3, 4, or 5 positions), and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —SC(=O)OR$^{aa}$, —OC(=O)SR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{aa}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR')OR$^{aa}$, —C(=NR$^{cc}$)N(R$^{cc}$)$_2$, —SO$_2$N(R$^{cc}$)$_2$, —SO$_2$R', —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{bb}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{cc}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(OR$^{ee}$)R$^{ff}$, —SH, —SR', —SSR$^{ee}$, —C(=O)R$^{ee}$, —CO$_2$H, —C(=O)OR$^{ee}$, —OC(=O)R$^{ee}$, —OC(=O)OR$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{2-6}$ alkenyl, C$_{2-6}$ alkynyl, C$_{3-7}$ carbocyclyl, 3-8-membered heterocyclyl, $C_{6-10}$ aryl, and 5-10-membered heteroaryl, or two $R^{ff}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, -OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_1$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_1$ alkyl, —SO$_2$OC$_{1-6}$ alkyl, —OSO$_2$C$_1$ alkyl, —SOC$_{1-6}$ alkyl, —Si(C$_{1-6}$ alkyl)$_3$, —OSi(C$_{1-6}$ alkyl)$_3$ -C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{2-6}$ alkenyl, C$_{2-6}$ alkynyl, C$_{3-7}$ carbocyclyl, 3-8-membered-heterocyclyl, C$_{6-10}$ aryl, and 5-10-membered heteroaryl; or two geminal $R^{gg}$ substituents can be joined to form =O or =S.

In certain embodiments, the carbon atom substituent is selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —S(=O)R$^{aa}$, —OS(=O)R$^{aa}$, —Si(R$^{aa}$)$_3$, C$_{1-6}$alkyl, C$_{2-6}$alkenyl, C$_{2-6}$alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

As used herein, the term "hydroxyl" or "hydroxy" refers to the group —OH. The term "substituted hydroxyl" or "substituted hydroxy," by extension, refers to a hydroxyl group wherein the oxygen atom is substituted with a group other than hydrogen, e.g., selected from —OR$^{aa}$, —ON(R$^{bb}$)$_2$, —OC(=O)R$^{aa}$, —OC(=O)SR$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$.

As used herein, the term "substituted amino" refers to a monosubstituted, disubstituted, or trisubstituted amino group, as defined herein.

As used herein, the term "monosubstituted amino" refers to an amino group substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group substituted with two groups other than hydrogen, and includes groups selected from —N(R$^{bb}$)$_2$, —NR$^{bb}$(=O)R$^{aa}$, NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "sulfonyl" refers to a group selected from —S(=O)$_2$OH, —S(=O)$_2$N(R$^{bb}$)$_2$, —S(=O)$_2$ R$^{aa}$, and —S(=O)$_2$OR$^{aa}$, wherein R$^{aa}$ and R$^{bb}$ are as defined herein.

As used herein, the term "sulfinyl" refers to —S(=O)OH and —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "silyl" refers to the group —Si(R')$_3$, wherein R$^{aa}$ is as defined herein.

As used herein, the term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$), wherein R$^{aa}$ and R$^{cc}$ are as defined herein.

As used herein, the term "phosphino" refers to the group —P(R$^{cc}$)$_3$, wherein R$^{cc}$ is as defined herein. An exemplary phosphino group is triphenylphosphine.

As used herein, the term "halo" or "halogen" refers to fluorine (fluoro, —F), chlorine (chloro, —Cl), bromine (bromo, —Br), or iodine (iodo, —I).

As used herein, "nitro" refers to the group —NO$_2$.

As used herein, "cyano" refers to the group —CN.

As used herein, "azido" refers to the group —N$_3$.

As used herein, "oxo" refers to the group =O.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an "amino protecting group". Amino protecting groups include, but are not limited to, —OH, —OR', —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$alkyl (e.g., aralkyl, heteroaralkyl), C$_{2-10}$alkenyl, C$_{2-10}$alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)

phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on the oxygen atom is an "oxygen protecting group". Oxygen protecting groups include, but are not limited to —$R^{aa}$, —$N(R^{bb})_2$, —$C(=O)R^{aa}$, —$C(=O)OR^{aa}$, —$C(=O)SR^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, the Examples and in the Claims. The invention is not intended to be limited in any manner by the above exemplary listing of substituents.

As used herein, the terms "salt", "acceptable salt", or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" means a compound that can hydrolyze, oxidize, or otherwise react under biological conditions (e.g., in vitro or in vivo enzymatic conditions) to provide a pharmacologically active compound. In certain cases, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

Other Definitions

"Disease", "disorder," and "condition" are used interchangeably herein.

As used herein, an "individual" or "subject" to which administration is contemplated includes, but is not limited to, humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the mammal is a human.

As used herein, "local administration" or "administering locally" or "local effect" means administration/application of the active ingredient or active metabolite thereof directly, or in proximity to, a part of the body, tissue, or lesion where said active substance is intended to exert its action. This may include, for example, topical administration to a part of the skin.

As used herein, unless otherwise specified, "topical administration" or "topically" means application to the surface of the skin, e.g., in a non-invasive manner.

As used herein, and unless otherwise specified, a "therapeutically effective amount" "an amount sufficient" or "sufficient amount" of a compound means the level, amount or concentration of the compound needed to treat a disease, disorder or condition, or to reduce or lower a particular parameter (e.g., body fat) in the body of a subject, without causing significant negative or adverse side effects to body or the treated tissue. The term "therapeutically effective amount" can encompass an amount that improves overall therapy, reduces or avoids symptoms or causes of disease or condition, or enhances the therapeutic efficacy of another therapeutically active agent.

As used herein, the terms "reduce", "reduction", "reducing", "lower", or "lowering" means to diminish or lessen the volume, size, mass, bulk, density, amount, and/or quantity of a substance (e.g., body fat, adipose tissue) in the body of a subject.

As used herein, the term "eliminate" means to completely remove any unwanted or undesired volume, size, mass, bulk, density, amount, and/or quantity of a substance (e.g., excess body fat, excess adipose tissue) in the body of a subject.

As used herein, "suffer", "suffers" or "suffering from" refers to a subject diagnosed with a particular disease or condition. As used herein, "likely to suffer" refers to a subject who has not been diagnosed with a particular disease or condition by a medical practitioner, but has a predisposition (e.g., genetic and/or physiologic predisposition), or exhibits signs or symptoms of the disease or condition.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition.

As used herein, unless otherwise specified, the terms "prevent," "preventing" and "prevention" contemplate an action that occurs before a subject begins to suffer from the specified disease or condition, which inhibits or reduces the severity of the disease or condition.

Conditions for which treatment and prevention are contemplated may be further classified as a medical condition or a cosmetic condition. A "medical condition," as used herein, refers to an abnormal condition that affects the body. A "cosmetic condition," as used herein, refers to a condition other than a medical condition that affects the physical appearance of the body. A cosmetic condition can occur, for example, due to normal processes in a body, such as aging, pregnancy, puberty, and exposure to the sun or the elements, or due to normal features of a body, such as inherited facial features or body shapes that are found in healthy individuals. Various medical and cosmetic conditions are described herein. A "cosmetic method" refers to a method or procedure intended to ameliorate a cosmetic condition in the subject, e.g., for the beautification of the subject's body or a part thereof, and a "cosmetic composition" is contemplated useful for such purpose. A "therapeutic method" refers to a method or procedure intended to treat or prevent a medical condition, and a "pharmaceutical composition" is contemplated useful for such purpose. However, while pharmaceutical compositions are contemplated useful for therapeutic and prophylactic purposes, and cosmetic compositions are contemplated useful for cosmetic purposes, there is overlap between the two compositions in terms of use of the composition. For example, a pharmaceutical composition is also contemplated useful for beautification purposes.

As used herein, unless otherwise specified, "excess submental fat" means excess fat on the body region including the mentum, the underside of the jaw, and the anterior neck, for example to the level of the inferior border of the cricoid.

As used herein, unless otherwise specified, "steatoblepharon" refers to a condition characterized by excess fat of the eyelids and/or periorbital tissue. The excess fat can be due to prolapse of orbital or periorbital fat. Steatoblepharon can occur in the lower or upper eyelid, or both. Steatoblepharon can be considered a cause of "eye bags."

The presence, amount, or severity of excess fat can be assessed objectively, e.g., by magnetic resonance imaging, computed tomography, biopsy, or skin calipers, or subjectively, e.g., by a clinician, a patient, or other observer, optionally with reference to a photonumeric, verbal, or descriptive scale or classification system, e.g., a five-step severity scale.

DETAILED DESCRIPTION OF CERTAIN
EMBODIMENTS OF THE INVENTION

The present invention relates to new, stable, manufacturable, well-tolerated, aesthetically pleasing compositions that, when topically applied to the skin, delivers a therapeutically effective amount of a prostaglandin FP receptor agonist (PFPRA compound), e.g., a prostaglandin F2α analog, e.g., latanoprost or tafluprost, to subcutaneous fat. More specifically, the invention relates to compositions for delivery of a PFPRA compound to subcutaneous fat comprising a PFPRA compound and a fatty acid ester, e.g., isopropyl myristate. The formulations are useful for local reduction of subcutaneous fat, and for other therapeutic uses as described herein. The invention also relates to methods for locally reducing body fat, comprising administering the inventive compositions to the skin. The invention also related to a process for manufacturing one or more of the inventive compositions, e.g., in a sterile fashion, whereby the composition is sterile, endotoxin-free, and ophthalmically compatible, and therefore suitable for use on the eyelid or near the eye. A particular advantage of the inventive formulations is suitability for application on the face and/or periorbital skin.

As described herein, no theoretical framework was available to the inventors to select or improve a composition for delivering a PFPRA compound to subcutaneous fat. Rather, the inventors found it necessary to test a wide range of conditions both in vitro and in vivo, with different formulation components at different concentrations and in different combinations. This testing led to the discovery that inclusion of a fatty acid ester (e.g., isopropyl myristate) in the composition conferred exceptionally better performance for delivery of a PFPRA compound and reduction of subcutaneous fat compared to, for example, use of 1,3-butanediol, diethylene glycol monoethyl ether, dimethylsulfoxide, ethanol, glycerol monooleate, hydroxypropyl cellulose, lauryl lactate, methyl laurate, oleyl alcohol, polysorbate 80, propylene glycol, and combinations thereof.

Without wishing to be bound by any particular theory, the special properties conferred by combining a fatty acid ester (e.g., isopropyl myristate) and a PFPRA may owe to certain similarities between the fatty acid ester (e.g., isopropyl myristate) and PFPRA compounds, i.e., similar structure and similar polarity. For example, latanoprost (cf. Examples 1-3) and isopropyl myristate are both isopropyl esters with parent acids comprising aliphatic tails of similar chain length (isopropyl myristate, 13 aliphatic carbons in the lipid tail; latanoprost, 13 aliphatic carbons if the cyclizing carbons 9 through 11 of the cyclopentyl ring are not counted). As shown in FIG. 1, in their energy-minimized 3-dimensional conformations, both compounds are roughly linear and of similar length. Furthermore, according to this structural hypothesis, latanoprost per se could serve as a penetration enhancer in this context, in that the 5-cis double bond of latanoprost (likewise present in most other PFPRA compounds) may lend particular improvement to the penetration characteristics of isopropyl myristate, as the structural kink of unsaturated molecules is known to interfere with close packing of the phospholipid bilayer and can thereby improve penetration.

In some embodiments, the composition comprises a PFPRA compound with a 5-cis double bond. In some embodiments, the composition comprises a PRPRA compound ester and a fatty acid ester, wherein both esters comprise the same ether (—OR$^{FA1}$) moiety. In some embodiments, the composition comprises a PRPRA compound ester and a fatty acid ester, wherein both esters comprise aliphatic tails (R$^{FA2}$) of similar chain length.

In some embodiments, the composition comprises isopropyl myristate. In some embodiments, the composition comprises isopropyl myristate and one or more additional different fatty acid esters, e.g., of the below formula, wherein the ether moiety of the ester (R$^{FA1}$) is optionally substituted $C_1$-$C_6$ alkyl, and the aliphatic moiety of the ester (R$^{FA2}$) is optionally substituted $C_{10}$-$C_{20}$ alkyl or optionally substituted $C_{10}$-$C_{20}$ alkenyl, and wherein the additional different fatty acid ester is not isopropyl myristate. It is understood that, according to the above theory, a different fatty acid ester may be used in the composition other than isopropyl myristate, e.g., such that the composition comprises a fatty acid ester of the below formula, wherein the ether moiety of the ester (R$^{FA1}$) is optionally substituted $C_1$-$C_6$ alkyl, and the aliphatic moiety of the ester (R$^{FA2}$) is optionally substituted $C_{10}$-$C_{20}$ alkyl or optionally substituted $C_{10}$-$C_{20}$ alkenyl, provided the composition does not comprise isopropyl myristate. Alternatively, in some embodiments, isopropyl myristate cannot be replaced with a different fatty acid ester. In some embodiments, the composition comprises isopropyl myristate and does not comprise one or more additional different fatty acid esters.

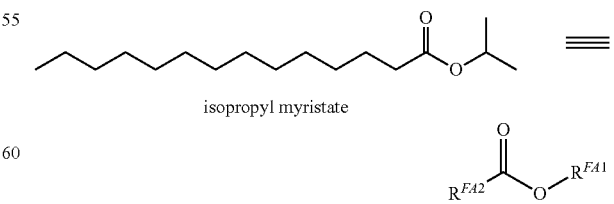

In certain embodiments, R$^{FA1}$ is an optionally substituted $C_{1-5}$alkyl, $C_{1-4}$alkyl, $C_{1-3}$alkyl, $C_{1-2}$alkyl, $C_{2-6}$alkyl, $C_{2-5}$alkyl, $C_{2-4}$alkyl, $C_{2-3}$alkyl, $C_{3-6}$alkyl, $C_{3-5}$alkyl, $C_{3-4}$alkyl, $C_{4-6}$alkyl, $C_{4-5}$alkyl, or $C_{5-6}$alkyl. In certain embodiments, $R^{FA1}$ is a branched alkyl group, e.g., for example, isopropyl, isobutyl, sec-butyl, tert-butyl, or neopentyl. In certain embodiments, $R^{FA1}$ is an unbranched alkyl group, e.g., for example, methyl, ethyl, n-propyl, n-butyl, n-pentyl, or n-hexyl. In certain embodiments, $R^{FA1}$ is an unsubstituted alkyl group, i.e., comprising only carbon and hydrogen atoms. In certain embodiments, $R^{FA1}$ is a substituted alkyl group, e.g., substituted by halogen atoms.

In certain embodiments, $R^{FA2}$ is an optionally substituted $C_{10}$-$C_{19}$ alkyl, $C_{10}$-$C_{18}$ alkyl, $C_{10}$-$C_{17}$ alkyl, $C_{10}$-$C_{16}$ alkyl, $C_{10}$-$C_{15}$ alkyl, $C_{10}$-$C_{14}$ alkyl, $C_{10}$-$C_{13}$ alkyl, $C_{11}$-$C_{20}$ alkyl, $C_{11}$-$C_{19}$ alkyl, $C_{11}$-$C_{18}$ alkyl, $C_{11}$-$C_{17}$ alkyl, $C_{11}$-$C_{16}$ alkyl, $C_{11}$-$C_{15}$ alkyl, $C_{11}$-$C_{14}$ alkyl, $C_{11}$-$C_{13}$ alkyl, $C_{12}$-$C_{19}$ alkyl, $C_{12}$-$C_{18}$ alkyl, $C_{12}$-$C_{17}$ alkyl, $C_{12}$-$C_{16}$ alkyl, $C_{12}$-$C_{15}$ alkyl, $C_{12}$-$C_{14}$ alkyl, $C_{12}$-$C_{13}$ alkyl, $C_{13}$-$C_{20}$ alkyl, $C_{13}$-$C_{19}$ alkyl, $C_{13}$-$C_{18}$ alkyl, $C_{13}$-$C_{17}$ alkyl, $C_{13}$-$C_{16}$ alkyl, $C_{13}$-$C_{15}$ alkyl, $C_{13}$-$C_{14}$ alkyl, $C_{14}$-$C_{20}$ alkyl, $C_{14}$-$C_{19}$ alkyl, $C_{14}$-$C_{18}$ alkyl, $C_{14}$-$C_{17}$ alkyl, $C_{14}$-$C_{16}$ alkyl, $C_{14}$-$C_{15}$ alkyl, $C_{15}$-$C_{20}$ alkyl, $C_{15}$-$C_{19}$ alkyl, $C_{15}$-$C_{18}$ alkyl, $C_{15}$-$C_{17}$ alkyl, or $C_{15}$-$C_{16}$ alkyl. In certain embodiments, $R^{FA2}$ is a straight chain (unbranched) alkyl group. In certain embodiments, $R^{FA2}$ is an unsubstituted alkyl group, i.e., comprising only carbon and hydrogen atoms. In certain embodiments, $R^{FA2}$ is a substituted alkyl group, e.g., substituted by halogen atoms.

In certain embodiments, $R^{FA2}$ is an optionally substituted $C_{10}$-$C_{19}$ alkenyl, $C_{10}$-$C_{18}$ alkenyl, $C_{10}$-$C_{17}$ alkenyl, $C_{10}$-$C_{16}$ alkenyl, $C_{10}$-$C_{15}$ alkenyl, $C_{10}$-$C_{14}$ alkenyl, $C_{10}$-$C_{13}$ alkenyl, $C_{11}$-$C_{20}$ alkenyl, $C_{11}$-$C_{19}$ alkenyl, $C_{11}$-$C_{18}$ alkenyl, $C_{11}$-$C_{17}$ alkenyl, $C_{11}$-$C_{16}$ alkenyl, $C_{11}$-$C_{15}$ alkenyl, $C_{11}$-$C_{14}$ alkenyl, $C_{11}$-$C_{13}$ alkenyl, $C_{12}$-$C_{19}$ alkenyl, $C_{12}$-$C_{18}$ alkenyl, $C_{12}$-$C_{17}$ alkenyl, $C_{12}$-$C_{16}$ alkenyl, $C_{12}$-$C_{15}$ alkenyl, $C_{12}$-$C_{14}$ alkenyl, $C_{12}$-$C_{13}$ alkenyl, $C_{13}$-$C_{20}$ alkenyl, $C_{13}$-$C_{19}$ alkenyl, $C_{13}$-$C_{18}$ alkenyl, $C_{13}$-$C_{17}$ alkenyl, $C_{13}$-$C_{16}$ alkenyl, $C_{13}$-$C_{15}$ alkenyl, $C_{13}$-$C_{14}$ alkenyl, $C_{14}$-$C_{20}$ alkenyl, $C_{14}$-$C_{19}$ alkenyl, $C_{14}$-$C_{18}$ alkenyl, $C_{14}$-$C_{17}$ alkenyl, $C_{14}$-$C_{16}$ alkenyl, $C_{14}$-$C_{15}$ alkenyl, $C_{15}$-$C_{20}$ alkenyl, $C_{15}$-$C_{19}$ alkenyl, $C_{15}$-$C_{18}$ alkenyl, $C_{15}$-$C_{17}$ alkenyl, $C_{15}$-$C_{16}$ alkenyl. In certain embodiments, $R^{FA2}$ is an unbranched alkenyl group. In certain embodiments, $R^{FA2}$ is an unsubstituted alkenyl group, i.e., comprising only carbon and hydrogen atoms. In certain embodiments, $R^{FA2}$ is a substituted alkenyl group, e.g., substituted by halogen atoms. In certain embodiments, $R^{FA2}$ is an alkenyl group comprising 1, 2, 3, or 4 double bonds, each independently cis or trans.

In certain embodiments, $R^{FA2}$ is selected from any one of the following saturated or unsaturated fatty acyl moieties:

Lauric —$(CH_2)^{10}CH_3$,
Myristic —$(CH_2)_{12}CH_3$,
Palmitic —$(CH_2)_{14}CH_3$,
Stearic —$(CH_2)_{16}CH_3$,
Myristoleic —$(CH_2)_7CH$=$CH(CH_2)_3CH_3$,
Palmitoliec —$(CH_2)_7CH$=$CH(CH_2)_5CH_3$,
Sapienic —$(CH_2)_4CH$=$CH(CH_2)_8CH_3$,
Oleic —$(CH_2)_7CH$=$CH(CH_2)_7CH_3$,
Linoleic —$(CH_2)_7CH$=$CHCH_2CH$=$CH(CH_2)_4CH_3$,
α-Linolenic —$(CH_2)_7$ CH=CHCH$_2$CH=CHCH$_2$CH=CHCH$_2$CH$_3$.

In certain embodiments, the total number of carbons atoms in the fatty acid ester, which include the number of carbons of $R^{FA1}$ and $R^{FA2}$ is between 15 and 19, inclusive, i.e., 15, 16, 17, 18, or 19 carbon atoms total.

In some embodiments, the total number of carbons in the fatty acid ester is selected to approximate the aliphatic chain length of the PFPRA compound. For example, in certain embodiments, the PRPRA compound has the same number of total carbon atoms in the sum of the aliphatic chain and ester moiety of the PFPRA compound, i.e., 15, 16, 17, 18, or 19 carbon atoms total.

In some embodiments, fatty acid ester is selected such that its predicted length (e.g. by molecular modeling) is similar (e.g., within ±3 Å) to the predicted length of the PFPRA compound. For example, isopropyl myristate has a predicted length (between the two most distant heavy atoms) of about 20 Å, which compares favorably with a length of about 18 Å for latanoprost and tafluprost, about 19 Å for bimatoprost, and about 20 Å for travoprost. In some embodiments, the predicted length is in an energy-minimized conformation. In some embodiments, the predicted length is of a conformation whereby freely rotating bonds are rotated as to provide a maximal length.

In certain embodiments, the composition further comprises an ointment base. As used herein, an ointment is a homogeneous, viscous, semi-solid preparation, which comprises a greasy, ointment base having a medium-to-high viscosity, that is intended for topical application to the skin. Exemplary ointment bases include, but are not limited to, hydrocarbon bases/waxes (e.g., plant and animal waxes (e.g., beeswax, lanolin, carnauba wax), petroleum derived waxes (e.g., hard paraffin wax or soft paraffin wax, i.e., petroleum jelly), microcyrstalline wax, ceresine wax, white wax, yellow wax, and cetyl esters wax). In certain embodiments, the ointment base is a hydrocarbon base, e.g., soft paraffin wax, e.g., petroleum jelly. Petroleum jelly (also known as petrolatum, white petrolatum, soft paraffin or multi-hydrocarbon) is a semi-solid preparation typically comprising (or consisting of) one or more saturated hydrocarbons with carbon numbers mainly higher than 25 (typically 25 to 50, such as 25 to 40, such as 25 to 35). It typically has a boiling point of from about 250° C. to about 350° C., such as about 280° C. to about 320° C., preferably about 300° C., and a melting point typically from about 36° C. to about 60° C. In certain embodiments, the petroleum jelly is obtained in sterile form or is sterilized prior to manufacturing the composition. In certain embodiments, the petroleum jelly is pure ultra white petroleum jelly.

In some embodiments, the composition further comprises an organic alcohol, e.g., methanol, ethanol, propanol, isopropanol, 1,3-butanediol, ethylene glycol, or propylene glycol. In certain embodiments, the organic alcohol is propylene glycol. However, in certain embodiments, 1,3-butanediol is excluded.

In clinical practice, topical delivery of compounds across the skin usually relies on the principle of passive diffusion. This principle dictates that a compound can only flow from an area of higher thermodynamic potential to one of lower thermodynamic potential. A solute held firmly by a vehicle will demonstrate little or no diffusion. Thus, the skilled artisan expects that a PFPRA compound (which is an oil-soluble compound) will penetrate better from an aqueous vehicle than from an oily vehicle (See, e.g., Barrett C W, Skin penetration. *J. Soc. Cosmetic Chemists* 1969; 20:487-499). Thus far, this theory has been borne out in practice, as PFPRA compound formulations for topical use have repeatedly selected water or ethanol as the preferred carrier for clinical use. See, e.g., prescribing inserts for Xalatan®, Travatan®, Lumigan®, and Zioptan®. See also Blume-Peytavi U et al, A randomized double-blind placebo-controlled pilot study to assess the efficacy of a 24-week topical treatment by latanoprost 0.1% on hair growth and pigmentation in healthy volunteers with androgenetic alopecia, *J Am Acad Dermatol* 2012; 66:794-800. Thus, another surprising aspect of the invention is that compositions comprising PFPRA compound formulated with a fatty acid ester (e.g., isopropyl myristate) and an ointment base, e.g., a hydrocarbon base such as petroleum jelly, delivers the PFPRA compound more effectively than an array of other vehicles, as disclosed herein. In certain embodiments, the composition does not include an aqueous or water-soluble component such as an organic alcohol. However, in certain embodiments, the composition does comprise an organic alcohol, e.g., propylene glycol, and, in certain embodiments, the composition comprises the organic alcohol in no greater than 50% by weight. In certain embodiments, the composition is hydrophobic, e.g., the composition is not miscible in water. In certain embodiments, the composition is not an emulsion. In certain embodiments, the composition does not contain mineral oil.

PFPRA Compounds

As used herein, a "PFPRA compound" can be any therapeutically relevant, naturally occurring or synthetic prostaglandin or prostaglandin analog, provided that it or its active metabolite (e.g., if an ester, the parent acid) suitably agonizes a prostaglandin FP receptor in a suitable functional assay. As used herein, a suitable degree of agonism can be defined, for example, as a half maximal effective concentration ($EC_{50}$) of 1 micromolar or less, preferably 100 nanomolar or less. A suitable functional assay can be, for example, assessment of phosphoinositide turnover in HEK293 cells expressing a cloned FP prostaglandin receptor. See, e.g., Sharif et al., *J. Ocular Pharmacol. Ther.* 2002; 18:313-324. Many PFPRA compounds can be classified as prostaglandins, prostanoids, or prostamides. Naturally occurring prostaglandins are a class of structurally related eicosanoid hormones that are derived enzymatically from arachidonic acid. An example of a naturally occurring prostaglandin PFPRA compound is prostaglandin F2a. Exemplary synthetic prostaglandins, which are prostaglandin F2a analogs, include, but are not limited to, latanoprost, latanoprost free acid, bimatoprost, bimatoprost free acid, tafluprost, tafluprost free acid, travoprost, travoprost free acid (a.k.a. fluprostenol), and prodrugs (e.g., 9-, 11-, and/or 15-ester derivatives) thereof.

In certain embodiments, the PFPRA compound is a compound of Formula (I) or (II):

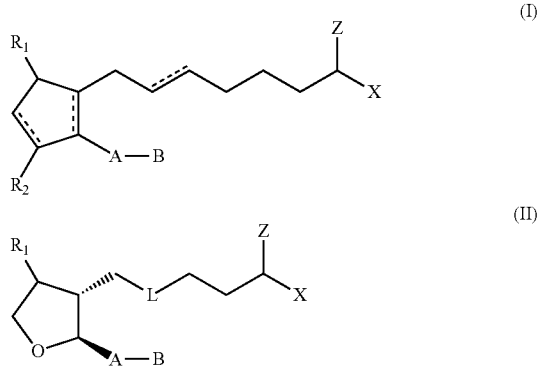

or a pharmaceutically acceptable salt, hydrate, solvate, stereoisomer, polymorph, tautomer, isotopically enriched derivative, or prodrug thereof;

wherein:
L is of the formula:

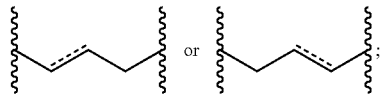

each instance of ≡≡≡≡≡≡ independently represents a single bond or a double bond, which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is —$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(=O)$R_5$, or —C(=O)O$R_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring;

Z is =O, =S, or =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms;

with regard to the compound of Formula (I), one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$alkyl, optionally substituted $C_{2-20}$alkenyl, optionally substituted $C_{2-20}$alkynyl, or —(CH$_2$)$_m$$R_7$ wherein m is 0 or an integer of between 1-10, inclusive, and $R_7$ is optionally substituted $C_{3-7}$ carbocyclyl, optionally substituted 3-8-membered-heterocyclyl, optionally substituted $C_{6-10}$aryl, or optionally substituted 5-14-membered-heteroaryl; and with regard to the compound of Formula (II), $R_1$ is =O, —OH, or —O(CO)$R_6$, wherein $R_6$ is a an optionally substituted $C_{1-20}$alkyl, optionally substituted $C_{2-20}$alkenyl, optionally substituted $C_{2-20}$alkynyl, or —(CH$_2$)$_m$$R_7$ wherein m is 0 or an integer of between 1-10, inclusive, and $R_7$ is optionally substituted $C_{3-7}$ carbocyclyl, optionally substituted 3-8-membered-heterocyclyl, optionally substituted $C_{6-10}$aryl, or optionally substituted 5-14-membered-heteroaryl.

In certain embodiments, the endocyclic dotted lines of Formula (I) (i.e., depicted in the 5-membered ring) each represent a single bond.

For example, in certain embodiments, wherein the endocyclic dotted lines of Formula (I) each represent a single bond, provided is a compound having any one of the following stereochemistry:

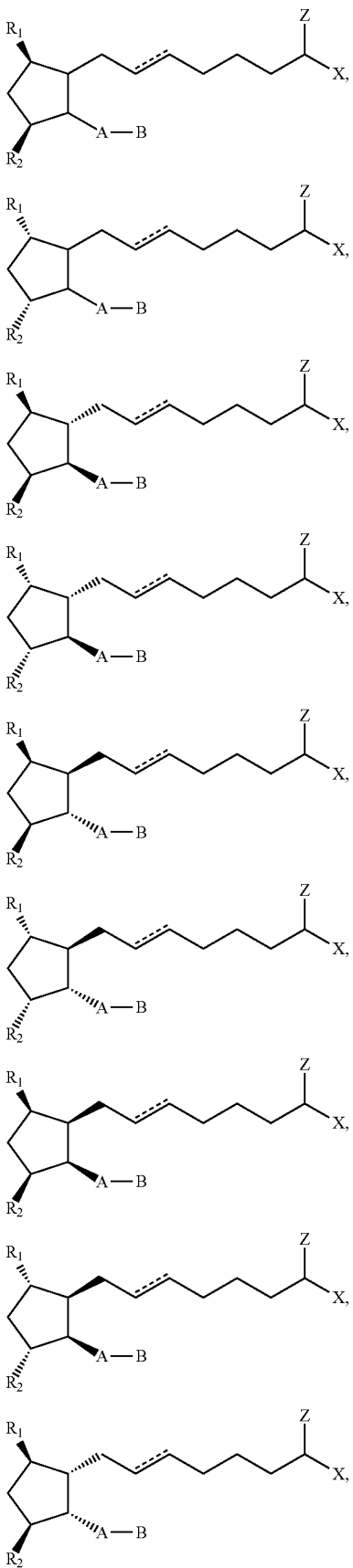

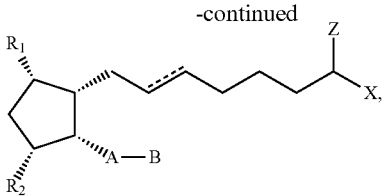

pharmaceutically acceptable salt, hydrate, solvate, stereoisomer, polymorph, tautomer, isotopically enriched derivative, or prodrug thereof, wherein ------, $R_1$, $R_2$, A, B, Z and X are as defined herein.

In certain embodiments, the exocyclic dotted line ------ (i.e., depicted outside of the 5-membered ring) of Formula (I) or (II) or a subset thereof represents a double bond in the cis or trans configuration. In certain embodiments, the exocyclic dotted line ------ represents a double bond in the cis configuration.

In certain embodiments, each instance of ------ independently represents a single bond or a double bond, which can be in the cis or trans configuration.

As generally defined above, one of $R_1$ and $R_2$ is =O, —OH, or a —O(CO)$R_6$ group, and the other is —OH or —O(CO)$R_6$, or $R_1$ is =O, and $R_2$ is H, wherein $R_6$ is an optionally substituted $C_{1-20}$alkyl, optionally substituted $C_{2-20}$alkenyl, optionally substituted $C_{2-20}$ alkynyl, or —(CH$_2$)$_m$R$_7$, wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, $R_1$ is =O, and $R_2$ is H.

In certain embodiments, one of $R_1$ and $R_2$ is —OH, substituted hydroxyl, or —O(CO)$R_6$, and the other is —OH, substituted hydroxyl, or —O(CO)$R_6$.

In certain embodiments, both $R_1$ and $R_2$ are —OH.

In certain embodiments, one of $R_1$ and $R_2$ is —OH, and the other is —O(CO)$R_6$. In certain embodiments, $R_1$ is —OH, and $R_2$ is —O(CO)$R_6$. In certain embodiments, $R_2$ is —OH, and $R_1$ is —O(CO)$R_6$. In certain embodiments, $R_6$ is an optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_6$ is —(CH$_2$)$_r$CH$_3$, wherein r is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$.

As generally defined above, A is optionally substituted $C_{1-10}$alkylene, optionally substituted $C_{2-10}$alkenylene, or optionally substituted $C_{2-10}$alkynylene, wherein the alkylene, alkenylene, or alkynylene group is optionally interrupted by one or more —O— or —S— groups.

In certain embodiments, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one —O— group.

In certain embodiments, A is optionally substituted $C_{4-6}$alkylene, optionally substituted $C_{4-6}$alkenylene or optionally substituted $C_{4-6}$alkynylene, wherein the alkylene, alkenylene, or alkynylene group is optionally interrupted by one —O— group.

In certain embodiments, A is optionally substituted $C_{4-6}$alkylene optionally interrupted by one —O— group. In certain embodiments, A is optionally substituted $C_{4-6}$alkenylene optionally interrupted by one —O— group. In certain embodiments, A is optionally substituted $C_{4-6}$alkynylene optionally interrupted by one —O— group.

In certain embodiments, A is substituted with one or more groups selected from the group consisting of halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, and optionally substituted 5-14-membered-heteroaryl.

In certain embodiments, A is substituted with =O.

In certain embodiments, A is substituted with —OC(=O)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$, wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl.

In certain embodiments, A is substituted with —OH or substituted hydroxyl.

In certain embodiments, A is substituted with substituted hydroxyl.

In certain embodiments, A is substituted with —OH.

In certain embodiments, A is of the Formula (i), (ii), (iii), (iv), (v), or (vi):

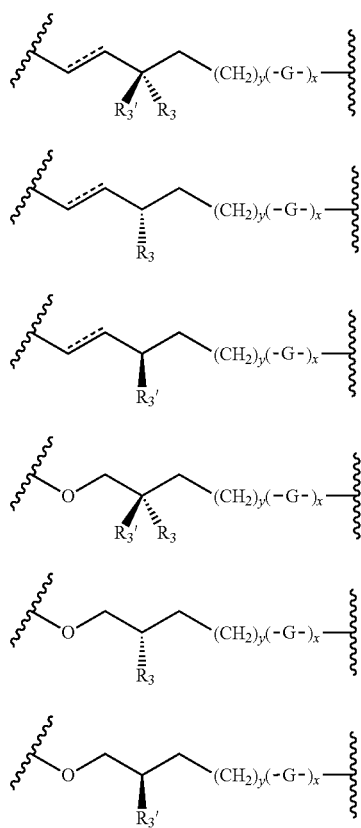

wherein each instance of ═════ independently represents a single bond or a double bond, which can be in the cis or trans configuration;

each instance of $R_3$ and $R_3'$ is hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$, wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form =O;

G is —O— or —S—;

y is 0, 1, or 2; and x is 0 or 1.

In certain embodiments, G is —O—. In certain embodiments, G is —S—.

In certain embodiments, ═════ of Formula (i), (ii), or (iii) represents a double bond in the cis configuration.

In certain embodiments, ═════ of Formula (i), (ii), or (iii) represents a double bond in the trans configuration.

In certain embodiments, the group of the Formula (i) is of the formula:

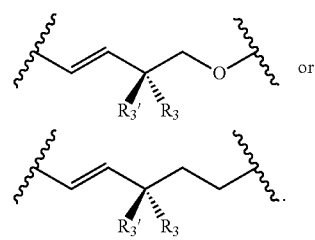

In certain embodiments, the group of the Formula (ii) is of the formula:

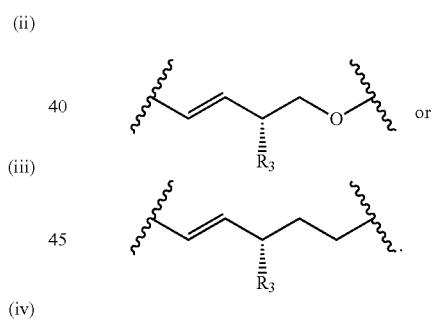

In certain embodiments, ═════ of Formula (i), (ii), or (iii) represents a single bond.

In certain embodiments, the group of the Formula (i) is of the formula:

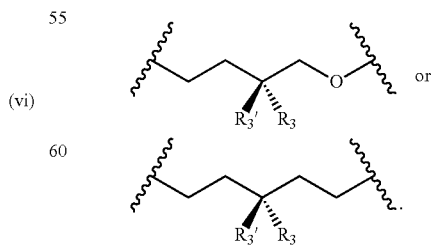

In certain embodiments, the group of the Formula (ii) is of the formula:

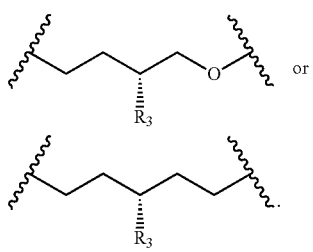
or

As generally defined above, each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_6$10 aryl, or optionally substituted 5-14-membered-heteroaryl; or $R_3$ and $R_3'$ are joined to form =O.

In certain embodiments, $R_3$ is hydrogen. In certain embodiments, $R_3'$ is hydrogen. In certain embodiments, $R_3$ is hydrogen and $R_3'$ is a non-hydrogen group. In certain embodiments, $R_3'$ is hydrogen and $R_3$ is a non-hydrogen group. In certain embodiments, however, neither $R_3$ nor $R_3'$ is hydrogen.

In certain embodiments, $R_3$ and $R_3'$ are joined to form =O.

In certain embodiments, $R_3$ and $R_3'$ are the same group. In certain embodiments, $R_3$ and $R_3'$ are different groups.

In certain embodiments, $R_3$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3$ is —O(CO)$R_8$. In certain embodiments, $R_3$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-15}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_3$ is —O(CO)$R_8$, and $R_8$ is —(CH$_2$)$_q$CH$_3$ wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_3$ is —OH or substituted hydroxyl. In certain embodiments, $R_3$ is substituted hydroxyl. In certain embodiments, $R_3$ is —OH.

In certain embodiments, $R_3'$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3'$ is —O(CO)$R_8$. In certain embodiments, $R_3'$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-15}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_3'$ is —O(CO)$R_8$, and $R_8$ is —(CH$_2$)$_q$CH$_3$, wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_3'$ is —OH or substituted hydroxyl. In certain embodiments, $R_3'$ is substituted hydroxyl. In certain embodiments, $R_3'$ is —OH.

In certain embodiments, $R_3$ is halogen, e.g., selected from fluoro, chloro, bromo, and iodo. In certain embodiments, $R_3'$ is halogen, e.g., selected from fluoro, chloro, bromo, and iodo. In certain embodiments, $R_3$ is halogen and $R_3'$ is halogen, e.g., each independently selected from fluoro, chloro, bromo, and iodo. In certain embodiments, both $R_3$ and $R_3'$ are fluoro.

In certain embodiments, y is 0; and x is 1. In certain embodiments, y is 0; and x is 0. In certain embodiments, y is 1; and x is 1. In certain embodiments, y is 1; and x is 0. In certain embodiments, y is 2; and x is 0. In certain embodiments, y is 2; and x is 1.

As defined generally above, B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl.

In certain embodiments, B is hydrogen.

In certain embodiments, B is optionally substituted $C_{1-30}$alkyl. In certain embodiments, B is optionally substituted $C_{2-30}$alkenyl. In certain embodiments, B is optionally substituted $C_{2-30}$alkynyl.

In certain embodiments, B is optionally substituted $C_{3-7}$carbocyclyl, e.g., optionally substituted cyclohexyl. In certain embodiments, B is optionally substituted 3-8-membered-heterocyclyl. In certain embodiments, B is optionally substituted 5-14-membered-heteroaryl. In certain embodiments, B is optionally substituted $C_{6-10}$aryl. In certain embodiments, B is optionally substituted $C_6$aryl (i.e., phenyl). In certain embodiments, B is optionally substituted $C_{10}$aryl (i.e., napthyl).

For example, in certain embodiments, B is an optionally substituted phenyl of the Formula (viii):

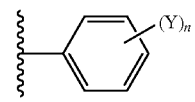
(viii)

wherein:

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino; and n is 0 or an integer of from 1 to 5, inclusive.

In certain embodiments, n is 0 or an integer from 1 to 3, inclusive.

In certain embodiments, n is 0 or an integer from 1 to 2, inclusive.

In certain embodiments, n is 0. In certain embodiments, n is 1. In certain embodiments, n is 2.

In certain embodiments, n is 3.

For example, in certain embodiments, wherein n is 1, the group of the Formula (viii) is of the formula:

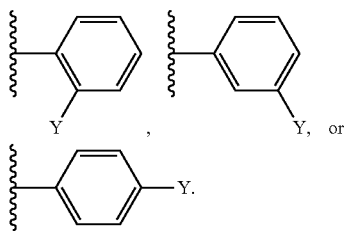

In certain embodiments, wherein n is 2, the group of the Formula (viii) is of the formula:

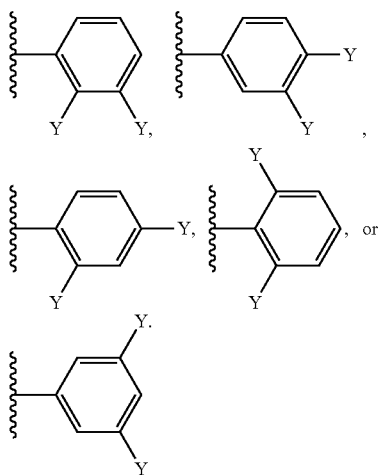

In certain embodiments, Y is halo, i.e. selected from fluoro, iodo, bromo, or chloro. In certain embodiments Y is chloro. In certain embodiments Y is fluoro.

In certain embodiments, Y is optionally substituted $C_{1-10}$alkyl or $C_{1-10}$perhaloalkyl.

In certain embodiments, Y is optionally substituted $C_{1-10}$alkyl. In certain embodiments, Y is optionally substituted $C_{1-6}$alkyl. In certain embodiments, Y is optionally substituted $C_{1-4}$alkyl. In certain embodiments, Y is optionally substituted $C_{1-3}$alkyl. In certain embodiments, Y is optionally substituted $C_{1-2}$alkyl. In certain embodiments, Y is $-CH_3$, $-CH_2F$, or $-CHF_2$.

In certain embodiments, Y is $C_{1-10}$perhaloalkyl. In certain embodiments, Y is $C_{1-6}$perhaloalkyl. In certain embodiments, Y is $C_{1-4}$perhaloalkyl. In certain embodiments, Y is $C_{1-3}$perhaloalkyl. In certain embodiments, Y is $C_{1-2}$perhaloalkyl. In certain embodiments, Y is $-CF_3$, $-CF_2C_1$, or $-CFCl_2$.

As generally defined above, Z is $=O$, $=S$, or $=NR_Z$, wherein $R_Z$ is selected from hydrogen, an amino protecting group, $-OH$, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms.

In certain embodiments, Z is $=O$.
In certain embodiments, Z is $=S$.
In certain embodiments, Z is $=NR_Z$, wherein $R_Z$ is selected from hydrogen, an amino protecting group, $-OH$, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl. In certain embodiments, Z is $=NR_Z$ and $R_Z$ is hydrogen.

In certain embodiments, Z represents two hydrogen atoms.

As generally defined above, X is $-OR_4$, $-SR_4$, or $-N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, $-C(=O)R_5$, or $-C(=O)OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring.

In certain embodiments, X is $-OR_4$. In certain embodiments, X is $-OR_4$, and $R_4$ is hydrogen. In certain embodiments, X is $-OR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is $-OR_4$, wherein $R_4$ is $-C(=O)R_5$, or $-C(=O)OR_5$.

In certain embodiments, X is $-OR_4$, and $R_4$ is $-C(=O)R_5$, and $R_5$ is optionally substituted $C_{1-20}$alkyl, optionally substituted $C_{2-20}$alkenyl, or optionally substituted $C_{2-20}$alkynyl.

In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is $-OR_4$, and $R_4$ is $-C(=O)OR_5$ and $R_5$ is optionally substituted $C_{1-20}$alkyl, optionally substituted $C_{2-20}$alkenyl, or optionally substituted $C_{2-20}$alkynyl.

In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is $-SR_4$. In certain embodiments, X is $-SR_4$, and $R_4$ is hydrogen. In certain embodiments, X is $-SR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, wherein $R_4$ is —C(=O)$R_5$, or —C(=O)O$R_5$.

In certain embodiments, X is —$SR_4$, and $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, and $R_4$ is —C(=O)O$R_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-20}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$. In certain embodiments, X is —$N(R_4)_2$ and at least one $R_4$ group is hydrogen. In certain embodiments, X is —$N(R_4)_2$ and neither of the two $R_4$ groups are hydrogen. In certain embodiments, X is —$N(R_4)_2$ and at least one $R_4$ is optionally substituted $C_{1-20}$alkyl, optionally substituted $C_{2-20}$alkenyl, or optionally substituted $C_{2-20}$alkynyl. In certain embodiments, X is —$N(R_4)_2$ and at least one $R_4$ is optionally substituted $C_{1-10}$alkyl, optionally substituted $C_{2-10}$alkenyl, or optionally substituted $C_{2-10}$alkynyl. In certain embodiments, X is —$N(R_4)_2$ and at least one $R_4$ is optionally substituted $C_{1-6}$alkyl, e.g., $C_{1-3}$alkyl, $C_{3-4}$alkyl, or $C_{4-6}$alkyl In certain embodiments, X is —$N(R_4)_2$ and at least one $R_4$ is optionally substituted $C_{2-6}$alkenyl, e.g., $C_{2-3}$alkenyl, $C_{3-4}$alkenyl, or $C_{4-6}$alkenyl. In certain embodiments, X is —$N(R_4)_2$ and at least one $R_4$ is optionally substituted $C_{2-4}$alkynyl, e.g., $C_{2-3}$alkynyl, $C_{3-4}$alkynyl, or $C_{4-6}$alkynyl. However, in certain embodiments, X is not —NH(iPr).

In certain embodiments, X is —$N(R_4)_2$ and at least one $R_4$ is —C(=O)$R_5$, or —C(=O)O$R_5$.

In certain embodiments, X is —$N(R_4)_2$ and at least one $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$-alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-4}$alkynyl, e.g., $C_{2-3}$alkynyl, $C_{3-4}$alkynyl, or $C_{4-6}$alkynyl.

In certain embodiments, X is —$N(R_4)_2$ and at least one $R_4$ is —C(=O)O$R_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In other embodiments, X is —$N(R_4)_2$ and the two $R_4$ groups are joined to form an optionally substituted 3-8-membered-heterocyclyl or optionally substituted 5-14-membered-heteroaryl ring.

In certain embodiments, wherein X is —O$R_4$, —$SR_4$, or —$N(R_4)_2$, any one of $R_4$ or $R_5$ is optionally substituted $C_{1-30}$alkyl (e.g., $C_{1-10}$alkyl, $C_{1-6}$alkyl, $C_{1-3}$alkyl, $C_{7-30}$alkyl, $C_{10-30}$alkyl, $C_{7-25}$alkyl, $C_{10-25}$alkyl, $C_{15-25}$alkyl). In certain embodiments, any one of $R_4$ or $R_5$ is optionally substituted $C_{2-30}$alkenyl (e.g., $C_{2-10}$alkenyl, $C_{2-6}$alkenyl, $C_{1-3}$alkenyl, $C_{7-30}$alkenyl, $C_{10-30}$alkenyl, $C_{7-25}$alkenyl, $C_{10-25}$alkenyl, $C_{15-25}$alkenyl). In certain embodiments, any one of $R_4$ or $R_5$ is optionally substituted $C_{2-30}$alkynyl (e.g., $C_{2-10}$alkynyl, $C_{2-6}$alkynyl, $C_{1-3}$alkynyl, $C_{7-30}$alkynyl, $C_{10-30}$alkynyl, $C_{7-25}$alkynyl, $C_{10-25}$alkynyl, $C_{15-25}$alkynyl).

In any of the above embodiments, when $R_4$ or $R_5$ are defined as a $C_{7-30}$alkyl or $C_{7-30}$alkenyl groups, such groups may also be referred to as "lipid tails." Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

Exemplary unsaturated lipid tails include, but are not limited to:

Myristoleic —$(CH_2)_7CH=CH(CH_2)_3CH_3$,

Palmitoliec —$(CH_2)_7CH=CH(CH_2)_5CH_3$,

Sapienic —$(CH_2)_4CH=CH(CH_2)_8CH_3$,

Oleic —$(CH_2)_7CH=CH(CH_2)_7CH_3$,

Linoleic —$(CH_2)_7CH=CHCH_2CH=CH(CH_2)_4CH_3$,

α-Linolenic —$(CH_2)_7$ $CH=CHCH_2CH=CHCH_2$ $CH=CHCH_2CH_3$,

Arachinodonic —$(CH_2)_3$ $CH=CHCH_2CH=CHCH_2$ $CH=CHCH_2CH=CH(CH_2)_4CH_3$,

Eicosapentaenoic —$(CH_2)_3$ $CH=CHCH_2CH=CHCH_2$ $CHCHCHCH=CHCHCH_3$,

Erucic —$(CH_2)_{11}CH=CH(CH_2)_7CH_3$, and

Docosahexaenoic —$(CH_2)_2$ $CH=CHCH_2CH=CHCH_2$ $CH=CHCH_2CH=CHCH_2$ $CH=CHCH_2CH=CH-CHCH_3$.

Exemplary saturated lipid tails include, but are not limited to:

Lauric —$(CH_2)_{10}CH_3$,

Myristic —$(CH_2)_{12}CH_3$,

Palmitic —$(CH_2)_{14}CH_3$,

Stearic —$(CH_2)_{16}CH_3$,

Arachidic —$(CH_2)_{18}CH_3$,

Behenic —$(CH_2)_{20}CH_3$,

Lignoceric —$(CH_2)_{22}CH_3$, and

Cerotic —$(CH_2)_{24}CH_3$.

In certain embodiments of Formula (I), the compound is of Formula (I-a):

(I-a)

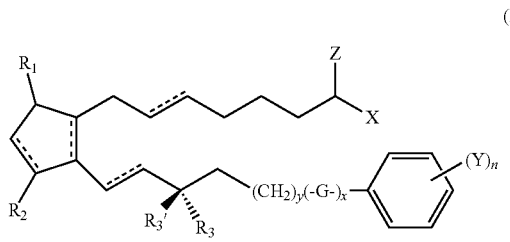

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

- each instance of ═════ independently represents a single bond or a double bond which can be in the cis or trans configuration;
- each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form =O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;
y is 0, 1, or 2;
x is 0 or 1; and
n is 0 or an integer of from 1 to 5, inclusive.

In certain embodiments of Formula (I-a), wherein $R_3'$ is hydrogen, the compound is of Formula (I-b):

(I-b)

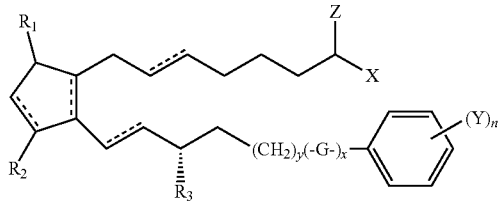

or a pharmaceutically acceptable salt, hydrate, solvate, stereoisomer, polymorph, tautomer, isotopically enriched derivative, or prodrug thereof; wherein ═════, $R_1$, $R_2$, $R_3$, Z, X, Y, G, y, x, and n are as defined herein.

In certain embodiments of Formula (I-a), wherein $R_3$ is hydrogen, the compound is of Formula (I-c):

(I-c)

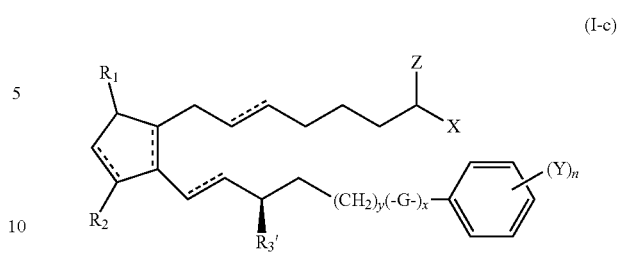

or a pharmaceutically acceptable salt, hydrate, solvate, stereoisomer, polymorph, tautomer, isotopically enriched derivative, or prodrug thereof; wherein ═════, $R_1$, $R_2$, $R_3'$, Z, X, Y, G, y, x, and n are as defined herein.

In certain embodiments, G is —O—. In certain embodiments, G is —S—.

In certain embodiments of Formula (I-a), wherein G is —O—, provided is a compound of Formula (I-a1):

(I-a1)

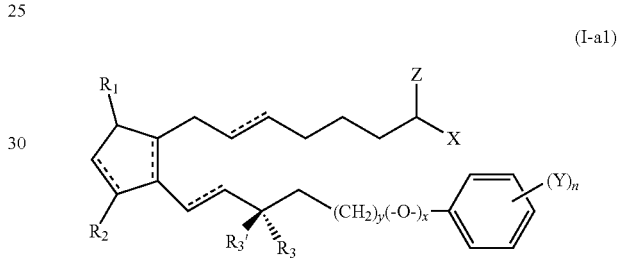

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ═════, $R_1$, $R_2$, $R_3$, Z, X, Y, y, x, and n are as defined herein.

In certain embodiments of Formula (I-b), wherein G is —O—, the compound is of Formula (I-b1):

(I-b1)

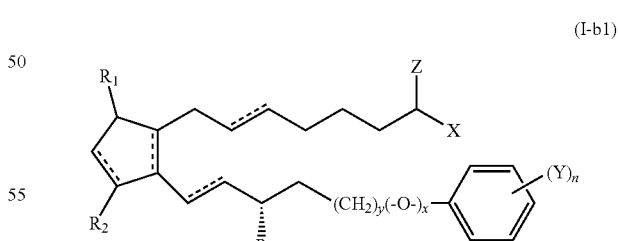

or a pharmaceutically acceptable salt, hydrate, solvate, stereoisomer, polymorph, tautomer, isotopically enriched derivative, or prodrug thereof; wherein ═════, $R_1$, $R_2$, $R_3$, Z, X, Y, y, x, and n are as defined herein.

In certain embodiments of Formula (I-c), wherein G is —O—, the compound is of Formula (I-c1):

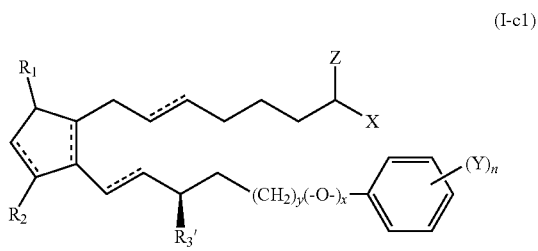

(I-c1)

or a pharmaceutically acceptable salt, hydrate, solvate, stereoisomer, polymorph, tautomer, isotopically enriched derivative, or prodrug thereof; wherein =====, $R_1$, $R_2$, $R_3'$, Z, X, Y, y, x, and n are as defined herein.

In certain embodiments of Formula (I-a), wherein G is —S—, provided is a compound of Formula (I-a2):

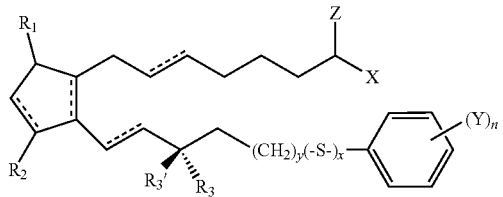

(I-a2)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein =====, $R_1$, $R_2$, $R_3$, $R_3'$, Z, X, Y, y, x, and n are as defined herein.

In certain embodiments of Formula (I-b), wherein G is —S—, the compound is of Formula (I-b2):

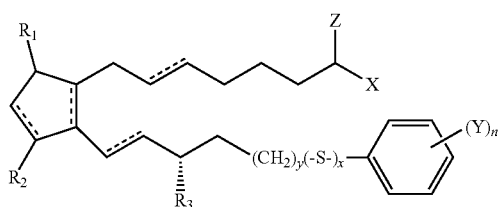

(I-b2)

or a pharmaceutically acceptable salt, hydrate, solvate, stereoisomer, polymorph, tautomer, isotopically enriched derivative, or prodrug thereof; wherein =====, $R_1$, $R_2$, $R_3$, Z, X, Y, y, x, and n are as defined herein.

In certain embodiments of Formula (I-c), wherein G is —S—, the compound is of Formula (I-c2):

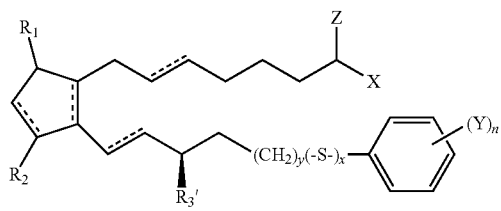

(I-c2)

or a pharmaceutically acceptable salt, hydrate, solvate, stereoisomer, polymorph, tautomer, isotopically enriched derivative, or prodrug thereof; wherein =====, $R_1$, $R_2$, $R_3'$, Z, X, Y, y, x, and n are as defined herein.

In certain embodiments, the compound of Formula (I-a) has the following stereochemistry, also referred to herein as a compound of Formula (I-d):

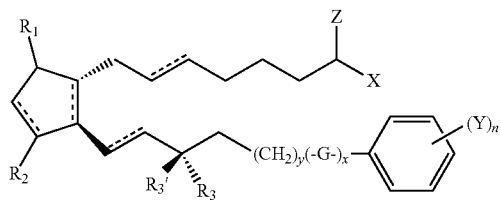

(I-d)

or a pharmaceutically acceptable salt, hydrate, solvate, stereoisomer, polymorph, tautomer, isotopically enriched derivative, or prodrug thereof; wherein =====, $R_1$, $R_2$, $R_3$, $R_3'$, Z, Y, G, X, y, x, and n are as defined herein.

In certain embodiments of Formula (I-d), wherein $R_3'$ is hydrogen, the compound is of Formula (I-e):

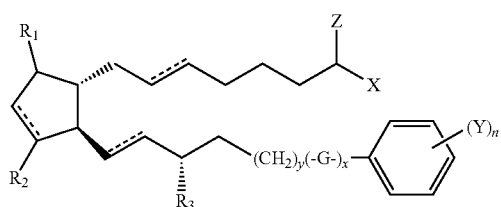

(I-e)

or a pharmaceutically acceptable salt, hydrate, solvate, stereoisomer, polymorph, tautomer, isotopically enriched derivative, or prodrug thereof; wherein =====, $R_1$, $R_2$, $R_3$, Z, X, Y, G, y, x, and n are as defined herein.

In certain embodiments of Formula (I-d), wherein $R_3$ is hydrogen, the compound is of Formula (I-f):

(I-f)

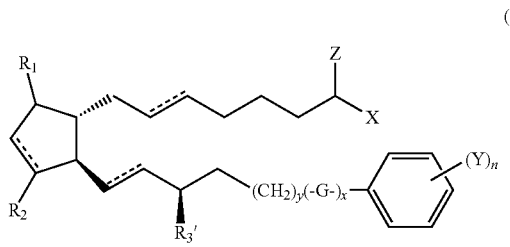

or a pharmaceutically acceptable salt, hydrate, solvate, stereoisomer, polymorph, tautomer, isotopically enriched derivative, or prodrug thereof; wherein ═════, $R_1$, $R_2$, $R_3'$ Z, X, Y, G, y, x, and n are as defined herein.

In certain embodiments, G is —O—. In certain embodiments, G is —S—.

In certain embodiments of Formula (I-d), wherein G is —O—, the compound is of Formula (I-d1):

(I-d1)

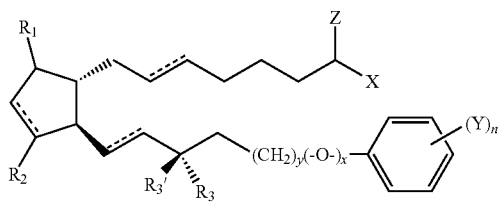

or a pharmaceutically acceptable salt, hydrate, solvate, stereoisomer, polymorph, tautomer, isotopically enriched derivative, or prodrug thereof; wherein ═════, $R_1$, $R_2$, $R_3$, $R_3'$, Z, Y, X, y, x, and n are as defined herein.

In certain embodiments of Formula (I-e), wherein G is —O—, the compound is of Formula (I-e1):

(I-e1)

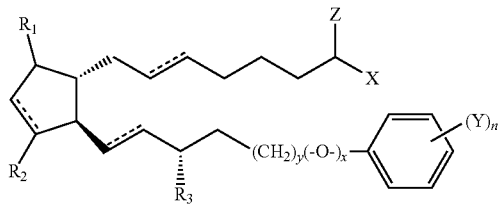

or a pharmaceutically acceptable salt, hydrate, solvate, stereoisomer, polymorph, tautomer, isotopically enriched derivative, or prodrug thereof; wherein ═════, $R_1$, $R_2$, $R_3$, Z, X, Y, y, x, and n are as defined herein.

In certain embodiments of Formula (I-f), wherein G is —O—, the compound is of Formula (I-f1):

(I-f1)

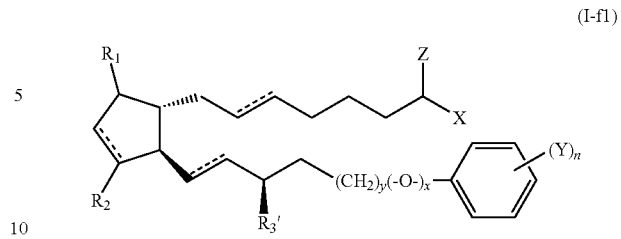

or a pharmaceutically acceptable salt, hydrate, solvate, stereoisomer, polymorph, tautomer, isotopically enriched derivative, or prodrug thereof; wherein ═════, $R_1$, $R_2$, $R_3'$, Z, X, Y, y, x, and n are as defined herein.

In certain embodiments of Formula (I-d), wherein G is —S—, the compound is of Formula (I-d2):

(I-d2)

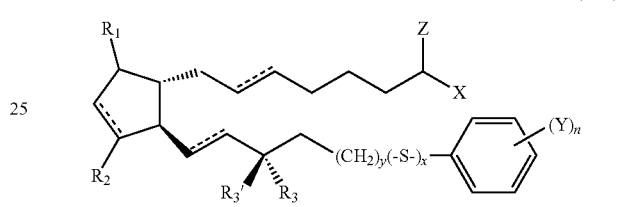

or a pharmaceutically acceptable salt, hydrate, solvate, stereoisomer, polymorph, tautomer, isotopically enriched derivative, or prodrug thereof; wherein ═════, $R_1$, $R_2$, $R_3$, $R_3'$, Z, Y, X, y, x, and n are as defined herein.

In certain embodiments of Formula (I-e), wherein G is —S—, the compound is of Formula (I-e2):

(I-e2)

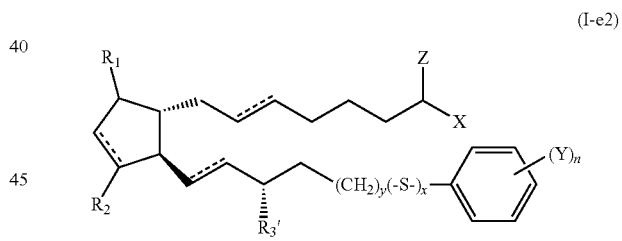

or a pharmaceutically acceptable salt, hydrate, solvate, stereoisomer, polymorph, tautomer, isotopically enriched derivative, or prodrug thereof; wherein ═════, $R_1$, $R_2$, $R_3$, Z, X, Y, y, x, and n are as defined herein.

In certain embodiments of Formula (I-f), wherein G is —S—, the compound is of Formula (I-f2):

(I-f2)

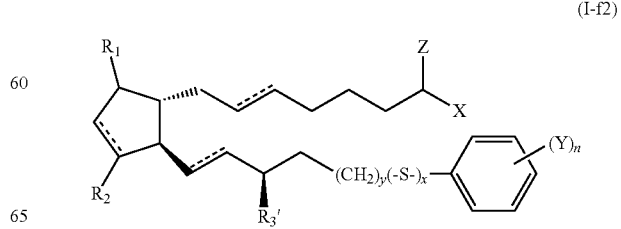

or a pharmaceutically acceptable salt, hydrate, solvate, stereoisomer, polymorph, tautomer, isotopically enriched derivative, or prodrug thereof; wherein ======, $R_1$, $R_2$, $R_3$', Z, X, Y, y, x, and n are as defined herein.

In certain embodiments, Z is =O. In certain embodiments, each ====== represents a single bond. In certain embodiments, each endocyclic ====== represents a single bond. In certain embodiments at least one exocyclic ====== represents a cis-double bond. In certain embodiments, each instance of $R_1$ and $R_2$ is —OH. In certain embodiments, each instance of $R_1$ and $R_2$ is —O(CO)$R_6$. In certain embodiments, one of $R_1$ and $R_2$ is —OH, and the other one is —O(CO)$R_6$. In certain embodiments, one of $R_3$ and $R_3$' is —O(CO)$R_8$, and the other is hydrogen. In certain embodiments, $R_1$ is —OH, $R_2$ is —O(CO)$R_6$, one of $R_3$ and $R_3$' is —OH, and the other is hydrogen. In certain embodiments, $R_2$ is —OH, $R_1$ is —O(CO)$R_6$, one of $R_3$ and $R_3$' is —OH, and the other is hydrogen. In certain embodiments, each of $R_1$ and $R_2$ is —OH, and one of $R_3$ and $R_3$' is —O(CO)$R_8$, and the other is hydrogen. In certain embodiments, each instance of $R_1$ and $R_2$ is —O(CO)$R_6$, and one of $R_3$ and $R_3$' is —O(CO)$R_8$, and the other is hydrogen. In certain embodiments, —O(CO)$R_6$ and —O(CO)$R_8$ attached to the compound are the same group. In certain embodiments, —O(CO)$R_6$ and —O(CO)$R_8$ attached to the compound are different groups.

In certain embodiments of Formula (I-d), wherein Z is =O, each endocyclic ====== represents a single bond, and at least one exocyclic ====== represents a cis-double bond, provided is a compound of Formula (I-d3) having the following stereochemistry:

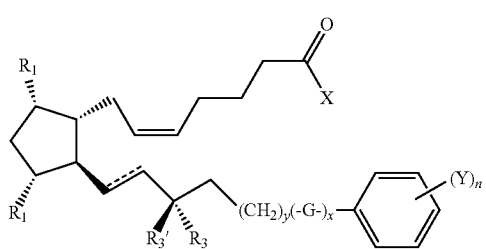

(I-d3)

or a pharmaceutically acceptable salt, hydrate, solvate, stereoisomer, polymorph, tautomer, isotopically enriched derivative, or prodrug thereof; wherein ======, $R_1$, $R_2$, $R_3$, $R_3$', G, Y, X, y, x, and n are as defined herein.

In certain embodiments of Formula (I-e), wherein Z is =O, each endocyclic ====== represents a single bond, and at least one exocyclic ====== represents a cis-double bond, provided is a compound of Formula (I-e3) having the following stereochemistry:

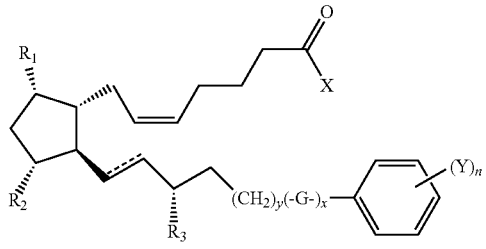

(I-e3)

or a pharmaceutically acceptable salt, hydrate, solvate, stereoisomer, polymorph, tautomer, isotopically enriched derivative, or prodrug thereof; wherein ======, $R_1$, $R_2$, $R_3$, G, X, Y, y, x, and n are as defined herein.

In certain embodiments of Formula (I-f), wherein Z is =O, each endocyclic ====== represents a single bond, and at least one exocyclic ====== represents a cis-double bond, provided is a compound of Formula (I-f3) having the following stereochemistry:

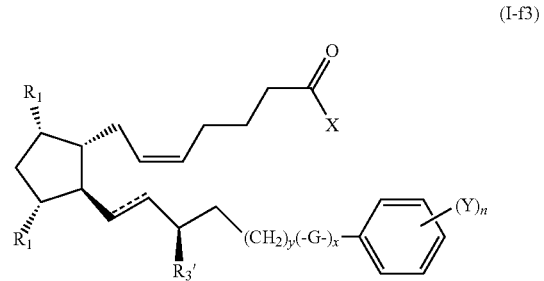

(I-f3)

or a pharmaceutically acceptable salt, hydrate, solvate, stereoisomer, polymorph, tautomer, isotopically enriched derivative, or prodrug thereof; wherein ======, $R_1$, $R_2$, $R_3$', G, X, Y, y, x, and n are as defined herein.

In certain embodiments of Formula (I-d3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, provided is a compound of Formula (I-d4), (I-d5), and (I-d6) having the following stereochemistry:

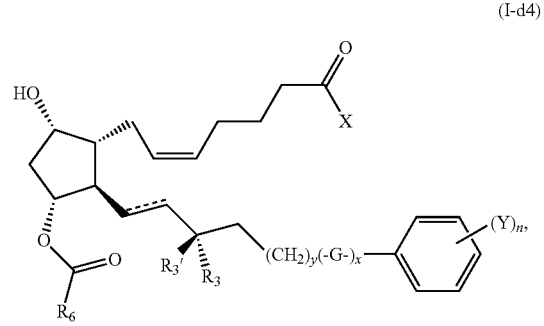

(I-d4)

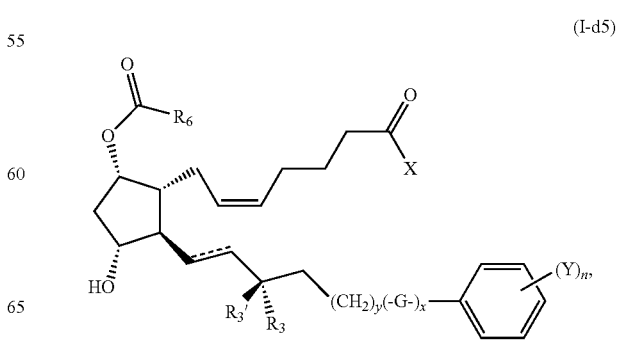

(I-d5)

(I-d6)

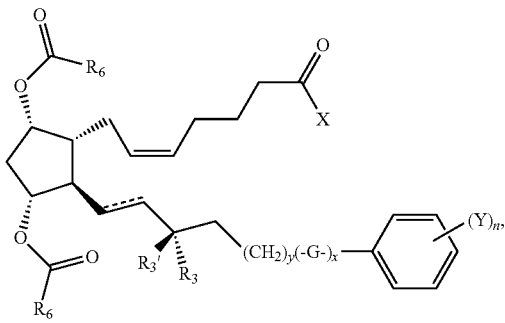

or a pharmaceutically acceptable salt, hydrate, solvate, stereoisomer, polymorph, tautomer, isotopically enriched derivative, or prodrug thereof; wherein ------, $R_6$, $R_3$, $R_3'$, G, Y, X, y, x, and n are as defined herein.

In certain embodiments of Formula (I-d3), wherein $R_3$ is —O(CO)$R_8$ or $R_3'$ is —O(CO)$R_8$, provided is a compound of Formula (I-d7) and (I-d8) having the following stereochemistry:

(I-d7)

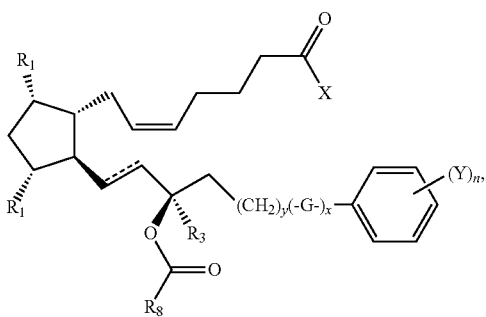

(I-d8)

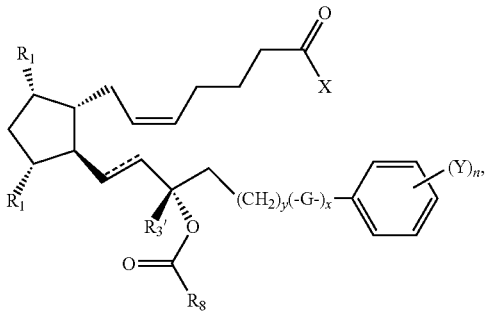

or a pharmaceutically acceptable salt, hydrate, solvate, stereoisomer, polymorph, tautomer, isotopically enriched derivative, or prodrug thereof; wherein ------, $R_1$, $R_2$, $R_3$, $R_3'$, $R_8$, G, Y, X, y, x, and n are as defined herein.

In certain embodiments of Formula (I-d3), wherein $R_1$ and $R_2$ are each —OH and $R_3$ is —O(CO)$R_8$, or wherein $R_1$ and $R_2$ are each —OH and $R_3'$ is —O(CO)$R_8$, provided is a compound of Formula (I-d9) and (I-d10) having the following stereochemistry:

(I-d9)

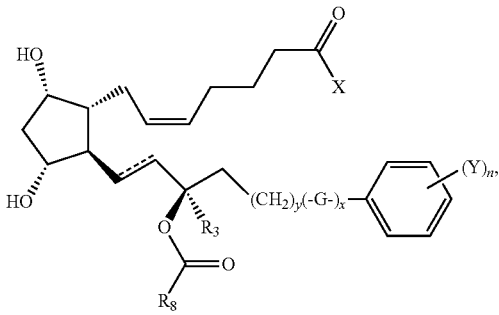

(I-d10)

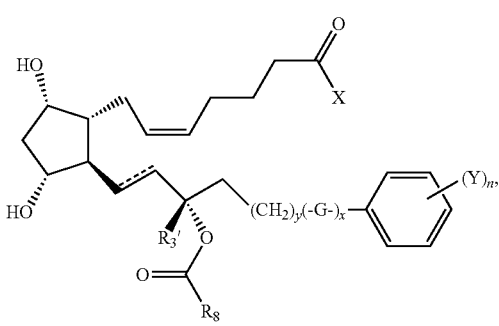

or a pharmaceutically acceptable salt, hydrate, solvate, stereoisomer, polymorph, tautomer, isotopically enriched derivative, or prodrug thereof; wherein ------, $R_3$, $R_3'$, $R_8$, G, Y, X, y, x, and n are as defined herein.

In certain embodiments of Formula (I-e3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, and $R_3'$ is hydrogen and $R_3$ is —OH, provided is a compound of Formula (I-d11), (I-d12), and (I-d13) having the following stereochemistry:

(I-d11)

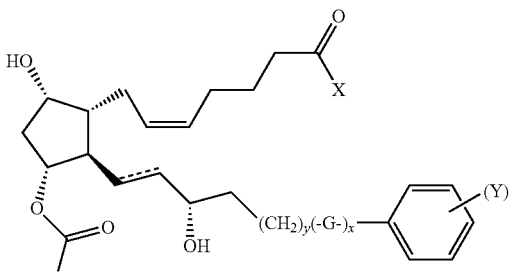

(I-d12)

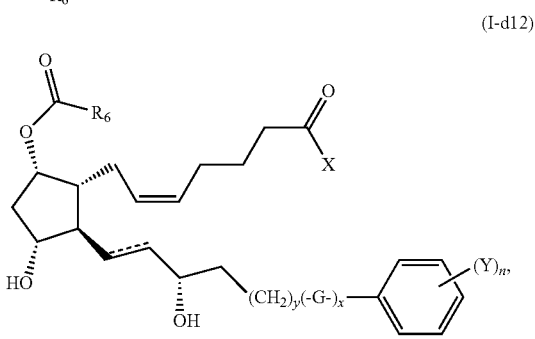

-continued (I-d13)

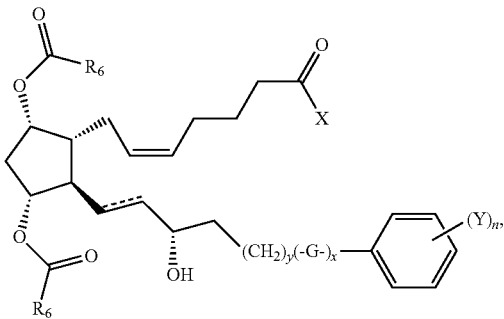

or a pharmaceutically acceptable salt, hydrate, solvate, stereoisomer, polymorph, tautomer, isotopically enriched derivative, or prodrug thereof; wherein ≡≡≡≡≡, $R_6$, $R_3$, $R_3'$, G, Y, X, y, x, and n are as defined herein.

In certain embodiments of Formula (I-d8), wherein each of $R_1$ and $R_2$ are —O(CO)$R_6$ and $R_3'$ is hydrogen, provided is a compound of Formula (I-d14) having the following stereochemistry:

(I-d14)

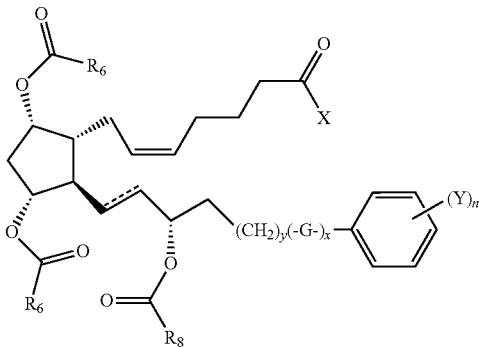

or a pharmaceutically acceptable salt, hydrate, solvate, stereoisomer, polymorph, tautomer, isotopically enriched derivative, or prodrug thereof; wherein ≡≡≡≡≡, $R_6$, $R_8$, G, Y, X, y, x, and n are as defined herein.

In certain embodiments of Formula (I-d2), wherein Z is =O, each instance of $R_1$ and $R_2$ is —OH, and each ≡≡≡≡≡ represents a single bond, provided is a compound of Formula (I-g):

(I-g)

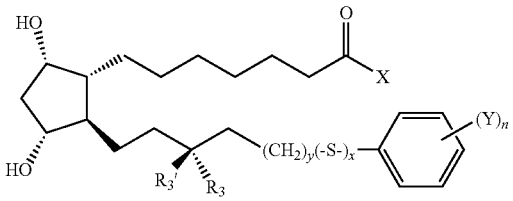

or a pharmaceutically acceptable salt, hydrate, solvate, stereoisomer, polymorph, tautomer, isotopically enriched derivative, or prodrug thereof; wherein X, Y, $R_3$, $R_3'$, y, x, and n are as defined herein.

In certain embodiments of Formula (I-d1), wherein each instance of $R_1$ and $R_2$ is —OH, and Z is =O, provided is a compound of Formula (I-h):

(I-h)

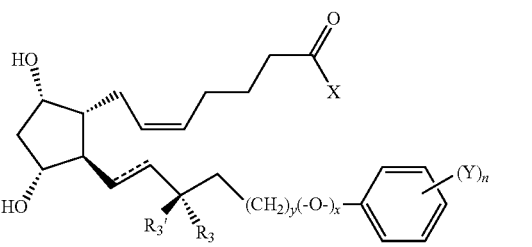

or a pharmaceutically acceptable salt, hydrate, solvate, stereoisomer, polymorph, tautomer, isotopically enriched derivative, or prodrug thereof; wherein ≡≡≡≡≡, $R_3$, $R_3'$, Y, X, y, x, and n are as defined herein.

In certain embodiments of Formula (I-h), wherein $R_3'$ is hydrogen, provided is a compound of Formula (I-i):

(I-i)

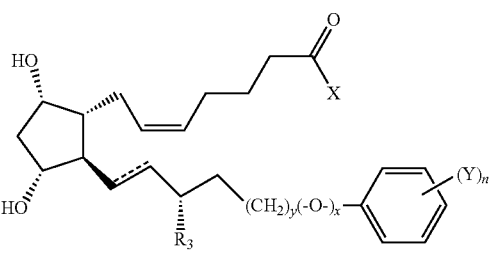

or a pharmaceutically acceptable salt, hydrate, solvate, stereoisomer, polymorph, tautomer, isotopically enriched derivative, or prodrug thereof; wherein ≡≡≡≡≡, $R_3$, Y, X, y, x, and n are as defined herein.

In certain embodiments of Formula (I-i), wherein $R_3$ is —OH, provided is a compound of Formula (I-j):

(I-j)

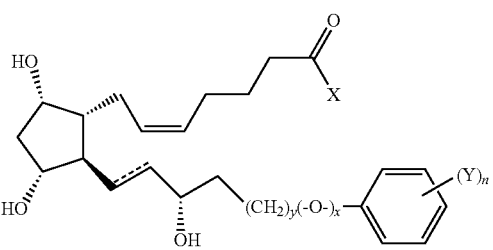

or a pharmaceutically acceptable salt, hydrate, solvate, stereoisomer, polymorph, tautomer, isotopically enriched derivative, or prodrug thereof; wherein Y, X, y, x, and n are as defined herein.

In certain embodiments of Formula (I-h), wherein $R_3$ is F and $R_3'$ is F, provided is a compound of Formula (I-k):

(I-k)

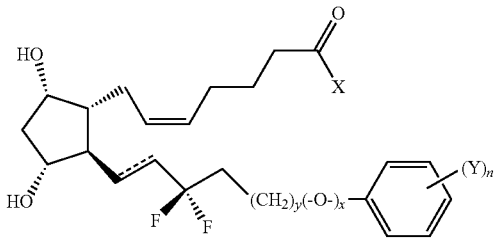

or a pharmaceutically acceptable salt, hydrate, solvate, stereoisomer, polymorph, tautomer, isotopically enriched derivative, or prodrug thereof; wherein ======, Y, X, y, x, and n are as defined herein.

In certain embodiments of Formula (I-i), wherein $R_3$ is —O(CO)$R_8$, provided is a compound of Formula (I-j):

(I-j)

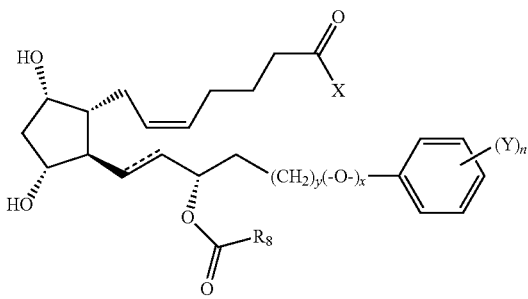

or a pharmaceutically acceptable salt, hydrate, solvate, stereoisomer, polymorph, tautomer, isotopically enriched derivative, or prodrug thereof; wherein $R_8$, Y, X, y, x, and n are as defined herein.

In certain embodiments of Formula (I), the compound of Formula (I-l):

(I-l)

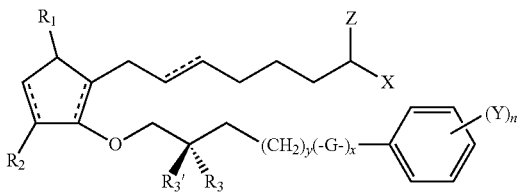

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

each instance of ====== independently represents a single bond or a double bond which can be in the cis or trans configuration;

each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form =O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;
y is 0, 1, or 2;
x is 0 or 1; and
n is 0 or an integer of from 1 to 5, inclusive.

In certain embodiments of Formula (I-l), wherein Z is =O, and $R_1$ and $R_2$ are each —OH, provided is a compound of Formula (I-m):

(I-m)

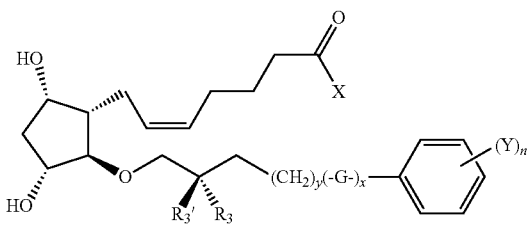

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

In certain embodiments of Formula (I-m), wherein $R_3'$ is hydrogen, y is 2 and x is 0, provided is a compound of Formula (I-n):

(I-n)

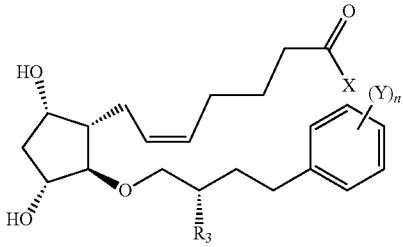

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

As generally defined above, in certain embodiments, provided is a compound of Formula (II):

(II)

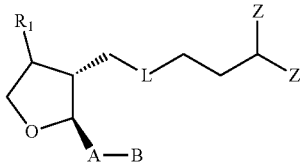

or a pharmaceutically acceptable salt, hydrate, solvate, stereoisomer, polymorph, tautomer, isotopically enriched derivative, or prodrug thereof, wherein A, B, X, Z, L, and $R_1$ are as defined herein are as defined herein.

In certain embodiments, L is a group of the formula

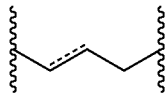

wherein ====== represents a single bond.

In certain embodiments, L is a group of the formula

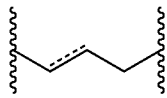

wherein ====== represents a double bond which can be in the cis or trans configuration. In certain embodiments, the double bond is in the cis configuration. In certain embodiments, the double bond is in the trans configuration In certain embodiments, L is a group of the formula

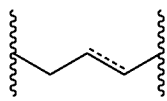

wherein ====== represents a single bond.

In certain embodiments, L is a group of the formula

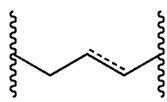

wherein ====== represents a double bond which can be in the cis or trans configuration. In certain embodiments, the double bond is in the cis configuration. In certain embodiments, the double bond is in the trans configuration In certain embodiments of Formula (II), the compound of Formula (II-a):

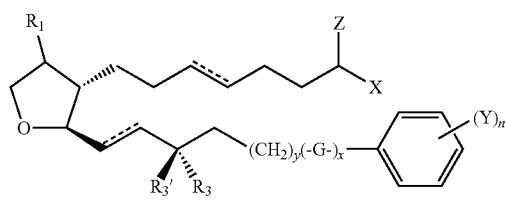

(II-a)

or a pharmaceutically acceptable salt, hydrate, solvate, stereoisomer, polymorph, tautomer, isotopically enriched derivative, or prodrug thereof, wherein ======, $R_1$, Z, X, Y, G, $R_3$, $R_3'$, y, x, and n are as defined herein.

In certain embodiments of Formula (II-a), wherein $R_3'$ is hydrogen, the compound is of Formula (II-b):

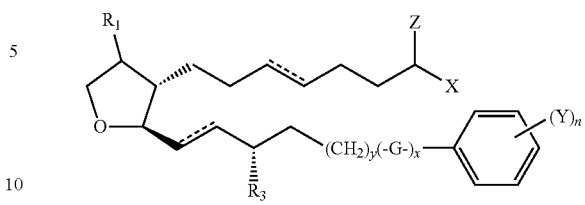

(II-b)

or a pharmaceutically acceptable salt, hydrate, solvate, stereoisomer, polymorph, tautomer, isotopically enriched derivative, or prodrug thereof; wherein ======, $R_1$, $R_3$, Z, X, Y, G, y, x, and n are as defined herein.

In certain embodiments of Formula (II-a), wherein $R_3$ is hydrogen, the compound is of Formula (II-c):

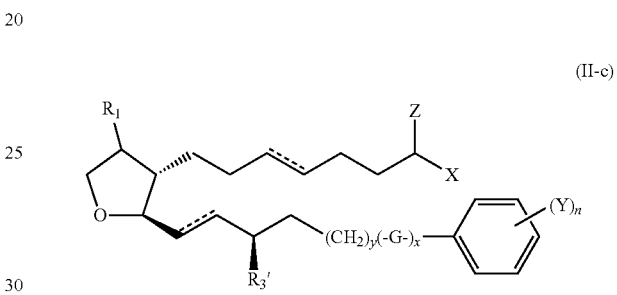

(II-c)

or a pharmaceutically acceptable salt, hydrate, solvate, stereoisomer, polymorph, tautomer, isotopically enriched derivative, or prodrug thereof; wherein ======, $R_1$, $R_2$, $R_3'$, Z, X, Y, G, y, x, and n are as defined herein.

In certain embodiments, G is —O—. In certain embodiments, G is —S—.

In certain embodiments of Formula (II-a), wherein G is —O—, provided is a compound of Formula (II-a1):

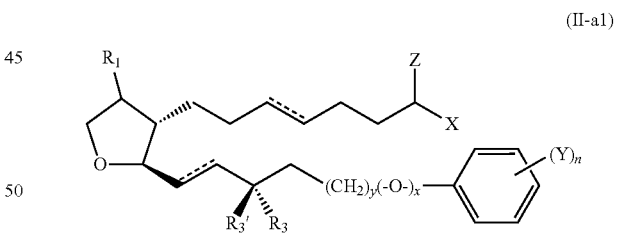

(II-a1)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ====== $R_1$, $R_2$, $R_3'$, Z, X, Y, y, x, and n are as defined herein.

In certain embodiments, Z is =O.

In certain embodiments at least one exocyclic ====== represents a cis-double bond.

For example, in certain embodiments of Formula (II-a1), wherein Z is =O, provided is a compound of Formula (II-d):

(II-d)

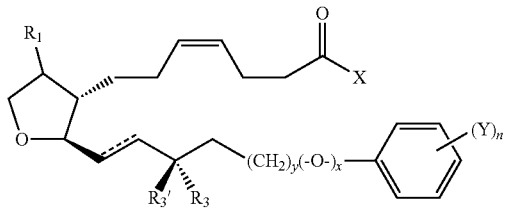

or a pharmaceutically acceptable salt, hydrate, solvate, stereoisomer, polymorph, tautomer, isotopically enriched derivative, or prodrug thereof; wherein ═════ R₁, R₃, R₃', Y, X, y, x, and n are as defined herein.

In certain embodiments of Formula (II-d), wherein R₁ is OH, R₃' is hydrogen, R₃ is —OH, y is 0, and x is 1, provided is a compound of Formula (II-e):

(II-e)

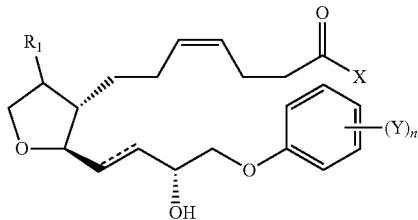

or a pharmaceutically acceptable salt, hydrate, solvate, stereoisomer, polymorph, tautomer, isotopically enriched derivative, or prodrug thereof; wherein ═════ , Y, X, and n are as defined herein.

Exemplary compounds of Formula (I) include, but are not limited to:

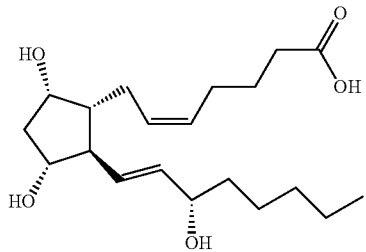 [SMILES: CCCCC[C@H](O)/C=C/[C@@H]1[C@@H](C/C=C\CCCC(=O)O)[C@@H](O)C[C@H]1O]

referred to herein as Prostaglandin F2α;

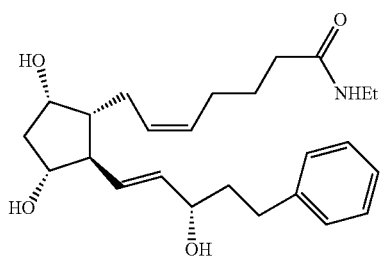

also referred to herein as bimatoprost;

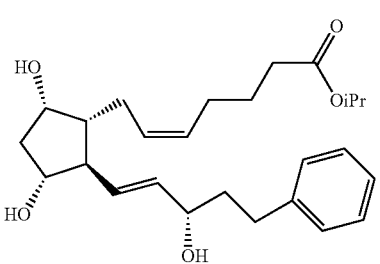 [SMILES: CC(C)OC(=O)CCC/C=C\C[C@@H]1[C@@H](/C=C/[C@@H](O)CCc2ccccc2)[C@H](O)C[C@@H]1O]

also referred to herein as bimatoprost isopropyl ester;

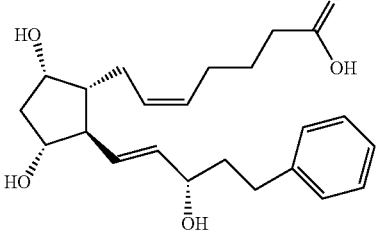

also referred to herein as bimatoprost free acid;

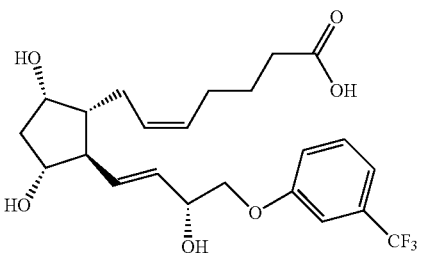 [SMILES: O=C(O)CCC/C=C\C[C@@H]1[C@@H](/C=C/[C@@H](O)COc2cccc(C(F)(F)F)c2)[C@H](O)C[C@@H]1O]

also referred to herein as travoprost;

also referred to herein as travoprost free acid or fluprostenol;

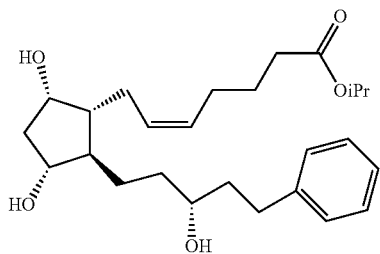 [SMILES: CC(C)OC(=O)CCC/C=C\C[C@@H]1[C@@H](CC[C@@H](O)CCc2ccccc2)[C@H](O)C[C@@H]1O]

also referred to herein as latanoprost;

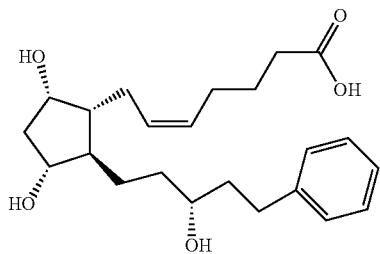 [SMILES: O=C(O)CCC/C=C\C[C@@H]1[C@@H](CC[C@@H](O)CCc2ccccc2)[C@H](O)C[C@@H]1O]

also referred to herein as latanoprost free acid;

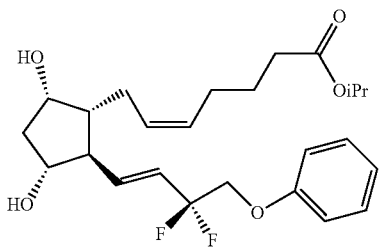

also referred to herein as tafluprost;

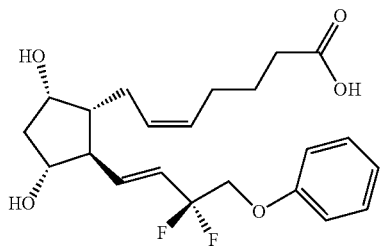

also referred to herein as tafluprost free acid or AFP-172;

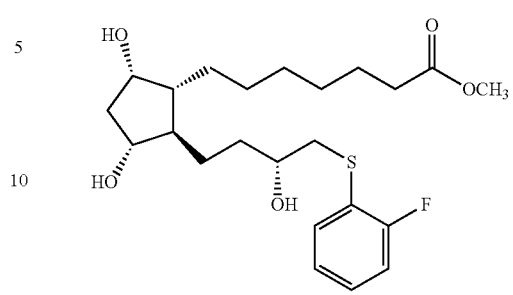

also referred to herein as CAY10509;

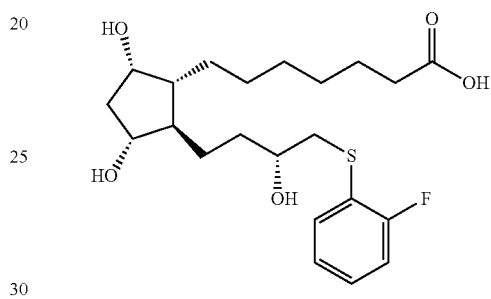

also referred to herein as CAY10509 free acid;

and 9-, 11-, and/or 15-ester derivatives (e.g., prodrugs) of the above, e.g., of formula:

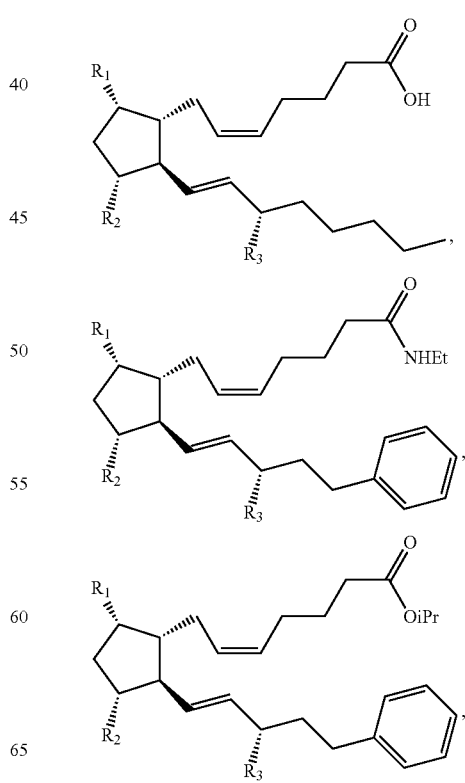

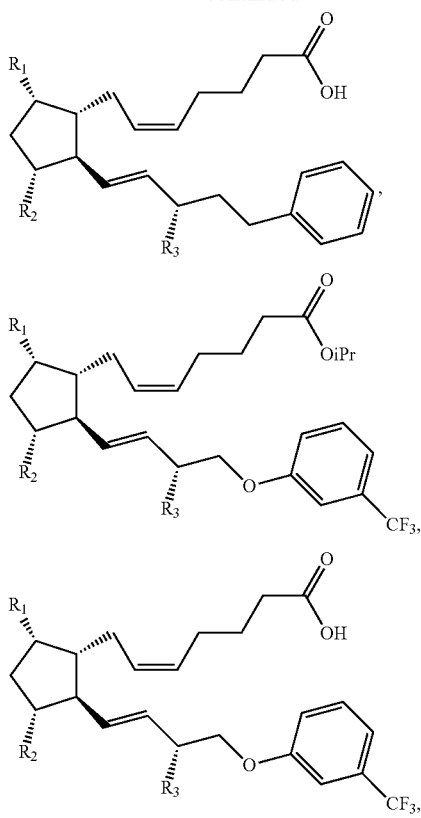

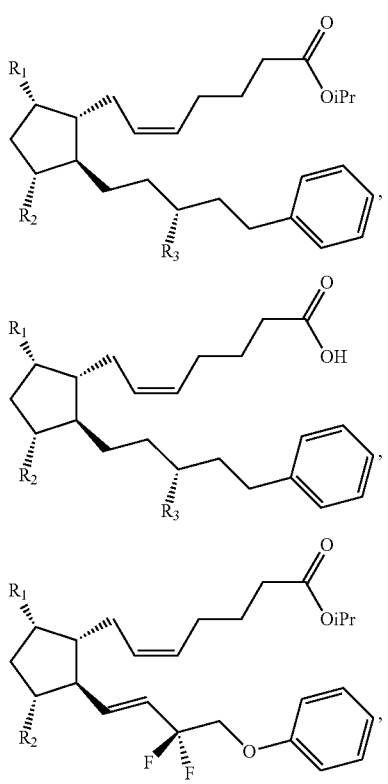

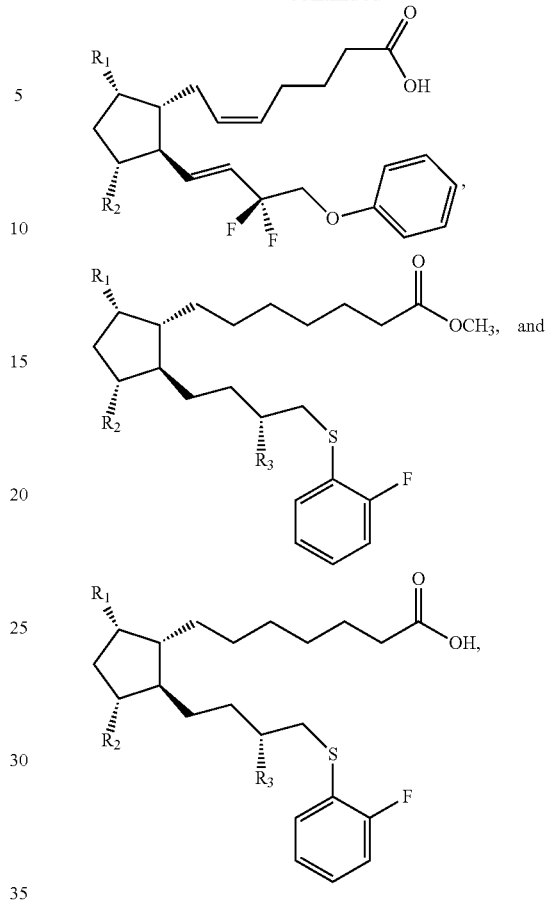

wherein:
$R_1$ is —O(CO)$R_6$ and $R_2$ is —OH, or
$R_1$ is —OH, $R_2$ is —O(CO)$R_6$, or
$R_1$ is —OH, $R_2$ is —OH, and $R_3$ is —O(CO)$R_8$, or
$R_1$ is —OH, $R_2$ is —O(CO)$R_6$, and $R_3$ is —OH, or
$R_1$ is —O(CO)$R_6$, $R_2$ is —O(CO)$R_6$, and $R_3$ is —OH, or
$R_1$ is —O(CO)$R_6$, $R_2$ is —OH, and $R_3$ is —O(CO)$R_8$, or
$R_1$ is —OH, $R_2$ is —O(CO)$R_6$, and $R_3$ is —O(CO)$R_8$, or
$R_1$ is —O(CO)$R_6$, $R_2$ is —O(CO)$R_6$, and $R_3$ is —O(CO)$R_8$, wherein $R_6$ and $R_8$ are as defined herein, and pharmaceutically acceptable salts, hydrates, solvates, stereoisomers, polymorphs, tautomers, isotopically enriched derivatives, and prodrugs thereof. In certain embodiments, $R_8$ is —(CH$_2$)$_q$CH$_3$ wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_6$ is —(CH$_2$)$_r$CH$_3$, wherein r is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$.

In certain embodiments, the compound of Formula (I) is selected from the group consisting of latanoprost, latanoprost free acid, tafluprost, tafluprost free acid, travoprost, fluprostenol, bimatoprost, bimatoprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost, latanoprost free acid, tafluprost, tafluprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of latanoprost free acid and pharmaceutically acceptable salts, hydrates, solvates, stereoisomers, polymorphs, tautomers, isotopically enriched derivatives, and prodrugs thereof. In certain embodiments, the compound of Formula (I) is latanoprost. In certain embodiments, the compound of Formula (I) is selected from the group consisting of tafluprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of tafluprost free acid and pharmaceutically acceptable salts, hydrates, solvates, stereoisomers, polymorphs, tautomers, isotopically enriched derivatives, and prodrugs thereof. In certain embodiments, the compound of Formula (I) is tafluprost.

Exemplary compounds of Formula (II) include, but are not limited to,

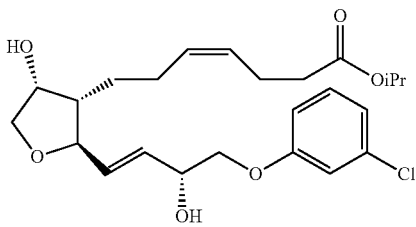 [SMILES: CC(C)OC(=O)CC/C=C\CC[C@H]1[C@@H](O)CO[C@@H]1/C=C/[C@@H](O)COc1cccc(Cl)c1]

also referred to as AL-12182;

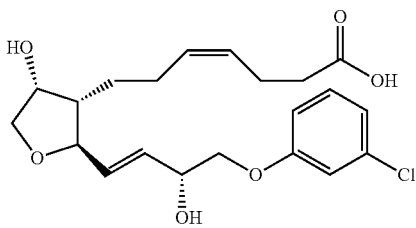 [SMILES: O=C(O)CC/C=C\CC[C@H]1[C@@H](O)CO[C@@H]1/C=C/[C@@H](O)COc1cccc(Cl)c1]

also referred to as AL-12182 free acid;

and ester derivatives (e.g., prodrugs) of the above, e.g., of formula:

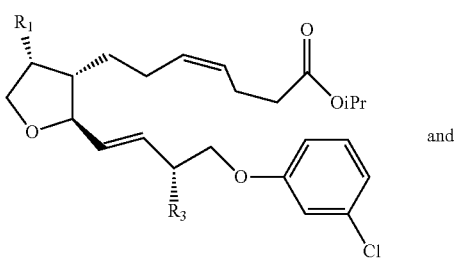

and

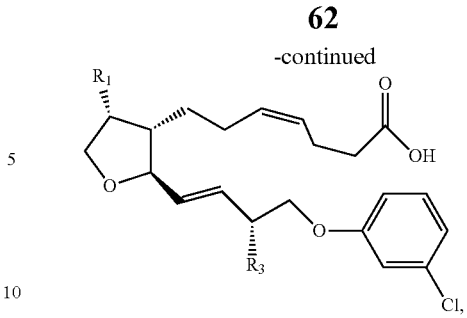

wherein:
$R_1$ is —OH and $R_3$ is —O(CO)$R_8$, or
$R_1$ is —O(CO)$R_6$, and $R_3$ is —OH, or
$R_1$ is —O(CO)$R_6$, and $R_3$ is —O(CO)$R_8$,
wherein $R_6$ and $R_8$ are as defined herein, and pharmaceutically acceptable salts, hydrates, solvates, stereoisomers, polymorphs, tautomers, isotopically enriched derivatives, and prodrugs thereof. In certain embodiments, $R_8$ is —(CH$_2$)$_q$CH$_3$, wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_6$ is —(CH$_2$)$_r$CH$_3$, wherein r is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$.

In certain embodiments, the compound of Formula (I) or (II) is a prodrug of any one of the compounds described herein. Exemplary prodrugs include esters, amides, and/or thioamides of the parent free acid, and compounds wherein a hydroxyl group on the parent compound (e.g., a pentacyclic hydroxyl group $R_1$ and/or $R_2$ or the hydroxyl group at the $R_3$ and/or $R_3$' position) is esterified, e.g., 9-, 11-, and/or 15-ester derivatives as described herein, e.g., wherein the ester at said position is a $C_{1-6}$ ester, e.g., 9-propionyl bimatoprost, 11-propionyl bimatoprost, 15-propionyl bimatoprost, 9-butyryl bimatoprost, 11-butyryl bimatoprost, 15-butyryl bimatoprost, and the like.

Compositions and Formulations

In certain embodiments, the present invention provides compositions for topical administration of a composition comprising a PFPRA compound, as described herein, and a fatty acid ester (e.g., isopropyl myristate). Compositions, as used herein, encompass pharmaceutical compositions as well as cosmetic compositions.

In certain embodiments, the composition comprises a PFPRA compound, fatty acid ester (e.g., isopropyl myristate), and an ointment base. In some embodiments, the composition further comprises an organic alcohol, e.g., methanol, ethanol, propanol, isopropanol, 1,3-butanediol, ethylene glycol, or propylene glycol. In certain embodiments, the organic alcohol is propylene glycol. In certain embodiments, the composition comprises latanoprost, isopropyl myristate, and an ointment base. In certain embodiments, the composition comprises tafluprost, isopropyl myristate, and an ointment base. In certain embodiments, the composition consists essentially of the above-recited components. In certain embodiments, the composition is not irritating to the skin. In certain embodiments, the composition is sterile, endotoxin-free or essentially endotoxin-free, ophthalmic, and/or ophthalmically compatible.

Kalayoglu (PCT/US2012/021692; WO2012/099942) teaches certain formulations for systemic (transdermal) delivery of a PFPRA to the bloodstream. These include two emulsions (Lipoderm or pluronic lecithin organogel). Emulsions are challenging to manufacture and susceptible to phase separation; e.g., for example, pluronic lecithin organogel is prone to phase separation at temperatures of about 5°

C. or below. Thus, in some embodiments, the composition is a non-emulsion, i.e., is not an emulsion. In some embodiments, the composition in a non-emulsion comprising a PFPRA compound, fatty acid ester (e.g., isopropyl myristate), and an ointment base. In some embodiments, the composition is a non-emulsion comprising a PFPRA compound, fatty acid ester (e.g., isopropyl myristate), an organic alcohol, and an ointment base.

In some embodiments, the PFPRA compound is a compound of Formula (I) or (II), or a pharmaceutically acceptable salt, hydrate, solvate, stereoisomer, polymorph, tautomer, isotopically enriched derivative, or prodrug thereof. In some embodiments, the PFPRA compound is latanoprost, tafluprost, travoprost, or bimatoprost, or a pharmaceutically acceptable salt, hydrate, solvate, stereoisomer, polymorph, tautomer, isotopically enriched derivative, or prodrug thereof. In certain embodiments, the PFPRA compound is selected from the group consisting of latanoprost, latanoprost free acid, tafluprost, tafluprost free acid, and pharmaceutically acceptable salts, hydrates, solvates, stereoisomers, polymorphs, tautomers, isotopically enriched derivatives, and prodrugs thereof. In certain embodiments, the PFPRA compound is selected from the group consisting of latanoprost and pharmaceutically acceptable hydrates, solvates, stereoisomers, polymorphs, tautomers, isotopically enriched derivatives, and prodrugs thereof. In certain embodiments, the PFPRA compound is selected from the group consisting of latanoprost free acid and pharmaceutically acceptable salts, hydrates, solvates, stereoisomers, polymorphs, tautomers, isotopically enriched derivatives, and prodrugs thereof. In certain embodiments, the PFPRA compound is selected from the group consisting of tafluprost and pharmaceutically acceptable hydrates, solvates, stereoisomers, polymorphs, tautomers, isotopically enriched derivatives, and prodrugs thereof. In certain embodiments, the PFPRA compound is selected from the group consisting of tafluprost free acid and pharmaceutically acceptable salts, hydrates, solvates, stereoisomers, polymorphs, tautomers, isotopically enriched derivatives, and prodrugs thereof. In certain embodiments, the PFPRA compound is latanoprost. In certain embodiments, the PFPRA compound is tafluprost. In certain embodiments, the PFPRA compound hydrolyzes to an active metabolite (e.g., the free acid of latanoprost, tafluprost, travoprost, or bimatoprost) upon administration to the skin.

In some embodiments, the final concentration of the PFPRA compound provided in the composition is between about 0.0001 percent and about 1 percent (by weight). In some embodiments, the final concentration is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive. These percentages are expressed by weight of the total weight of the composition.

In some embodiments, the PFPRA compound is latanoprost and the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, about 0.05 and about 5 percent, or about 0.3 and about 1 percent (by weight), inclusive.

In some embodiments, the PFPRA compound is tafluprost and the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, about 0.05 and about 5 percent, or about 0.3 and about 1 percent (by weight), inclusive. These percentages are expressed by weight of the total weight of the composition.

In some embodiments, the final concentration of the fatty acid ester (e.g., isopropyl myristate) is between about 1 percent to about 20 percent by weight, inclusive. In some embodiments, the final concentration is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the fatty acid ester (e.g., isopropyl myristate) is 1, 2, 3, 4, 5, 6, 7, 8, 9, 10, 11, 12, 13, 14, 15, 16, 17, 18, 19, or 20 percent by weight. These percentages are expressed by weight of the total weight of the composition.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 and about 5 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive. These percentages are expressed by weight of the total weight of the composition.

In some embodiments, the composition comprises an ointment base, e.g., a hydrocarbon base. In some embodiments, the hydrocarbon base is selected from the group consisting of white wax, yellow wax, hard paraffin wax, petroleum jelly, and cetyl esters wax. In some embodiments, the final concentration of ointment base is between about 50 percent and about 99 percent by weight. In some embodiments, the final concentration of ointment base is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. In some embodiments, the ointment base is petroleum jelly, and the final concentration of petroleum jelly is between about 50 percent and about 99 percent by weight, inclusive. In some embodiments, the final concentration of petroleum jelly is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the composition further comprises an organic alcohol (e.g., propylene glycol). In some embodiments, the final concentration of propylene glycol is between about 5 percent and about 50 percent by weight, inclusive. In some embodiments, the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 45 percent, about 40 percent and about 45 percent, or about 45 percent and about 50 percent, inclusive.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 and about 5 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. These percentages are expressed by weight of the total weight of the composition.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In certain embodiments, the composition may further comprise other pharmaceutically acceptable excipients including, but not limited to, solvents, diluents or other liquid vehicles, dispersion or suspension aids, surface active agents, isotonic agents, thickening or emulsifying agents, preservatives, lubricants and the like. General considerations in the formulation and/or manufacture of topical compositions can be found, for example, in *Remington's Pharmaceutical Sciences*, Sixteenth Edition, E. W. Martin (Mack Publishing Co., Easton, Pa., 1980), and *Remington:*

*The Science and Practice of Pharmacy,* 21$^{st}$ Edition (Lippincott Williams & Wilkins, 2005).

In some embodiments, the composition is sterile. Generally, methods of manufacturing a sterile composition include gamma irradiation, heat (e.g., autoclave or dry heat), and microfiltration (e.g., with a 0.2 micron filter); however, some of these methods can be unsuitable for certain compositions. For example, gamma irradiation or heat can cause degradation of the PFPRA compound; oleaginous bases such as petroleum jelly are not amenable to autoclave sterilization; and some excipients may be incompatible or poorly compatible with a 0.2 micron filter.

Compositions can be prepared, packaged, and/or sold in bulk, as a single unit dose, and/or as a plurality of single unit doses. As used herein, a "unit dose" is discrete amount of the composition comprising a predetermined amount of the PFPRA compound. The amount of the PFPRA compound is generally equal to the dosage of the PFPRA compound which would be administered to a subject and/or a convenient fraction of such a dosage such as, for example, one-half or one-third of such a dosage.

Relative amounts of the PFPRA compound, the pharmaceutically acceptable excipient, and/or any additional ingredients in a composition will vary, depending upon the identity, size, and/or condition of the subject treated and further depending upon the route by which the composition is to be administered.

Other Features of Compositions

Pharmaceutically acceptable excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as coloring agents, coating agents, perfuming agents, and sunscreens may also be present in the composition.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include lipids/natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Chlorobutanol, for example, can be used as a preservative in an ointment formulation at a concentration of 0.001% to 1% by weight (such as 0.5% per weight) of the total weight of the final composition.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

A composition of the invention can be combined with, incorporated into, and/or delivered by means of a patch or dressing, which often have the added advantage of providing controlled delivery of the PFPRA compound to the body. Alternatively or additionally, the rate can be controlled by either providing a rate controlling membrane and/or by dispersing the PFPRA compound in a polymer matrix and/or gel.

The composition may further comprise one or more of the additional ingredients described herein. In some embodiments, the additional ingredient is a sunscreen, moisturizer, colorant, antibiotic, antifungal, antiviral, antifibrotic, anti-inflammatory, anesthetic, analgesic, vasoconstrictor, vasodilator, vitamin or mineral, or antioxidant.

Although the descriptions of compositions provided herein are principally directed to compositions that are suitable for topical administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of compositions can be found, for example, in Remington: *The Science and Practice of Pharmacy* 21st ed., Lippincott Williams & Wilkins, 2005.

Still further encompassed by the invention are kits comprising a composition of the invention as described herein and instructions for use. Kits provided may comprise a provided composition and a container (e.g., a tube, vial, ampoule, bottle, syringe, and/or dispenser package, or other suitable container).

Methods of Treatment and Use

As generally described herein, the compositions described herein are contemplated useful in the reduction of subcutaneous fat in a subject in need thereof. Methods of use and treatment include therapeutic methods and cosmetic methods, as described herein. For example, in one aspect, provided is a method of reducing body fat in a subject, comprising topically administering a composition as described herein to a subject in need thereof. In another aspect, provided is a composition of the present invention for use in method of reducing body fat in a subject. In another aspect, provided use of a composition of the present invention in the manufacture of a medicament for reducing body fat in a subject. In certain embodiments, the method is a therapeutic method. In certain embodiments, the method is a cosmetic method.

Fat reduction can include reducing fat as measured by at least one of volume, size, mass, bulk, density, amount, and/or quantity. The present invention is expected to reduce fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%. For example, fat reduction can also include reducing fat cell amount (for example, fat cell number), reducing fat cell volume, reducing fat cell maturation, and/or dedifferentiating a fat cell.

In certain embodiments, the body fat is local, e.g., concentrated on the face, chin, neck, arms, abdomen, chest, breast, buttocks, hips, thighs, legs, and/or knees.

In certain embodiments, the subject suffers from or is likely to suffer from obesity, excess fat on the breast, excess fat on the chin, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, HIV lipodystrophy, orbital fat prolapse, age-related descent of abnormal fat, other acquired lipodystrophy, familial lipodystrophy, lipoma, lipomatosis, or Madelung disease. In certain embodiments, the subject suffers from or is likely to suffer from obesity, gynecomastia, HIV lipodystrophy, lipoma, steatoblepharon, excess eyelid fat, excess periorbital fat, or excess fat on the chin. In certain embodiments, the subject has a cosmetic condition.

In certain embodiments, the subject suffers from or is likely to suffer from excess submental fat. Thus, in one aspect, provided is a composition for use in for reducing fat in a subject suffering from excess submental fat. In another aspect, provided is a method of treating excess submental fat in a subject, comprising topically administering (e.g., applying to the submental skin of the subject) a composition as described herein to a subject in need thereof. In another aspect, provided is a composition as described herein for use in a method of treating excess submental fat in a subject. In another aspect, provided is use a composition as described herein in the manufacture of a medicament for treating excess submental fat in a subject.

In certain embodiments, the subject suffers from or is likely to suffer from steatoblepharon. Thus, in one aspect, provided is a composition for use in for reducing fat in a subject suffering from steatoblepharon. In another aspect, provided is a method of treating steatoblepharon in a subject, comprising topically administering (e.g., applying to an eyelid of the subject) a composition as described herein to a subject in need thereof. In another aspect, provided is a composition as described herein for use in a method of treating steatoblepharon in a subject. In another aspect, provided is use a composition as described herein in the manufacture of a medicament for treating steatoblepharon in a subject.

As described herein, the route of administering is topical. In certain embodiments, the administering is to a body part selected from the group consisting of the face, chin, submental region, jowls, cheeks, periorbital skin, neck, arms, abdomen, chest, breast, buttocks, hips, thighs, legs, and knees.

In certain embodiments, the subject has excess body fat as a side effect of medication (e.g., for example, cortisol and analogs, corticosteroids, megace, sulfonylureas, anti-retrovirals, antidepressants, monoamine oxidase inhibitors, selective serotonin reuptake inhibitors, oral contraceptives, insulin or a form of insulin, risperidone, clozapine, and thiazolidinediones).

In certain embodiments, the subject has excess body fat due to changes in hormonal status (e.g., as a result of physiologic changes such as pregnancy or menopause).

In certain embodiments, the subject with excess body fat is undergoing or has recently undergone smoking cessation.

In certain embodiments, the subject has body fat of cosmetic significance, for example, due to age-related orbital fat prolapse, excess submental fat, or descent of the malar fat pads.

This aspect of invention may also be useful as an adjunct to any of various kinds of surgery and/or non-invasive therapy, whether used in the pre-operative, peri-operative, or post-operative period. The invention further contemplates uses preceding abdominal, thoracic, oncologic, endocrine, neurologic, transplant, and dermatologic surgery, whereby surgical exposure may be improved; preceding or following orthopedic procedures, whereby surgical exposure as well as post-operative recovery may be improved; and preceding cosmetic procedures using lasers, another type of radiation, thermal therapy, cryotherapy, ultrasound, electrolysis, chemical treatment and the like, e.g., skin tightening, skin resurfacing, collagen remodeling, and the like.

Process for Manufacturing a Sterile Ointment

For ophthalmic use, e.g., application on the eyelid for reduction of steatoblepharon, a sterile composition is preferred. Certain of the inventive formulations (e.g., a composition comprising latanoprost, isopropyl myristate, and petrolatum) are not compatible with all forms of sterilization. For example, the inventors found that gamma irradiation caused degradation of latanoprost (Example 14). Petroleum jelly is incompatible with autoclave sterilization and poorly suited for microfiltration.

The inventors sought a practicable alternative. Having discovered that latanoprost is exceptionally soluble in isopropyl myristate (Example 3), the inventors developed a manufacturing process (cf. Example 4) comprising the steps of: (1) dissolving the PFPRA (e.g., latanoprost) and optionally other components (e.g., chlorobutanol) in the fatty acid ester (e.g., isopropyl myristate) to make a solution; (2) microfiltration of the solution (e.g., under aseptic conditions) to make a sterile filtrate; and (3) addition of the filtrate to sterile petroleum jelly, which is optionally liquefied, e.g., by heating (e.g., from about 40° C. to about 70° C., e.g., about 50 to about 60° C.); and (4) mixing to obtain a uniform mixture. Upon reading the Examples, the skilled artisan can appreciate several advantages to combining the latanoprost and PFPRA compound prior to microfiltration, as opposed to filtering these components separately: latanoprost is very viscous and poorly suited to microfiltration; the volume of latanoprost is generally small and therefore prone to measurement error (i.e., imprecision) and losses in the so-called "dead space" of the microfilter; and diluting the latanoprost in the isopropyl myristate promotes uniformity of the latanoprost in the final composition. However, the skilled artisan will also appreciate that the strategy of dissolving the latanoprost in the isopropyl myristate would not be practicable, except for the fortuitously good solubility found by the inventors (Example 3). Furthermore, a surprising and advantageous property of mixing the isopropyl myristate in the petroleum jelly is that it substantially reduces the viscosity of the mixture, as compared to that of the pure petroleum jelly. This not only facilitates mixing (thereby promoting uniformity of the mixture) but also renders the composition more flowable and spreadable on the skin, i.e., the pharmaceutical composition is easier to dispense from a container and apply to the skin.

Thus, in another aspect, provided is a process for manufacturing one or more of the inventive compositions in a sterile fashion, whereby the composition is sterile, endotoxin-free, and ophthalmically compatible, and therefore suitable for use on the eyelid or near the eye. For example, in one embodiment, provided is a process for manufacturing a sterile ointment, comprising dissolving a PFPRA compound (e.g. latanoprost or tafluprost) in a fatty acid ester (e.g., isopropyl myristate) to make a solution; microfiltration of the solution to make a filtrate; and combining the filtrate with an ointment base (e.g., a hydrocarbon base such as petroleum jelly). In certain embodiments, the method further comprises dissolving a preservative (e.g., chlorobutanol) in the fatty acid ester (e.g., isopropyl myristate).

EXAMPLES

Throughout the description, where compositions are described as having, including, or comprising specific components, it is contemplated that these compositions may also consist essentially of, or consist of, the recited components. Further, it should be understood that the order of steps or order for performing certain actions are immaterial so long as the invention remains operable. Moreover, two or more steps or actions may be conducted simultaneously. In light of the foregoing description, the specific non-limiting examples presented below are for illustrative purposes and not intended to limit the scope of the invention in any way.

Example 1

A composition for local reduction of subcutaneous fat was prepared as follows:

TABLE 1

| Ingredients | Amount |
| --- | --- |
| Latanoprost | 100 mg |
| Isopropyl myristate | 5 g |
| Propylene glycol | 15 g |
| White petroleum jelly | 79.9 g |

Neat latanoprost was added to a mixture of propylene glycol and isopropyl myristate. To the resulting mixture was added melted petroleum jelly. The mixture was stirred thoroughly and allowed to cool, yielding about 100 grams of an ointment with a final latanoprost concentration of 0.1% (w/w). It was noted that the compared to pure petrolatum, the mixture was more flowable, more spreadable, more easily mixed (i.e., requiring less force to mix), and more easily dispensed from a container, e.g., a jar or compressible tube (i.e., requiring less force and flowing in a more controlled manner).

Example 2

A composition for local reduction of subcutaneous fat was prepared as follows:

TABLE 2

| Ingredients | Amount per 100 g of composition |
| --- | --- |
| Latanoprost | 0.3 g |
| Chlorobutanol, anhydrous | 0.5 g |
| Isopropyl myristate | 5 g |
| White petroleum jelly | 94.2 g |

Chlorobutanol was dissolved in isopropyl myristate, and to the resulting solution neat latanoprost was added and dissolved. To the resulting solution was added melted petroleum jelly. The mixture was stirred thoroughly and allowed to cool, yielding about 100 grams of an ointment with a final latanoprost concentration of 0.3% (w/w). Compositions were prepared according to the above formula at various scales ranging from about 50 to about 1000 g. Furthermore, comparable formulations comprising 0.1%, 0.15%, and 0.5% (w/w) were likewise prepared, with the difference in latanoprost content balanced by the amount of petroleum jelly. On HPLC analysis, these compositions were found to be uniform and to have the correct potency.

Example 3

The solubility of latanoprost in a 10:1 solution of isopropyl myristate and chlorobutanol was assessed by a standard (USP) protocol at 25° C. The upper limit of solubility at this temperature was found to be about 60 to about 85 mg/g. This high degree of solubility was surprising, because latanoprost is insoluble or poorly soluble in most solvents. Furthermore, this high degree of solubility was crucial for practicing the aseptic process described in the next example.

Example 4

A sterile, ophthalmically compatible composition for local reduction of fat was prepared as follows:

TABLE 3

| Ingredients | Amount |
| --- | --- |
| Latanoprost | 100 mg |
| Chlorobutanol, anhydrous | 0.5 g |
| Isopropyl myristate | 5 g |
| White petroleum jelly | 94.4 g |

The process was carried out aseptically. Chlorobutanol (CB) was dissolved in isopropyl myristate (IM). To this solution latanoprost was added and readily dissolved. The resulting solution was filtered through a 0.2 micron filter to yield a filtrate, which was placed in a sterile vessel. To the vessel was added sterile, melted petroleum jelly. The mixture was stirred thoroughly, yielding about 100 grams of a uniform ointment with a final latanoprost concentration of 0.1% (w/w). On laboratory analysis, the ointment was sterile and free of endotoxins. A comparable ointment comprising 0.3% (w/w) was prepared, with the additional latanoprost replacing a like amount of petroleum jelly. The skilled artisan will appreciate that the above process requires latanoprost solubility in the IM:CB solution of at least 18 or 55 mg/g for the 0.1% and 0.3% products, respectively.

Example 5

Compositions were prepared according to Example 2 and stored in a tight-sealed container at room temperature. The latanoprost concentration, uniformity, and lack of impurities were verified by High Performance Liquid Chromatography (HPLC). The composition was stored and reanalyzed and tested on HPLC at regular intervals for 2 months. At each interval, organoleptic inspection showed physical stability of the composition, and HPLC shows a stable latanoprost concentration and a lack of known degradants (e.g., latanoprost free acid, 15-keto latanoprost). Thus, it was concluded that the composition demonstrates excellent physical and chemical stability.

Example 6

Skin permeation studies were conducted with various formulations of latanoprost, ex vivo, on fresh human skin. Fresh human skin was obtained from live donors undergoing abdominoplasty and mounted on a standard (Franz-type) diffusion cell apparatus. All formulations contained 0.8% of latanoprost, expressed as weight of latanoprost per total weight of the composition. Each test article (8 mg) was uniformly applied to a skin surface of 0.8 cm$^2$. All formulations were tested on skin from at least two different donors. Treated skin was left open to the atmosphere to simulate clinical conditions. Receptor fluid flowed continuously over 24 hours and was collected in fractions. The amount of drug (latanoprost free acid) in these fractions was determined by High-Performance Liquid Chromatography (HPLC) with ultraviolet detection. The following amounts of drug were recovered from receptor fluid over 24 hours:

TABLE 4

| Vehicle Formulation | Drug mass (ng, mean) |
| --- | --- |
| PG 15%, IM 5%, WPJ 80% | 10,808 |
| PG 15%, PS 5%, WPJ 80% | 3795 |
| PG 7.5%, LL 7.5%, PS 5%, WPJ 80% | 3635 |
| PG 7.5%, PS 5%, WPJ 87.5% | 2082 |
| PG 15%, PS 15%, WPJ 70%, | 1127 |
| Ethanol 70%, PG 30% | 3930 |
| Ethanol 75%, DGME 25% | 1260 |
| Ethanol 75%, LL 25% | 890 |
| Ethanol 50%, LL 25%, DGME 25% | 840 |
| DMSO 99% Gel | 5850 |

DGME = diethylene glycol monomethyl ether, DMSO = dimethylsulfoxide, IM = isopropyl myristate, LL = lauryl lactate, PG = propylene glycol, PS = polysorbate 80, WPJ = white petroleum jelly.

Thus, a formulation of latanoprost comprising isopropyl myristate in a hydrocarbon base provided substantially more dermal drug penetration compared to similar formulations lacking isopropyl myristate. The formulation comprising isopropyl myristate also provided superior drug penetration to a positive control, which is DMSO 99% Gel, and compared to a range of other formulations comprising enhancers such as lauryl lactate, polysorbate 80, and diethylene glycol monoethyl ether.

Example 7

Skin permeation studies were conducted with various formulations of latanoprost, ex vivo, on fresh pig skin, according to methods as described in the foregoing example. All formulations contained 0.25% of latanoprost, expressed as weight of latanoprost per total weight of the composition. The following flux values for LFA were observed over 24 hours:

TABLE 5

| Vehicle Formulation | LFA flux (ng/cm$^2$/h) |
| --- | --- |
| MO 15%, IM 5%, WPJ 80% | 8 |
| IM 5%, WPJ 95% | 18 |
| MO 15%, WPJ 85% | 6 |
| IM 5%, MO 95% | 2 |

IM = isopropyl myristate, MO = mineral oil, WPJ = white petroleum jelly.

Thus, a formulation of latanoprost comprising petroleum jelly and isopropyl myristate, but lacking mineral oil, provided superior delivery of LFA to formulations of latanoprost comprising mineral oil with isopropyl myristate, petroleum jelly, or both.

Example 8

Compositions as described in Example 2, comprising latanoprost at a final concentration of 0.1% or 0.5%, were tested in Gottingen minipigs (3 animals per dose concentration). All animals were treated once daily for 10 days, over 10% of body surface area on the dorsal skin. Animals were monitored for skin condition, body weight, and safety. Serial plasma samples were taken to assess pharmacokinetics. Twenty-four hours after the last dose, animals were sacrificed. Skin and fat were dissected from the treatment area. Tissues were examined histologically. Tissue was also used to measure drug (LFA) concentrations in subcutaneous fat (mid-depth of tissue) by liquid chromatography/tandem mass spectrometry (LC/MS/MS). The product was well tolerated, with no adverse effects in any animal. LFA concentrations in subcutaneous fat and plasma on Day 10 are shown in Table 6.

TABLE 6

| Formulation | Duration | LFA in mid-depth fat (µg/g) (trough level) |
| --- | --- | --- |
| 0.10% latanoprost 5% IM, 0.5% CB, 94.4% petroleum jelly | 10 days | 0.2 |
| 0.50% latanoprost, 5% IM, 0.5% CB, 94% petroleum jelly | 10 days | 1 |

CB = chlorobutanol;
IM = isopropyl myristate

Thus, the compositions were well tolerated and, following application to a thick-skinned mammal, delivered LFA locally to subcutaneous fat.

Example 9

Compositions as described in Example 2, comprising latanoprost at a final concentration of 0.1% or 0.5%, were tested on the periocular skin of Gottingen minipigs (3 animals per dose concentration). All animals were treated once daily for 10 days. Animals were monitored for skin condition, body weight, and safety. Twenty-four hours after the last dose, animals were sacrificed. Skin and fat were dissected from the treatment area. Some of this tissue was examined histologically. The product was well tolerated, with no adverse effects in any animal.

Example 10

Formulations consisting of latanoprost (0.1% or 0.5%), chlorobutanol 0.5%, isopropyl myristate 5%, and white petroleum jelly q.s. (all w/w) were tested in a standard rabbit ocular irritation test. The formulations did not cause any adverse effects.

Example 9

A composition comprising isopropyl myristate 5%, propylene glycol 15%, and white petroleum jelly 80% (without active ingredient) was applied to skin on the volar forearms on healthy adult men and women (n=4). The application area was 5 cm×5 cm. Application was once daily for 7 consecutive days. Skin condition and participant experience were noted daily, with results as follows:

TABLE 4

| Participant | Skin Condition | Participant Experience |
| --- | --- | --- |
| 1 | Normal (100%) | Well-tolerated, aesthetically pleasing |
| 2 | Normal (100%) | Well-tolerated, aesthetically pleasing |
| 3 | Normal (100%) | Well-tolerated, aesthetically pleasing |
| 4 | Normal (100%) | Well-tolerated, aesthetically pleasing |

Thus, the above formulations were non-irritating and aesthetically pleasing when applied to human skin.

Example 10

Different compositions, comprising latanoprost, e.g., 0.1% w/w, are tested on obese mice. Mice approximately six weeks old, all with similar baseline body mass, are randomized and prospectively treated as follows (n=5 animals per group):

TABLE 5

| Group | Compound | Formulation (w/w) |
|---|---|---|
| A | Vehicle only | White petroleum jelly 100% |
| B | Vehicle only | IM 5%, CB 0.5%, white petroleum jelly q.s. |
| C | Latanoprost | White petroleum jelly q.s. |
| D | Latanoprost | IM 5% CB 0.5%, white petroleum jelly q.s. |

The dose is 0.1 cc to the right flank, daily. Mice are fed ad libitum and weighed daily for about 28 days. On or about day 28, mice are sacrificed and samples of skin with subcutaneous fat are collected for histologic examination. It is predicted that after about 28 days, mice in Group D will show relatively less weight gain (or more weight loss) and relatively less adiposity compared to mice in any of Groups A, B, or C. Thus, it is predicted that in a mouse model of obesity, the foregoing results show superior reduction of adiposity with a latanoprost formulation comprising petroleum jelly, chlorobutanol, and isopropyl myristate, as compared to a equimolar latanoprost formulation with a vehicle consisting essentially of petroleum jelly.

Example 11

A composition consisting essentially of latanoprost 0.5%, isopropyl myristate 5%, chlorobutanol 0.5%, and white petroleum jelly 94% (all w/w) was administered to the dorsal skin (10% of body surface area) of six Gottingen minipigs, once daily for 13 weeks. An equal number of animals are treated with a placebo composition, consisting essentially of isopropyl myristate 5%, chlorobutanol 0.5%, and white petroleum jelly 94.5%. (all w/w). Animals were observed for safety and tolerability. The compositions were well tolerated in all animals. After 13 weeks, animals were sacrificed and dorsal skin, fat, and muscle were dissected en bloc from a standardized portion of the treatment area. As compared to animals treated with the placebo composition, there was gross atrophy, i.e., a thickness reduction of 30% to 70%, of subcutaneous fat in animals treated with the latanoprost 0.5% article.

Example 12

From the study described in Example 11, a portion of the tissue is fixed in formalin, stained with hematoxylin and eosin, and examined histopathologically. Subcutaneous fat thickness is measured systematically, for example by measuring the thickness of fat from the dermis to the panniculus carnosus using image analysis software such as ImageJ (National Institutes of Health). From another portion of the tissue, subcutaneous fat is dissected, washed, pulverized, and homogenized, with the homogenate submitted for quantification of latanoprost free acid concentration using liquid chromatography with tandem mass spectrometry (a method known in the art). It is predicted that the composition containing latanoprost will be associated with reduced subcutaneous fat thickness, as compared to control. It is further predicted that the latanoprost composition will be associated with amounts of latanoprost free acid in subcutaneous fat that are considered therapeutically effective, with reference to other in vivo experiments and in vitro assays. It is further predicted that the latanoprost composition of this example will be associated with higher tissue concentrations of latanoprost free acid and/or higher degrees of subcutaneous fat reduction compared to other formulations hitherto disclosed.

Example 13

The following experiment describes a randomized, placebo-controlled, double-blind trial in human subjects to test whether the safety and efficacy of a PFPRA compound composition for reduction of submental fat. The composition can be, for example, as described in Example 2, wherein the PFPRA compound is latanoprost. Alternatively, the PFPRA compound can be, for example, tafluprost.

Eligible subjects (for example, n=60) with excess submental fat are entered into a randomized double-blind study. Subjects are randomized in 1:1 fashion to receive either the active composition (for example, comprising latanoprost 0.3%), or the corresponding inactive vehicle. Subjects are instructed to apply, once a day, a dose of 0.5 ml in a thin film the chin. Serial clinical assessments, photographs, and magnetic resonance imaging (MRI) scans are performed prior to the first dose and then at 13 weeks. Treatment continues for a total of 13 weeks. It is contemplated that over time, for example after 13 weeks of treatment, the composition comprising latanoprost (or tafluprost) will be associated with more reduction in the depth and/or volume of submental fat, as measured by clinical assessment and/or MRI, as compared to vehicle alone.

Example 14

The following experiment describes a randomized, placebo-controlled, double-blind trial in human subjects to test whether the safety and efficacy of a PFPRA compound composition for reduction of periorbital fat. The composition can be, for example, a sterile composition as described in Example 4, wherein the PFPRA compound is latanoprost. Alternatively, the PFPRA compound can be, for example, tafluprost.

Eligible subjects (for example, n=60) with excess periorbital fat are entered into a randomized double-blind study. Subjects are randomized in 1:1 fashion to receive either the active composition (for example, comprising latanoprost 0.1%), or the corresponding inactive vehicle. Subjects are instructed to apply, once a day, a dose of 0.1 ml in a thin film the periorbital skin. Serial clinical assessments and photographs are performed prior to the first dose and then at 6 and 12 weeks. Treatment continues for a total of 12 weeks. It is contemplated that over time, for example after 12 weeks of treatment, the composition comprising latanoprost (or other active ingredient) will be associated with more reduction in the volume of periorbital fat, as measured by clinical assessment, as compared to vehicle alone.

Example 15

A latanoprost ointment was prepared according to Example 2 and subjected to various doses of gamma radiation, as are commonly used for sterilization. A validated HPLC method was used to evaluate the ointment for latanoprost content and degradants. Significant degradation of latanoprost was observed at all gamma radiation doses. Thus, it was found that gamma irradiation is not suitable for sterilizing compositions comprising latanoprost.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for reducing body fat in a subject, the method comprising administering to the subject a composition comprising latanoprost, isopropyl myristate, and petroleum jelly.
2. The method of claim 1, wherein the method locally reduces body fat in the subject.
3. The method of claim 1, wherein the method reduces subcutaneous fat in the subject.
4. The method of claim 1, wherein the composition consists essentially of latanoprost, isopropyl myristate, and petroleum jelly.
5. The method of claim 1, wherein the latanoprost concentration is between about 0.001% and about 1% w/w, inclusive.
6. The method of claim 5, wherein the latanoprost concentration is between about 0.01% and about 0.5% w/w, inclusive.
7. The method of claim 1, wherein the isopropyl myristate concentration is between about 1% and about 20% w/w, inclusive.
8. The method of claim 7, wherein the isopropyl myristate concentration is between about 1% and about 10% w/w, inclusive.
9. The method of claim 5, wherein the isopropyl myristate concentration is between about 1% and about 20% w/w, inclusive.
10. The method of claim 9, wherein the isopropyl myristate concentration is between about 1% and about 10% w/w, inclusive.
11. The method of claim 1, wherein the petroleum jelly concentration is between about 70% and about 99% w/w, inclusive.
12. The method of claim 5, wherein the petroleum jelly concentration is between about 70% and about 99% w/w, inclusive.
13. The method of claim 1, wherein the composition further comprises a preservative.
14. The method of claim 13, wherein the preservative is chlorobutanol.
15. The method of claim 1, wherein the composition is sterile.
16. The method of claim 1, wherein the latanoprost concentration is between about 0.001% and 1% w/w, inclusive; the isopropyl myristate concentration is between about 1% and about 10% w/w, inclusive; and the petroleum jelly concentration is between about 70% and about 99% w/w, inclusive.
17. The method of claim 1, wherein the step of administering is performed about once a day.
18. The method of claim 1, wherein the step of administering comprises administering the composition to the face, chin, neck, arms, abdomen, chest, breast, buttocks, hips, thighs, legs, and/or knees.
19. The method of claim 1, wherein the step of administering comprises administering the composition to the eyelids.
20. The method of claim 1, wherein the step of administering comprises administering the composition to the submental region.
21. The method of claim 1, wherein the latanoprost concentration is between about 0.03% and about 0.1% w/w, inclusive.
22. The method of claim 21, wherein the composition consists essentially of latanoprost, isopropyl myristate, and petroleum jelly.
23. The method of claim 16, wherein the latanoprost concentration is between about 0.03% and about 0.1% w/w, inclusive.
24. The method of claim 23, wherein the composition consists essentially of latanoprost, isopropyl myristate, and petroleum jelly.
25. The method of claim 1, wherein the latanoprost concentration is about 0.1% w/w.

26. The method of claim 25, wherein the composition consists essentially of latanoprost, isopropyl myristate, and petroleum jelly.

27. The method of claim 16, wherein the latanoprost concentration is about 0.1% w/w.

28. The method of claim 27, wherein the composition consists essentially of latanoprost, isopropyl myristate, and petroleum jelly.

* * * * *